(12) United States Patent
Semenov et al.

(10) Patent No.: US 11,253,164 B2
(45) Date of Patent: Feb. 22, 2022

(54) USE OF ELECTROMAGNETIC FIELD FOR TOMOGRAPHIC IMAGING OF HEAD

(71) Applicant: EMTensor GmbH, Vienna (AT)

(72) Inventors: Serguei Y Semenov, Vienna (AT);
Abouzar Hamidipour, Vienna (AT);
Markus Hopfer, Schwanberg (AT);
Ramon Planas Badenas, Vienna (AT)

(73) Assignee: EMTensor GmbH, Vienna (AT)

( * ) Notice: Subject to any disclaimer, the term of this patent is extended or adjusted under 35 U.S.C. 154(b) by 440 days.

(21) Appl. No.: 16/420,543

(22) Filed: May 23, 2019

(65) Prior Publication Data

US 2019/0274578 A1 Sep. 12, 2019

Related U.S. Application Data

(63) Continuation of application No. PCT/US2017/063169, filed on Nov. 23, 2017.
(Continued)

(51) Int. Cl.
*A61B 5/0522* (2021.01)
*A61B 5/00* (2006.01)
(Continued)

(52) U.S. Cl.
CPC .......... *A61B 5/0522* (2013.01); *A61B 5/0042* (2013.01); *H01Q 13/10* (2013.01); *G06T 11/006* (2013.01)

(58) Field of Classification Search
CPC ................ A61B 5/0522; A61B 5/0042; A61B 2562/222; A61B 2562/227; A61B 2562/166; H01Q 13/10; G06T 11/006
See application file for complete search history.

(56) References Cited

U.S. PATENT DOCUMENTS

| 4,135,131 A | 1/1979 | Larsen et al. |
| 4,157,472 A | 6/1979 | Beck, Jr. et al. |

(Continued)

FOREIGN PATENT DOCUMENTS

| EP | 2404550 A1 | 1/2012 |
| EP | 2404550 B1 | 11/2015 |

(Continued)

OTHER PUBLICATIONS

"European Extended Search Report of the European Patent Office" in European Patent Application No. 16856382.3 for EMTensor GmbH, dated Apr. 24, 2019, 7 pages.
(Continued)

*Primary Examiner* — Peter Luong
(74) *Attorney, Agent, or Firm* — Tillman Wright, PLLC; James D. Wright; David R. Higgins

(57) ABSTRACT

An electromagnetic tomographic system for imaging a human head includes a base, an imaging chamber, at least one ring of antennas, a plurality of antenna controllers, and an image processing computer system. The imaging chamber is supported on the base and defines an imaging domain in which the head is received. The antennas are supported by the imaging chamber and encircle the imaging domain. Each controller comprises circuitry carried on a printed circuit board and is dedicated to a respective antenna. Each controller controls operation of a corresponding antenna. In operation, while one antenna is transmitting an electromagnetic signal into the imaging domain, a plurality of the antennas are simultaneously receiving the signal after passing through the imaging domain. The received signals of the plurality of antennas are simultaneously measured. Data representative of the measure electromagnetic signals is output by the controllers and used for image processing.

27 Claims, 26 Drawing Sheets
(1 of 26 Drawing Sheet(s) Filed in Color)

Related U.S. Application Data

(60) Provisional application No. 62/426,101, filed on Nov. 23, 2016.

(51) Int. Cl.
*H01Q 13/10* (2006.01)
*G06T 11/00* (2006.01)

(56) References Cited

U.S. PATENT DOCUMENTS

| | | |
|---|---|---|
| 4,247,815 A | 1/1981 | Larsen et al. |
| 4,257,278 A | 3/1981 | Papadofrangakis et al. |
| 4,638,813 A | 1/1987 | Turner |
| 4,662,722 A | 5/1987 | Johnson |
| 4,798,209 A | 1/1989 | Klingenbeck et al. |
| 4,805,627 A | 2/1989 | Klingenbeck et al. |
| 4,926,868 A | 5/1990 | Larsen |
| 5,069,223 A | 12/1991 | McRae |
| 5,222,501 A | 6/1993 | Ideker et al. |
| 5,233,713 A | 8/1993 | Murphy et al. |
| 5,263,050 A | 11/1993 | Sutterlin et al. |
| 5,305,748 A | 4/1994 | Wilk |
| 5,363,050 A | 11/1994 | Guo et al. |
| 5,405,346 A | 4/1995 | Grundy et al. |
| 5,715,819 A | 2/1998 | Svenson et al. |
| 5,757,326 A * | 5/1998 | Koyama .......... H01Q 1/22 343/702 |
| 5,800,350 A | 9/1998 | Coppleson et al. |
| 6,026,173 A | 2/2000 | Svenson et al. |
| 6,073,047 A | 6/2000 | Barsamian et al. |
| 6,332,087 B1 | 12/2001 | Svenson et al. |
| 6,333,087 B1 | 12/2001 | Jerdee et al. |
| 6,490,471 B2 | 12/2002 | Svenson et al. |
| 6,503,203 B1 | 1/2003 | Rafter et al. |
| 6,511,427 B1 | 1/2003 | Sliwa, Jr. et al. |
| 6,522,910 B1 | 2/2003 | Gregory |
| 6,697,660 B1 | 2/2004 | Robinson |
| 6,865,494 B2 | 3/2005 | Duensing et al. |
| 7,239,731 B1 | 7/2007 | Semenov et al. |
| 7,272,431 B2 | 9/2007 | McGrath |
| 7,340,292 B2 | 3/2008 | Li |
| 7,876,114 B2 | 1/2011 | Campbell et al. |
| 8,000,775 B2 | 8/2011 | Pogue et al. |
| 8,089,417 B2 | 1/2012 | Popovic et al. |
| 8,207,733 B2 | 6/2012 | Meaney et al. |
| 8,253,619 B2 | 8/2012 | Holbrook et al. |
| 8,376,948 B2 | 2/2013 | Brannan |
| 8,437,843 B1 | 5/2013 | Kayyali et al. |
| 8,708,919 B1 | 4/2014 | Frazier |
| 8,724,864 B2 | 5/2014 | Persson et al. |
| 9,072,449 B2 | 7/2015 | Semenov |
| 9,414,749 B2 | 8/2016 | Semenov |
| 9,414,763 B2 | 8/2016 | Semenov |
| 9,414,764 B2 | 8/2016 | Semenov |
| 9,675,254 B2 | 6/2017 | Semenov |
| 9,675,255 B2 | 6/2017 | Semenov |
| 9,724,010 B2 | 8/2017 | Semenov |
| 9,924,873 B2 | 3/2018 | Semenov |
| 10,492,700 B2 | 12/2019 | Semenov |
| 10,921,361 B2 | 2/2021 | Semenov |
| 2002/0017905 A1 | 2/2002 | Conti |
| 2002/0168317 A1 | 11/2002 | Daighighian et al. |
| 2002/0191744 A1 | 12/2002 | Mirabelle |
| 2003/0018244 A1 | 1/2003 | Haddad et al. |
| 2003/0088180 A1 | 5/2003 | Van Veen et al. |
| 2003/0090276 A1 | 5/2003 | Weide et al. |
| 2004/0123667 A1 | 7/2004 | McGrath |
| 2004/0174948 A1 | 9/2004 | Kojima et al. |
| 2004/0220465 A1 | 11/2004 | Cafarella |
| 2005/0135560 A1 | 6/2005 | Dafni et al. |
| 2005/0203387 A1 | 9/2005 | Godshalk et al. |
| 2006/0133564 A1 | 6/2006 | Langan et al. |
| 2006/0247531 A1 | 11/2006 | Pogue et al. |
| 2006/0276714 A1 | 12/2006 | Holt et al. |
| 2007/0025514 A1 | 2/2007 | Lawaczeck |
| 2007/0238957 A1 | 10/2007 | Yared |
| 2007/0239004 A1 | 10/2007 | Kakee et al. |
| 2008/0319437 A1 | 12/2008 | Turner et al. |
| 2009/0015832 A1 | 1/2009 | Popovic et al. |
| 2009/0292195 A1 | 11/2009 | Boyden et al. |
| 2010/0010340 A1 | 1/2010 | Godavarty et al. |
| 2010/0067770 A1 | 3/2010 | Persson et al. |
| 2010/0174179 A1 | 7/2010 | Persson et al. |
| 2011/0022325 A1 | 1/2011 | Craddock et al. |
| 2011/0172512 A1 | 7/2011 | Yan et al. |
| 2011/0263961 A1 | 10/2011 | Craddock et al. |
| 2011/0282609 A1 | 11/2011 | Liu et al. |
| 2011/0295102 A1 | 12/2011 | Lakkis et al. |
| 2012/0010493 A1 | 1/2012 | Semenov |
| 2012/0083683 A1 | 4/2012 | Kuwabara |
| 2012/0083690 A1 | 4/2012 | Semenov |
| 2012/0172954 A1 | 7/2012 | Zastrow et al. |
| 2012/0179037 A1 | 7/2012 | Halmann |
| 2012/0190977 A1 | 7/2012 | Persson et al. |
| 2013/0002264 A1 | 1/2013 | Gaerber |
| 2013/0257426 A1 | 10/2013 | Feiweier et al. |
| 2014/0024917 A1 | 1/2014 | McMahon et al. |
| 2014/0155740 A1 | 6/2014 | Semenov |
| 2014/0275944 A1 | 9/2014 | Semenov |
| 2014/0276012 A1 | 9/2014 | Semenov |
| 2014/0378812 A1 | 12/2014 | Saroka et al. |
| 2015/0257648 A1 | 9/2015 | Semenov |
| 2015/0257649 A1 | 9/2015 | Semenov |
| 2015/0342472 A1 | 12/2015 | Semenov |
| 2016/0256109 A1 | 9/2016 | Semenov |
| 2016/0262623 A1 | 9/2016 | Semenov |
| 2016/0324489 A1 | 11/2016 | Crawford et al. |
| 2016/0345856 A1 | 12/2016 | Semenov |
| 2017/0273563 A1 | 9/2017 | Semenov |
| 2018/0231594 A1 | 8/2018 | Semenov |
| 2018/0235486 A1 | 8/2018 | Semenov |
| 2018/0344165 A1 | 12/2018 | Semenov |
| 2019/0357801 A1 | 11/2019 | Semenov et al. |
| 2019/0357802 A1 | 11/2019 | Semenov et al. |
| 2019/0357803 A1 | 11/2019 | Semenov et al. |

FOREIGN PATENT DOCUMENTS

| | | |
|---|---|---|
| EP | 3037035 A1 | 6/2016 |
| EP | 3361955 A1 | 8/2018 |
| EP | 3037035 | 11/2019 |
| EP | 2967478 B1 | 5/2020 |
| EP | 3361955 B1 | 9/2020 |
| RU | 2449729 C2 | 5/2012 |
| WO | 9532665 | 12/1995 |
| WO | 199852464 A1 | 11/1998 |
| WO | 200015109 A1 | 3/2000 |
| WO | 00/64343 A1 | 11/2000 |
| WO | 2005115235 A1 | 12/2005 |
| WO | 2007136334 A1 | 11/2007 |
| WO | 2008002251 A1 | 1/2008 |
| WO | 2010100649 A1 | 9/2010 |
| WO | 2011009945 A2 | 1/2011 |
| WO | 2011156810 A2 | 12/2011 |
| WO | 2011156810 A3 | 12/2011 |
| WO | 2013005134 A2 | 1/2013 |
| WO | 2013005134 A3 | 1/2013 |
| WO | 2014081992 A2 | 5/2014 |
| WO | 2014150616 A2 | 9/2014 |
| WO | 2014150618 A1 | 9/2014 |
| WO | 2014150616 A3 | 12/2014 |
| WO | 2014081992 A3 | 8/2015 |
| WO | 2017066731 A1 | 4/2017 |
| WO | 2017066731 A8 | 5/2018 |
| WO | 2018098387 A1 | 5/2018 |

OTHER PUBLICATIONS

Yongjie Jessica Zhang et al.: "A New Method to Improve Quality of Reconstructed Images in Tomography". In: "Computational Modeling of Objects Presented in Images. Fundamentals, Methods, and Applications". Jan. 1, 2014 (Jan. 1, 2014), Springer, USA, pp. 267-272.

(56) References Cited

OTHER PUBLICATIONS

Zhu et al.: "An improved back-projection algorithm for electrical impedance tomography", Automation Congress, 2008. WAC 2008. World, IEEE, Piscataway, NJ, USA, Sep. 28, 2008 (Sep. 28, 2008), pp. 1-4, XP031371153, ISBN: 978-1-889335-38-4.

"International Preliminary Report" and "Written Opinion of the International Searching Authority" (ISA/US) in EMTensor GmbH, International Patent Application Serial No. PCT/US2017/063169, dated Jun. 6, 2019 (19 pages).

Abubakar, A.; van den Berg, P.M. and Mallorqui, J.J. (2002). "Imaging of biomedical data using a multiplicative regularized contrast source inversion method", IEEE Transactions of Microwave Theory and Techniques 50 : 1761-1771. (10 pages).

Bulyshev, A.E.; Souvorov, A.E.; Semenov, S. Y. ; Posukh, V.G. and Sizov, Y. E. (2004). "Three-dimensional vector microwave tomography: theory and computational experiments", Inverse Problems 20 : 1239.

Bulyshev, A.E.; Souvorov, A. E.; Semenov, S.Y.; Svenson, R.H.; Nazarov, A.G.; Sizov, Y.E. and Tatsis, G. P. (2000) "Three-dimensional microwave tomography. Theory and computer experiments in scalar approximation", Inverse Problems 16 : 863.

Chew, W. C. and Wang, Y. M. (1990). "Reconstruction of two-dimensional permittivity distribution using the distorted Born iterative method", IEEE Transactions on Medical Imaging 9 : 218-225. (8 pages).

Devaney, A. J. (1992). Current research topics in diffraction tomography. In: Bertero, M. & Pike, E. (Ed.), Inverse Problems in Scattering and Imaging, Adam Hilger, New York.

Fear, Elise C., et al. "Confocal microwave imaging for breast cancer detection: Localization of tumors in three dimensions." IEEE Transactions of Biomedical Engineering 49.8 (2002): 812-822. (11 pages).

Harada, H.; Wall, D. J. N.; Takenaka, T. and Tanaka, M. (1995). "Conjugate gradient method applied to inverse scattering problem", IEEE Transactions on Antennas and Propagation 43 : 784-792. (9 pages).

Hawley, M.S., et al., "Microwave Imaging of Tissue Blood Content Changes," Journal of Biomedical Engineering (1991), pp. 197-202, vol. 13, No. 3, published by Butterworth-Heinermann for BES (6 pages).

Joachimowicz, N.; Mallorqui, J. J.; Bolomey, J. C. and Broquets, A. (1998). "Convergence and stability assessment of Newton-Kantorovich reconstruction algorithms for microwave tomography," IEEE Transactions on Medical Imaging 17 : 562-570. (9 pages).

Jofre, L., et al., "Medical Imaging with a Microwave Tomographic Scanner," IEEE Transactions on Biomedical Engineering (Mar. 1990), pp. 303-312, vol. 37, No. 3 (10 pages).

Kleinman, R. and den Berg, P. (1992). "A modified gradient method for two-dimensional problems in tomography," Journal of Computational and Applied Mathematics 42 : 17-35.

Lobel, P.; Kleinman, R. E.; Pichot, C.; Blanc-Feraud, L. and Barlaud, M. (1996). "Conjugate-Gradient Method for Soliving Inverse Scattering with Experimental Data", IEEE Antennas and Propagation Magazine 38 : 48.

Meaney, P. M.; Paulsen, K. D.; Hartov, A. and Crane, R. K. (1996). "Microwave imaging fortissue assessment: initial evaluation in multitarget tissue-equivalent phantoms", IEEE Transactions on Biomedical Engineering 43 : 878-890. (12 pages).

Semenov, S.Y.; Posukh, V.G.; Bulyshev, A. E.; Williams, T.; Clark, P.; Sizov, Y.E.; Souvorov, A. E.; Voinov, B.A.: "Development of Microwave Tomography for Functional Cardiac Imaging." Biomedical Imaging: Macro to Nano, 2004. IEEE International Symposium on Arlington, VA, USA IEEE Apr. 15, 2004 (Apr. 15, 2004), pp. 1351-1353, XP010774114, DOI: 10.1109/ISBI.2004.1398797 ISBN: 978-0-7803-8389-0 (3 pages).

Semenov, S.Y.; Simonova, G. I.; Starostin, A.N.; Taran, M.G.; Souvorov, A.E.; Bulyshev, A.E. Svenson, R.H.; Nazarov, A.G.; Sizov, Y.E.,; Posukh, V.G.; Pavlovsky, A. and Tatsis G.P. (2001) "Dielectrical Model of Cellular Structures in Radio Frequency and Microwave Spectrum. Electrically Interacting Versus Noninteracting Cells." Annals of Biomedical Engineering, vol. 29. pp. 427-435. (8 pages).

Semenov, S. Y.; Bulyshev, A. E.; Abubakar, A.; Posukh, V. G.; Sizov, Y. E.; Souvorov, A. E.; van den Berg, P. M. and Williams, T. C. (2005). Microwave-tomographic imaging of the high dielectric-contrast objects using different imagereconstruction approaches, IEEE Transactions on Microwave Theory and Techniques 53 : 2284-2294. (10 pages).

Semenov, S. Y.; Bulyshev, A. E.; Souvorov, A. E.; Svenson, R. H.; Sizov, Y. E.; Vorisov, V. Y.; Posukh, V. G.; Kozlov, I. M.; Nazarov, A. G. and Tatsis, G. P. (1998). Microwave tomography: theoretical and experimental investigation of the iteration reconstruction algorithm, IEEE Transactions on Microwave Theory and Techniques 46 : 133-141. (9 pages).

Semenov, S. Y.; Bulyshev, A. E.; Posukh, V. G.; Sizov, Y. E.; Williams, T. C. and Souvorov, A. E. (2003). Microwave Tomography for Detection/Imaging of Myocardial Infarction. I. Excised Canine Hearts, Annals of Biomedical Engineering 31 : 262-270. (9 pages).

Semenov, S., et al., "Microwave Tomography of Extremities: 1. Dedicated 2D System and Physiological Signatures," Physics in Medicine and Biology (2011), pp. 2005-2017, vol. 56, No. 7, published by Institute of Physics and Engineering in Medicine, United Kingdom (13 pages).

Semenov, S.Y.: "Microwave tomography: review of the progress towards clinical applications", Philosophical Transactions of The Royal Society, vol. 2009, No. 367, Dec. 31, 2009. pp. 3021-3042, XP002661164. DOI: 10.1098/rsta.2009.0092 the whole document. (22 pages).

Semenov, S.Y.; Kellam, J.; Althausen, P.; Williams, T.; Abubakar, A.; Bulyshev, A.; Sizov, Y. (2007) "Microwave tomography for functional imaging of extremity soft tissues: feasibility assessment." Physics in Medicine and Biology, doi: 10.1088/0031-9155/52/18/015. (15 pages).

Semenov, S.Y. et al.: "Myocardial ischemia and infarction can be detected by microwave spectroscopy. II. Biophysical reconstruction", Engineering in Medicine and Biology Society, 1996. Bridging Disciplines for Biomedicine., 18th Annual International Conference of the IEEE Amsterdam, Netherlands Oct. 31-Nov. 3, NY, NY, IEEE vol. 4 Oct. 31, 1996 pp. 1363-1364, XP010261997, DOI: 10.1109/EMBS. 1996.647455 ISBN:978-0-7803-3811-1.

Souvorov, A. E.; Bulyshev, A. E.; Semenov, S. Y.; Svenson, R. H.; Nazarov, A. G.; Sizov, Y. E. and Tatsis, G. P. (1998). Microwave tomography: a two-dimensional Newton iterative scheme, IEEE Transactions on Microwave Theory and Techniques 46 : 1654-1659. (6 pages).

Yaniv, Ziv, et al. "Electromagnetic tracking in the clinical environment." Medical physics 36.3 (2009): 876-892 (17 pages).

"Extended European Search Report," European Patent Application No. 13856581.7, for EMTensor GmbH, et al., dated Aug. 25, 2016 (7 pages).

"European Search Report" and "Written Opinion of the European Patent Office" in European Patent Application No. 11275103.7 for EMImaging Limited, dated Oct. 13, 2011 (5 pages).

"Extended European Search Report," European Patent Application No. 14768372.6, for EMTensor GmbH, et al., dated Sep. 16, 2016 (10 pages).

"Extended European Search Report," European Patent Application No. 14768384.1, for EMTensor GmbH, et al., dated Oct. 20, 2016 (7 pages).

"Extended European Search Report," European Patent Application No. 15193895.8, for EMTensor GmbH, dated May 25, 2016 (6 pages).

"International Preliminary Report on Patentability" of the International Bureau of WIPO in EMTensor GmbH, International Patent Application Serial No. PCT/US2013/071360, dated Jul. 7, 2015 (17 pages).

"International Search Report" and "Written Opinion of the International Searching Authority" (ISA/US) in EMTensor GmbH, International Patent Application Serial No. PCT/US2013/071360, dated May 27, 2014 (20 pages).

"International Search Report" and "Written Opinion of the International Searching Authority" (ISA/US) in EMTensor GmbH, International Patent Application Serial No. PCT/US2014/023793, dated Oct. 31, 2014 (11 pages).

(56) References Cited

OTHER PUBLICATIONS

"International Search Report" and "Written Opinion of the International Searching Authority" (ISA/US) in EMTensor GmbH, International Patent Application Serial No. PCT/US2014/023803, dated Jun. 25, 2014 (9 pages).

"International Search Report" and "Written Opinion of the International Searching Authority" (ISA/US) in EMTensor GmbH, International Patent Application Serial No. PCT/US2016/057254, dated Jan. 12, 2017 (7 pages).

"International Search Report" and "Written Opinion of the International Searching Authority" (ISA/US) in EMTensor GmbH, International Patent Application Serial No. PCT/US2017/063169, dated Jan. 30, 2018 (20 pages).

"International Preliminary Report" and "Written Opinion of the International Searching Authority" (ISA/US) in EMTensor GmbH, International Patent Application Serial No. PCT/US2016/057254, dated Apr. 26, 2018 (6 pages).

"Extended European Search Report," European Patent Application No. 17873810.0, for EMTensor GmbH, et al., dated Jul. 9, 2020 (11 pages).

Igney et al. "Design and performance of a planar-array MIT system with normal sensor alignment: Planar-array MIT system with normal sensor alignment", Physiological Measurement, Institute of Physics Publishing, Bristol, GB, vol. 26, No. 2, Apr. 1, 2005 (Apr. 1, 2005), pp. S263-S278, (16 pages).

Poltschak et al., "High precision realtime RF-measurement system for imaging of stroke", 2017 47th European Microwave Conference (EUMC), European Microwave Association, Oct. 10, 2017, pp. 864-867, (4 pages).

Zheng et al., "A multi-channel magnetic induction tomography measurement system for human brain model imaging", Physiological Measurement, vol. 30, No. 6, Jun. 1, 2009, pp. S175-S186, (11 pages).

Zulkarnay et al., "Advancements in Transmitters and Sensors for Biological Tissue Imaging in Magnetic Induction Tomography", Sensors, vol. 12, No. 12, Dec. 29, 2012, pp. 7126-7156, (20 pages).

\* cited by examiner

USE OF ELECTROMAGNETIC FIELD FOR TOMOGRAPHIC IMAGING OF HEAD

CROSS REFERENCE TO RELATED APPLICATIONS

The present application is a U.S. continuation patent application of, and claims priority under 35 U.S.C. § 120 to, International Application No. PCT/US2017/63169, filed Nov. 23, 2017, designating the U.S., and entitled "USE OF ELECTROMAGNETIC FIELD FOR TOMOGRAPHIC IMAGING OF HEAD," which '169 application published as WO 2018/098387 A1 on May 31, 2018, which '169 application and the application publication thereof are each expressly incorporated herein by reference in their entirety, and which '169 application, for purposes of the United States, is a U.S. nonprovisional patent application of, and claims priority under 35 U.S.C. § 119(e) to, U.S. provisional patent application Ser. No. 62/426,101, filed Nov. 23, 2016 and entitled "USE OF ELECTROMAGNETIC FIELD FOR TOMOGRAPHIC IMAGING OF HEAD," which '101 application is expressly incorporated by reference herein in its entirety. In addition, each of the following patents, patent applications and patent application publications is incorporated by reference herein in its entirety:

(a) U.S. Pat. No. 9,414,749 to Semenov, issued Aug. 16, 2016 and previously published on Jun. 5, 2014 as U.S. Patent Application Publication No. 2014/0155740 A1, which is intended, at least, to provide background and technical information with regard to the systems and environments of the inventions of the current patent application;

(b) International Publication No. WO 2017/066731 A1, which was published Apr. 20, 2017 based on International Patent Application Serial No. PCT/US2016/57254 to Semenov, filed Oct. 16, 2016 and entitled "ELECTROMAGNETIC INTERFERENCE PATTERN RECOGNITION TOMOGRAPHY," which is intended, at least, to provide explanation of pattern recognition techniques and their application to electromagnetic tomography; and (c) U.S. Patent Application Publication No. 2012/0010493 A1, which was published Jan. 12, 2012 based on U.S. patent application Ser. No. 13/173,078 to Semenov, filed Jun. 30, 2011 and entitled "SYSTEMS AND METHODS OF ELECTROMAGNETIC TOMOGRAPHY (EMT) DIFFERENTIAL (DYNAMIC) FUSED IMAGING," which is intended to provide background and technical information with regard to 4D EMT imaging.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE PRESENT INVENTION

Field of the Present Invention

The present invention relates generally to electromagnetic tomography for imaging a human head, and, in particular, to the use of improved matching media formulations, localized antenna control circuitry, simultaneous data measurements, improved EM fields calibration, and improved normalization techniques in systems and methods of electromagnetic tomography for imaging a human head.

Background

Electromagnetic tomography (EMT) is a relatively recent imaging modality with great potential for both biomedical and industrial applications. Biomedical applications include but are not limited to the non-invasive assessment of functional and pathological conditions of biological tissues. Industrial applications include but are not limited to oil and gas exploration, mine search and assessment, and flow assessment within non-metallic pipes. Using EMT, objects such as biological tissues are differentiated and, consequentially, can be imaged based on the differences in the dielectric properties of such objects. EMT is believed to have high potential for biomedical applications based on the recent demonstration of the dependency of tissue dielectric properties on the tissue's various functional and pathological conditions, such as blood and oxygen contents, ischemia and infarction, stroke, malignancies, edema and others.

Two-dimensional (2D), three-dimensional (3D) and even "four-dimensional" (4D) EMT systems and methods of image reconstruction have been developed over the last decade or more. Feasibility of the technology for various biomedical and industrial applications has been demonstrated, for example, for cardiac imaging and extremities imaging.

As in any tomographic imaging, the classical EMT imaging scenario consists of cycles of measurements of complex signals (for example: amplitude and phase), as affected by the presence of an object under study located within a so-called imaging domain, defined by an imaging chamber, as produced by a plurality of transmitters located at various points around the object and measured on a plurality of receivers located at various points around the object. This is illustrated in FIG. 1, which is a simplified schematic illustration of portions of an electromagnetic tomography (EMT) system. The locations of the transmitters and receivers may be within the imaging domain, on the boundary of the imaging domain, or outside the imaging domain. The measured matrix of EM signals may then be used by a data processing system in image reconstruction methods in order to reconstruct 2D or 3D distribution of dielectric properties of the object, and thus, a 2D or 3D image of the object, which for biomedical applications is typically a human body or part of a human body, such as a head, a torso, an arm or the like, but may also be any object without metal shielding.

Generally, it is very important for image reconstruction to precisely describe a distribution of an EM field within the imaging domain. The distribution of an EM field within an imaging chamber is a very complex phenomenon, even when there is no object of interest inside. The use of EM fields for imaging inside of a strongly shielded object (but not metallically shielded) is a problem of even higher complexity. One example of such an application is imaging of the human brain, but it will be appreciated that other such applications of this type might include imaging of any human tissue that is shielded by a bony structure. The EM imaging of the brain or other tissue surrounded by bone presents a very complicated, high dielectric contrast problem. The challenge is to reconstruct hidden properties of deep brain tissues which are effectively shielded by a high dielectric contrast shield, comprising the skull (with dielectric properties in a range of 16+j5) and the cerebral spinal fluid (with dielectric properties in a range of 60+j30).

EMT imaging of high dielectric contrast objects, including biological objects, involves the problem of so-called "diffraction tomography." Although such problem is difficult, mathematical algorithms and corresponding systems and software implementations have been developed that proved to be very reliable and delivered images of objects of different sizes from a few centimeters in the excised canine heart up to a full-size body in 2D, 3D and 3D vector cases. However, such developments are still less than ideal when imaging inside of strongly shielded objects.

More recently, the use of a new interference pattern recognition tomography flow was introduced for generating an accurate representation of EMT imaging of objects that have a high dielectric contrast shield, such as but not limited to the human brain. However, the success of this flow is dependent on accurate and precise measurements generated and received by the plurality of EM hardware devices used when imaging inside of strongly shielded objects, usually but not necessarily disposed on the boundary apparatus. Further improvements, involving hardware, software, or both, are needed for accurately and precisely generating and communicating the EM signals transmitted and received from the EM hardware devices.

SUMMARY OF THE PRESENT INVENTION

Some exemplary embodiments of the present invention may overcome one or more of the above disadvantages and other disadvantages not described above, but the present invention is not required to overcome any particular disadvantage described above, and some exemplary embodiments of the present invention may not overcome any of the disadvantages described above.

Broadly defined, the present invention according to one aspect is an electromagnetic tomographic system for imaging a human head, including: a base; an imaging chamber, supported on the base, that defines an imaging domain in which a human head is received; at least one ring of antennas, supported by the imaging chamber and encircling the imaging domain; a plurality of antenna controllers, each antenna controller comprising circuitry carried on a printed circuit board, wherein each of the plurality of antenna controllers is dedicated to a respective antenna in the ring of antennas, and wherein the circuitry of each respective antenna controller controls operation of the corresponding antenna and also provides, as output, data representative of measured electromagnetic field signals received by such antenna; and an image processing computer system that receives, from the plurality of antenna controllers, the output data representative of the measured electromagnetic field signals received by the respective antennas and derives image data therefrom.

In a feature of this aspect, the circuitry for each respective antenna controller is carried on one or more dedicated printed circuit board that are separate from the respective printed circuit boards for the other antenna controllers. In further features, the circuitry for each antenna controller includes radio frequency (RF) transceiver circuitry that has a transmit side and a receive side that are alternately connected to the antenna using an RF switch; the system further includes a plurality of antenna adapters, wherein each of the plurality of antenna adapters is dedicated to a respective antenna in the ring of antennas, and wherein the antennas and antennas adapters include circuitry that is carried on a dedicated printed circuit board that is separate from the respective printed circuit boards for the other antennas and antenna adapters; the circuitry for each antenna and antenna adapter and the circuitry for the corresponding antenna controller are carried together on a single respective printed circuit board; the circuitry for each antenna and antenna adapter is carried on a first printed circuit board in a first module and the circuitry for the antenna controller corresponding to the antenna and antenna adapter is carried on a second printed circuit board in a second module; each respective first printed circuit board module is connected to its corresponding second printed circuit board module via one or more cable; the second printed circuit boards for all of the antennas are housed together in a location separate from the antenna rings; the plurality of second printed circuit boards are arranged in a ring around the first printed circuit boards such that each respective second printed circuit board is disposed adjacent its corresponding first printed circuit board; the circuitry for each respective antenna controller includes an analog to digital converter (ADC), carried on the one or more dedicated printed circuit board, such that the data representative of measured electromagnetic field signals received by the corresponding antenna may be generated; the circuitry for each respective antenna controller includes a digital signal processor carried on the one or more dedicated printed circuit boards; the circuitry for each respective antenna controller utilizes a superheterodyne technology-based architecture; the circuitry for each respective antenna controller includes a radio frequency (RF) transceiver stage that is connected to the antenna, an intermediate frequency (IF) stage that is connected to the RF transceiver stage, and a baseband (BB) data processing stage that is connected to the intermediate frequency (IF) stage; the baseband (BB) data processing stage produces the data, representative of measured electromagnetic field signals received by the antenna, that is provided as output; the intermediate frequency (IF) stage utilizes quadrature modulation to produce an IF signal that includes both in-phase and quadrature components; a common clock oscillator is provided to the intermediate frequency (IF) stage of each of the plurality of antenna controllers; each intermediate frequency (IF) stage includes a frequency synthesizer, utilizing the common clock oscillator as input, that provides a carrier signal of at least 100 MHz for an analog modulation/demodulation process; and/or the carrier signal provided by the frequency synthesizer for the analog modulation/demodulation process, utilizing the common clock oscillator as input, is at least 1 GHz.

In another feature of this aspect, the imaging chamber is cylindrical and includes at least three rings of antennas. In further features, the imaging chamber includes at least five rings of antennas; the imaging chamber includes six rings of antennas; and/or each of the at least three rings of antennas includes a number of antennas that is equal to the number of antennas in each of the other rings.

In another feature of this aspect, the imaging chamber is semispherical and includes at least three rings of antennas; the imaging chamber includes at least six rings of antennas; and/or each of the at least three rings of antennas includes a number of antennas that is different from the number of antennas in each of the other rings.

In another feature of this aspect, the imaging chamber translates relative to the base; the imaging chamber translates horizontally relative to the base; the imaging chamber translates vertically relative to the base; and/or the imaging chamber rotates upward and downward relative to the base.

In another feature of this aspect, the antennas are waveguide antennas.

In another feature of this aspect, the antennas are slot antennas.

In another feature of this aspect, the image processing computer system is integrated with the electromagnetic tomographic scanner.

In another feature of this aspect, the image processing computer system is disposed in the same room as the electromagnetic tomographic scanner.

In another feature of this aspect, the image processing computer system is disposed in a room that is different from a room in which the electromagnetic tomographic scanner is disposed.

Broadly defined, the present invention according to another aspect is an electromagnetic tomographic system for imaging a human head, including: a base; an imaging chamber, supported on the base, that defines an imaging domain in which a human head is received; at least one ring of antennas, supported by the imaging chamber and encircling the imaging domain; a plurality of antenna controllers, each antenna controller comprising circuitry, utilizing a superheterodyne technology-based architecture, that is dedicated to a respective antenna in the ring of antennas, and wherein the circuitry of each respective antenna controller controls operation of the corresponding antenna and also provides, as output, data representative of measured electromagnetic field signals received by such antenna; and an image processing computer system that receives, from the plurality of antenna controllers, the output data representative of the measured electromagnetic field signals received by the respective antennas and derives image data therefrom.

Broadly defined, the present invention according to another aspect is an electromagnetic tomographic system for imaging a human head, including: a base; an imaging chamber, supported on the base, that defines an imaging domain in which a human head is received; at least one ring of antennas, supported by the imaging chamber and encircling the imaging domain; a plurality of antenna controllers, each antenna controller including radio frequency (RF) transmitter/receiver circuitry that is connected to an antenna of an imaging chamber of an electromagnetic tomographic scanner, an intermediate frequency (IF) stage that is connected to the RF transceiver transmitter/receiver circuitry, and a baseband (BB) data processing stage that is connected to the intermediate frequency (IF) stage, wherein the baseband (BB) data processing stage produces, as output, data representative of measured electromagnetic field signals received by the antenna; and an image processing computer system that receives, from the plurality of antenna controllers, the output data representative of the measured electromagnetic field signals received by the respective antennas and derives image data therefrom.

In a feature of this aspect, the radio frequency (RF) transmitter/receiver circuitry, the intermediate frequency (IF) stage, and the baseband (BB) data processing stage for each respective antenna controller are carried on a dedicated printed circuit board that is separate from the respective printed circuit boards for the other antenna controllers.

Broadly defined, the present invention according to another aspect is an electromagnetic tomographic scanner for use in imaging a human head, including: a base; an imaging chamber, supported on the base, that defines an imaging domain; at least one ring of antennas, supported by the imaging chamber and encircling the imaging domain; a plurality of antenna controllers, each antenna controller comprising circuitry carried on a printed circuit board, wherein each of the plurality of antenna controllers is dedicated to a respective antenna in the ring of antennas, and wherein the circuitry of each respective antenna controller controls operation of the corresponding antenna and also provides, as output, data representative of measured electromagnetic field signals received by such antenna.

In a feature of this aspect, the circuitry for each respective antenna controller is carried on one or more dedicated printed circuit board that are separate from the respective printed circuit boards for the other antenna controllers. In further features, the circuitry for each antenna controller includes radio frequency (RF) transceiver circuitry that has a transmit side and a receive side that are alternately connected to the antenna using an RF switch; the scanner further includes a plurality of antenna adapters, wherein each of the plurality of antenna adapters is dedicated to a respective antenna in the ring of antennas, and wherein the antennas and antennas adapters include circuitry that is carried on a dedicated printed circuit board that is separate from the respective printed circuit boards for the other antennas and antenna adapters; the circuitry for each antenna and antenna adapter and the circuitry for the corresponding antenna controller are carried together on a single respective printed circuit board; the circuitry for each antenna and antenna adapter is carried on a first printed circuit board in a first module and the circuitry for the antenna controller corresponding to the antenna and antenna adapter is carried on a second printed circuit board in a second module; each respective first printed circuit board module is connected to its corresponding second printed circuit board module via one or more cable; the second printed circuit boards for all of the antennas are housed together in a location separate from the antenna rings; the plurality of second printed circuit boards are arranged in a ring around the first printed circuit boards such that each respective second printed circuit board is disposed adjacent its corresponding first printed circuit board; the circuitry for each respective antenna controller includes an analog to digital converter (ADC), carried on the one or more dedicated printed circuit board, such that the data representative of measured complex electromagnetic field signals received by the corresponding antenna may be generated; the circuitry for each respective antenna controller includes a digital signal processor carried on the one or more dedicated printed circuit boards; the circuitry for each respective antenna controller utilizes a superheterodyne technology-based architecture; the circuitry for each respective antenna controller includes a radio frequency (RF) transceiver stage that is connected to the antenna, an intermediate frequency (IF) stage that is connected to the RF transceiver stage, and a baseband (BB) data processing stage that is connected to the intermediate frequency (IF) stage; the baseband (BB) data processing stage produces the data, representative of measured electromagnetic field signals received by the antenna, that is provided as output; the intermediate frequency (IF) stage utilizes quadrature modulation to produce an IF signal that includes both in-phase and quadrature components; a common clock oscillator is provided to the intermediate frequency (IF) stage of each of the plurality of antenna controllers; each intermediate frequency (IF) stage includes a frequency synthesizer, utilizing the common clock oscillator as input, that provides a carrier signal of at least 100 MHz for an analog modulation/demodulation process; the carrier signal provided by the frequency synthesizer for the analog modulation/demodulation process, utilizing the common clock oscillator as input, is at least 1 GHz; the imaging chamber is cylindrical and includes at least three rings of antennas; the imaging chamber includes at least five rings of antennas; the imaging chamber includes six rings of antennas; and/or each of the at least three rings of antennas includes a number of antennas that is equal to the number of antennas in each of the other rings.

In another feature of this aspect, the imaging chamber is semispherical and includes at least three rings of antennas. In further features, the imaging chamber includes at least six rings of antennas; each of the at least three rings of antennas includes a number of antennas that is different from the number of antennas in each of the other rings.

In another feature of this aspect, the imaging chamber translates relative to the base; the imaging chamber translates horizontally relative to the base; the imaging chamber translates vertically relative to the base; and/or the imaging chamber rotates upward and downward relative to the base.

In another feature of this aspect, the antennas are waveguide antennas.

In another feature of this aspect, the antennas are slot antennas.

Broadly defined, the present invention according to another aspect is an electromagnetic tomographic scanner for use in imaging a human head, including: a base; an imaging chamber, supported on the base, that defines an imaging domain; at least one ring of antennas, supported by the imaging chamber and encircling the imaging domain; and a plurality of antenna controllers, each antenna controller comprising circuitry, utilizing a superheterodyne technology-based architecture, that is dedicated to a respective antenna in the ring of antennas; wherein the circuitry of each respective antenna controller controls operation of the corresponding antenna and also provides, as output, data representative of measured electromagnetic field signals received by such antenna.

Broadly defined, the present invention according to another aspect is an electromagnetic tomographic scanner for use in imaging a human head, including: a base; an imaging chamber, supported on the base, that defines an imaging domain; at least one ring of antennas, supported by the imaging chamber and encircling the imaging domain; a plurality of antenna controllers, each antenna controller including radio frequency (RF) transmitter/receiver circuitry that is connected to an antenna of an imaging chamber of an electromagnetic tomographic scanner, an intermediate frequency (IF) stage that is connected to the RF transceiver transmitter/receiver circuitry, and a baseband (BB) data processing stage that is connected to the intermediate frequency (IF) stage; wherein the baseband (BB) data processing stage produces, as output, data representative of measured electromagnetic field signals received by the antenna.

In a feature of this aspect, the radio frequency (RF) transmitter/receiver circuitry, the intermediate frequency (IF) stage, and the baseband (BB) data processing stage for each respective antenna controller are carried on a dedicated printed circuit board that is separate from the respective printed circuit boards for the other antenna controllers.

Broadly defined, the present invention according to another aspect is an antenna controller, in an electromagnetic tomographic scanner having an imaging chamber, for an antenna arranged around the imaging chamber, including: radio frequency (RF) transmitter/receiver circuitry that is connected to the antenna of the imaging chamber of the electromagnetic tomographic scanner; an intermediate frequency (IF) stage that is connected to the RF transceiver transmitter/receiver circuitry; and a baseband (BB) data processing stage that is connected to the intermediate frequency (IF) stage; wherein the baseband (BB) data processing stage produces, as output, data representative of measured electromagnetic field signals received by the antenna.

In a feature of this aspect, the radio frequency (RF) transmitter/receiver circuitry, the intermediate frequency (IF) stage, and the baseband (BB) data processing stage for the antenna controller are carried on a dedicated printed circuit board that is separate from printed circuit boards for other antenna controllers in the electromagnetic tomographic scanner.

Broadly defined, the present invention according to another aspect is an electromagnetic tomographic system for imaging a human head, including: a base; an imaging chamber, supported on the base, that defines an imaging domain in which a human head is received; a plurality of antennas, arranged in at least one ring, that are supported by the imaging chamber and encircle the imaging domain; a plurality of antenna controllers, each dedicated to a respective antenna in the at least one ring of antennas, wherein each antenna controller includes radio frequency (RF) transceiver circuitry having a transmit side and a receive side that are alternately connected to the antenna using an RF switch; and an image processing computer system communicatively connected to the antenna controllers; wherein while one of the antennas is transmitting an electromagnetic signal into the imaging domain, a plurality of the antennas in the at least one ring of antennas are simultaneously receiving the electromagnetic signal after passing through the imaging domain; wherein, for each of the plurality of antennas simultaneously receiving the electromagnetic signal after passing through the imaging domain, the corresponding antenna controller for the respective antenna is measuring the electromagnetic signal respectively received at such antenna simultaneously with the measurement of the electromagnetic signals received at the other antennas of the plurality of antennas; wherein the respective antenna controller dedicated to each antenna, of the plurality of antennas simultaneously receiving the electromagnetic signal after passing through the imaging domain, provides, as output, data representative of measured electromagnetic field signals received by such antenna; and wherein the image processing computer system receives the data representative of the measured electromagnetic field signals from the plurality of antenna controllers and images the human head from the received data.

In a feature of this aspect, the at least one ring of antennas includes a first ring of antennas and a second ring of antennas. In a further feature, while one of the antennas in the first antenna ring is transmitting an electromagnetic signal into the imaging domain, a plurality of the antennas in both the first and second antenna rings are simultaneously receiving the electromagnetic signal after passing through the imaging domain, and wherein, for each of the plurality of antennas in both the first and second antenna rings that simultaneously receive the electromagnetic signal after passing through the imaging domain, the corresponding antenna controller for the respective antenna is measuring the electromagnetic signal respectively received at such antenna simultaneously with the measurement of the electromagnetic signals received at the other antennas of the plurality of antennas.

In another feature of this aspect, the circuitry of each antenna controller, including the radio frequency (RF) transceiver circuitry, is carried on a printed circuit board. In further features, the circuitry for each respective antenna controller is carried on one or more dedicated printed circuit board that are separate from the respective printed circuit boards for the other antenna controllers; the system further includes a plurality of antenna adapters, wherein each of the plurality of antenna adapters is dedicated to a respective antenna in the ring of antennas, and wherein the antennas and antennas adapters include circuitry that is carried on a dedicated printed circuit board that is separate from the respective printed circuit boards for the other antennas and antenna adapters; the circuitry for each antenna and antenna adapter and the circuitry for the corresponding antenna controller are carried together on a single respective printed circuit board; the circuitry for each antenna and antenna adapter is carried on a first printed circuit board in a first module and the circuitry for the antenna controller corresponding to the antenna and antenna adapter is carried on a second printed circuit board in a second module; each respective first printed circuit board module is connected to its corresponding second printed circuit board module via one or more cable; the second printed circuit boards for all of the antennas are housed together in a location separate from the at least one antenna ring; the plurality of second printed circuit boards are arranged in a ring around the first printed circuit boards such that each respective second printed circuit board is disposed adjacent its corresponding first printed circuit board; the circuitry for each respective antenna controller includes an analog to digital converter (ADC), carried on the one or more dedicated printed circuit board, such that the data representative of measured complex electromagnetic field signals received by the corresponding antenna may be generated; the circuitry for each respective antenna controller includes a digital signal processor carried on the one or more dedicated printed circuit boards; the circuitry for each respective antenna controller utilizes a superheterodyne technology-based architecture; the circuitry for each respective antenna controller includes, in additional to the radio frequency (RF) transceiver circuitry, an intermediate frequency (IF) stage that is connected to the RF transceiver circuitry, and a baseband (BB) data processing stage that is connected to the intermediate frequency (IF) stage; the baseband (BB) data processing stage produces the data, representative of measured electromagnetic field signals received by the antenna, that is provided as output; the intermediate frequency (IF) stage utilizes quadrature modulation to produce an IF signal that includes both in-phase and quadrature components; a common clock oscillator is provided to the intermediate frequency (IF) stage of each of the plurality of antenna controllers; each intermediate frequency (IF) stage includes a frequency synthesizer, utilizing the common clock oscillator as input, that provides a carrier signal of at least 100 MHz for an analog modulation/demodulation process; and/or the carrier signal provided by the frequency synthesizer for the analog modulation/demodulation process, utilizing the common clock oscillator as input, is at least 1 GHz.

In another feature of this aspect, the imaging chamber is cylindrical and includes at least three rings of antennas. In further features, the imaging chamber includes at least five rings of antennas; the imaging chamber includes six rings of antennas; each of the at least three rings of antennas includes a number of antennas that is equal to the number of antennas in each of the other rings.

In another feature of this aspect, the imaging chamber is semispherical and includes at least three rings of antennas; the imaging chamber includes at least six rings of antennas; and/or each of the at least three rings of antennas includes a number of antennas that is different from the number of antennas in each of the other rings.

In another feature of this aspect, the imaging chamber translates relative to the base; the imaging chamber translates horizontally relative to the base; the imaging chamber translates vertically relative to the base; the imaging chamber rotates upward and downward relative to the base.

In another feature of this aspect, the antennas are waveguide antennas.

In another feature of this aspect, the antennas are slot antennas.

In another feature of this aspect, the image processing computer system is integrated with the electromagnetic tomographic scanner.

In another feature of this aspect, the image processing computer system is disposed in the same room as the electromagnetic tomographic scanner.

In another feature of this aspect, the image processing computer system is disposed in a room that is different from a room in which the electromagnetic tomographic scanner is disposed.

Broadly defined, the present invention according to another aspect is an electromagnetic tomographic scanner for use in imaging a human head, including: a base; an imaging chamber, supported on the base, that defines an imaging domain in which a human head is received; a plurality of antennas, arranged in at least one ring, that are supported by the imaging chamber and encircle the imaging domain; and a plurality of antenna controllers, each dedicated to a respective antenna in the at least one ring of antennas, wherein each antenna controller includes radio frequency (RF) transceiver circuitry having a transmit side and a receive side that are alternately connected to the antenna using an RF switch; wherein while one of the antennas is transmitting an electromagnetic signal into the imaging domain, a plurality of the antennas in the at least one ring of antennas are simultaneously receiving the electromagnetic signal after passing through the imaging domain; wherein, for each of the plurality of antennas simultaneously receiving the electromagnetic signal after passing through the imaging domain, the corresponding antenna controller for the respective antenna is measuring the electromagnetic signal respectively received at such antenna simultaneously with the measurement of the electromagnetic signals received at the other antennas of the plurality of antennas; and wherein the respective antenna controller dedicated to each antenna, of the plurality of antennas simultaneously receiving the electromagnetic signal after passing through the imaging domain, provides, as output, data representative of measured electromagnetic field signals received by such antenna.

In a feature of this aspect, the at least one ring of antennas includes a first ring of antennas and a second ring of antennas. In a further feature, while one of the antennas in the first antenna ring is transmitting an electromagnetic signal into the imaging domain, a plurality of the antennas in both the first and second antenna rings are simultaneously receiving the electromagnetic signal after passing through the imaging domain, and wherein, for each of the plurality of antennas in both the first and second antenna rings that simultaneously receive the electromagnetic signal after passing through the imaging domain, the corresponding antenna controller for the respective antenna is measuring the electromagnetic signal respectively received at such antenna simultaneously with the measurement of the electromagnetic signals received at the other antennas of the plurality of antennas.

In another feature of this aspect, the circuitry of each antenna controller, including the radio frequency (RF) transceiver circuitry, is carried on a printed circuit board. In further features, the circuitry for each respective antenna controller is carried on one or more dedicated printed circuit board that are separate from the respective printed circuit boards for the other antenna controllers; the scanner further includes a plurality of antenna adapters, wherein each of the plurality of antenna adapters is dedicated to a respective antenna in the ring of antennas, and wherein the antennas and antennas adapters include circuitry that is carried on a dedicated printed circuit board that is separate from the respective printed circuit boards for the other antennas and antenna adapters; the circuitry for each antenna and antenna adapter and the circuitry for the corresponding antenna controller are carried together on a single respective printed circuit board; the circuitry for each antenna and antenna adapter is carried on a first printed circuit board in a first module and the circuitry for the antenna controller corresponding to the antenna and antenna adapter is carried on a second printed circuit board in a second module; each respective first printed circuit board module is connected to its corresponding second printed circuit board module via one or more cable; the second printed circuit boards for all of the antennas are housed together in a location separate from the at least one antenna ring; the plurality of second printed circuit boards are arranged in a ring around the first printed circuit boards such that each respective second printed circuit board is disposed adjacent its corresponding first printed circuit board; the circuitry for each respective antenna controller includes an analog to digital converter (ADC), carried on the one or more dedicated printed circuit board, such that the data representative of measured complex electromagnetic field signals received by the corresponding antenna may be generated; the circuitry for each respective antenna controller includes a digital signal processor carried on the one or more dedicated printed circuit boards; the circuitry for each respective antenna controller utilizes a superheterodyne technology-based architecture; the circuitry for each respective antenna controller includes, in additional to the radio frequency (RF) transceiver circuitry, an intermediate frequency (IF) stage that is connected to the RF transceiver circuitry, and a baseband (BB) data processing stage that is connected to the intermediate frequency (IF) stage; the baseband (BB) data processing stage produces the data, representative of measured electromagnetic field signals received by the antenna, that is provided as output; the intermediate frequency (IF) stage utilizes quadrature modulation to produce an IF signal that includes both in-phase and quadrature components; a common clock oscillator is provided to the intermediate frequency (IF) stage of each of the plurality of antenna controllers; each intermediate frequency (IF) stage includes a frequency synthesizer, utilizing the common clock oscillator as input, that provides a carrier signal of at least 100 MHz for an analog modulation/demodulation process; and/or the carrier signal provided by the frequency synthesizer for the analog modulation/demodulation process, utilizing the common clock oscillator as input, is at least 1 GHz.

In another feature of this aspect, the imaging chamber is cylindrical and includes at least three rings of antennas. In further features, the imaging chamber includes at least five rings of antennas; the imaging chamber includes six rings of antennas; and/or each of the at least three rings of antennas includes a number of antennas that is equal to the number of antennas in each of the other rings.

In another feature of this aspect, the imaging chamber is semispherical and includes at least three rings of antennas. In further features, the imaging chamber includes at least six rings of antennas; and/or each of the at least three rings of antennas includes a number of antennas that is different from the number of antennas in each of the other rings.

In another feature of this aspect, the imaging chamber translates relative to the base. In further features, the imaging chamber translates horizontally relative to the base; the imaging chamber translates vertically relative to the base; and/or the imaging chamber rotates upward and downward relative to the base.

In another feature of this aspect, the antennas are waveguide antennas.

In another feature of this aspect, the antennas are slot antennas.

Broadly defined, the present invention according to another aspect is a method of conducting electromagnetic tomography for imaging a human head, including: positioning a human head through an opening in an end of an imaging chamber of an electromagnetic tomographic scanner, wherein the imaging chamber defines an imaging domain such that at least a portion of the brain is in the imaging domain, wherein the imaging chamber supports at least one ring of antennas that encircles the imaging domain, and wherein each antenna has a dedicated antenna controller that includes radio frequency (RF) transceiver circuitry having a transmit side and a receive side that are alternately connected to the antenna using an RF switch; controlling one antenna, via the antenna's corresponding antenna controller, to transmit an electromagnetic signal into the imaging domain; controlling a plurality of the antennas, via each respective antenna's antenna controller, to receive the electromagnetic signal after passing through the imaging domain such that all of the antennas of the plurality of antennas are receiving the electromagnetic signals simultaneously; for each of the plurality of receiving antennas, measuring the respective received electromagnetic signal such that all of the simultaneously received electromagnetic signals are measured simultaneously; for each of the plurality of receiving antennas, outputting data representative of the measured electromagnetic field signals received by such antenna; receiving the data at an image processing computer; and carrying out an electromagnetic tomography image reconstruction process at the image processing center to produce an image of the brain.

In a feature of this aspect, the at least one ring of antennas includes a first ring of antennas and a second ring of antennas. In a further feature, the step of controlling a plurality of the antennas, via each respective antenna's antenna controller, to receive the electromagnetic signal after passing through the imaging domain includes controlling a plurality of the antennas in both the first and second antenna rings, via each respective antenna's antenna controller, to receive the electromagnetic signal after passing through the imaging domain such that all of the antennas of the plurality of antennas are receiving the electromagnetic signals simultaneously.

In another feature of this aspect, the circuitry of each antenna controller, including the radio frequency (RF) transceiver circuitry, is carried on a printed circuit board. In further features, the circuitry for each respective antenna controller is carried on one or more dedicated printed circuit board that are separate from the respective printed circuit boards for the other antenna controllers; the method further includes a plurality of antenna adapters, wherein each of the plurality of antenna adapters is dedicated to a respective antenna in the ring of antennas, and wherein the antennas and antennas adapters include circuitry that is carried on a dedicated printed circuit board that is separate from the respective printed circuit boards for the other antennas and antenna adapters; the circuitry for each antenna and antenna adapter and the circuitry for the corresponding antenna controller are carried together on a single respective printed circuit board; the circuitry for each antenna and antenna adapter is carried on a first printed circuit board in a first module and the circuitry for the antenna controller corresponding to the antenna and antenna adapter is carried on a second printed circuit board in a second module; each respective first printed circuit board module is connected to its corresponding second printed circuit board module via one or more cable; the second printed circuit boards for all of the antennas are housed together in a location separate from the at least one antenna ring; the plurality of second printed circuit boards are arranged in a ring around the first printed circuit boards such that each respective second printed circuit board is disposed adjacent its corresponding first printed circuit board; the circuitry for each respective antenna controller includes an analog to digital converter (ADC), carried on the one or more dedicated printed circuit board, such that the data representative of measured complex electromagnetic field signals received by the corresponding antenna may be generated; the circuitry for each respective antenna controller includes a digital signal processor carried on the one or more dedicated printed circuit boards; the circuitry for each respective antenna controller utilizes a superheterodyne technology-based architecture; the circuitry for each respective antenna controller includes, in additional to the radio frequency (RF) transceiver circuitry, an intermediate frequency (IF) stage that is connected to the RF transceiver circuitry, and a baseband (BB) data processing stage that is connected to the intermediate frequency (IF) stage; the method further includes a step of producing, via the baseband (BB) data processing stage produces, the data, representative of measured electromagnetic field signals received by the antenna, that is provided as output; the method further includes a step of utilizing quadrature modulation, by the intermediate frequency (IF) stage, to produce an IF signal that includes both in-phase and quadrature components; the method further includes a step of providing a common clock oscillator to the intermediate frequency (IF) stage of each of the plurality of antenna controllers; each intermediate frequency (IF) stage includes a frequency synthesizer, utilizing the common clock oscillator as input, that provides a carrier signal of at least 100 MHz for an analog modulation/demodulation process; and/or the carrier signal provided by the frequency synthesizer for the analog modulation/demodulation process, utilizing the common clock oscillator as input, is at least 1 GHz.

In another feature of this aspect, the imaging chamber is cylindrical and includes at least three rings of antennas; the imaging chamber includes at least five rings of antennas; the imaging chamber includes six rings of antennas; and/or each of the at least three rings of antennas includes a number of antennas that is equal to the number of antennas in each of the other rings.

In another feature of this aspect, the imaging chamber is semispherical and includes at least three rings of antennas. In further features, the imaging chamber includes at least six rings of antennas; and/or each of the at least three rings of antennas includes a number of antennas that is different from the number of antennas in each of the other rings.

In another feature of this aspect, the imaging chamber translates relative to the base. In further features, the method further includes a step of translating the imaging chamber horizontally, relative to the base, to position the imaging chamber relative to the human head; the method further includes a step of translating the imaging chamber vertically, relative to the base, to position the imaging chamber relative to the human head; and/or the method further includes a step of rotating upward and downward, relative to the base, to position the imaging chamber relative to the human head.

In another feature of this aspect, the antennas are waveguide antennas.

In another feature of this aspect, the antennas are slot antennas.

In another feature of this aspect, the image processing computer system is integrated with the electromagnetic tomographic scanner.

In another feature of this aspect, the image processing computer system is disposed in the same room as the electromagnetic tomographic scanner.

In another feature of this aspect, the image processing computer system is disposed in a room that is different from a room in which the electromagnetic tomographic scanner is disposed.

Broadly defined, the present invention according to another aspect is an electromagnetic tomographic scanner for use in imaging a live human body part, including: an imaging chamber, supported on a base, that defines an imaging domain in which at least a portion of a live human body part is received, wherein the imaging chamber has an open end that may be covered by a lid; a plurality of antennas, arranged in at least one ring, that are supported by the imaging chamber and encircle the imaging domain, wherein the antennas are controllable to receive a transmitted electromagnetic signal after passing through the imaging domain; a controller for controlling one or more of the plurality of antennas; a lid that is attachable to the open end of the imaging chamber, wherein the lid includes a hollow boundary model that mimics the anatomy of a portion of the human, extending away from the imaging domain of the imaging chamber, and wherein the portion of the human whose anatomy is mimicked is the portion of the human that is expected to be disposed outside of the imaging domain when the portion of the live human body part is received in the imaging domain; and a quantity of a matching media, the matching media filling an interior of the hollow boundary model while an empty field measurement is carried out via the at least one ring of antennas.

In a feature of this aspect, the hollow boundary model mimics the anatomy of a portion of the head of the human. In further features, the hollow boundary model mimics the anatomy of a lower portion of the human head; the lid includes a frame having a central opening that is surrounded by the hollow boundary model such that when the lid is attached to the open end of the imaging chamber, the interior of the hollow boundary model is in fluid communication with the imaging domain; the central opening is ellipsoidal; the frame is rigid; the lid is a full lid and wherein the hollow boundary model defines a separate interior cavity, not in fluid communication with the imaging domain, that is filled by the matching media; the matching media is a liquid; the lid is temporarily sealed to the open end of the imaging chamber while the empty field measurement is carried out; the matching media is a liquid, and wherein the temporary seal between the lid and the open end of the imaging chamber prevents leakage of the matching media from between the imaging chamber and the lid; the matching media is a gel; the lid is attached, but not necessarily sealed, to the open end of the imaging chamber while the empty field measurement is carried out, and wherein the consistency of the gel prevents leakage from between the imaging chamber and the lid; the imaging chamber is at least partially tilted, while the empty field measurement is carried out, such that matching media is caused to flow into the interior of the hollow boundary model; and/or the imaging chamber is adjustable during use from a vertical orientation, wherein the open end of the imaging chamber faces upward, to a horizontal orientation, wherein the open end of the imaging chamber faces sideward.

Broadly defined, the present invention according to another aspect is a method of conducting electromagnetic tomography for imaging a human head, including: providing an imaging chamber, supported on a base, that defines an imaging domain in which at least a portion of a live human body part may be received, wherein the imaging chamber has an open end, wherein the imaging chamber supports a plurality of antennas, arranged in at least one ring, that encircle the imaging domain, and wherein each antenna may be controlled by a controller; temporarily attaching a lid to the open end of the imaging chamber, wherein the lid includes a hollow boundary model that mimics the anatomy of a portion of the human, extending away from the imaging domain of the imaging chamber, and wherein the portion of the human whose anatomy is mimicked is the portion of the human that is expected to be disposed outside of the imaging domain when the human's head is received in the imaging domain; filling an interior of the hollow boundary model with a matching media; without the human in the imaging domain, carrying out a process of empty field measurement by transmitting electromagnetic signals and receiving them, after passing through the imaging domain, at each of a plurality of the antennas in the at least one ring; with the lid in a removed state, positioning at least a portion of a live human body part through the opening in the end of the imaging chamber, and, subsequently, carrying out a process of full field measurement by transmitting electromagnetic signals and receiving them, after passing through the imaging domain, at each of a plurality of the antennas in the at least one ring; and carrying out an electromagnetic tomography image reconstruction process using both the empty field measurements and the full field measurements.

In a feature of this aspect, the hollow boundary model mimics the anatomy of a portion of the head of the human. In further features, the method further includes a step of filling the imaging domain of the imaging chamber with a further quantity of the matching media, and wherein the imaging domain of the imaging chamber contains the matching media during both the empty field measurement process and the full field measurement process; the hollow boundary model is a closed cavity that is not in fluid communication with the imaging domain of the imaging chamber; the hollow boundary model is open such that the interior of the hollow boundary model is in fluid communication with the imaging domain of the imaging chamber when the lid is temporarily attached to the open end of the imaging chamber; the hollow boundary model mimics the anatomy of a lower portion of the human head; the lid includes a frame having a central opening that is surrounded by the hollow boundary model, and wherein the step of temporarily attaching a lid to the open end of the imaging chamber includes attaching the lid such that the interior of the hollow boundary model is in fluid communication with the imaging domain; the central opening is ellipsoidal; the frame is rigid; the lid is a full lid, wherein the hollow boundary model defines a separate interior cavity, wherein filling an interior of the hollow boundary model with a matching media includes filling the separate interior cavity with a matching media, and wherein the step of temporarily attaching a lid to the open end of the imaging chamber includes attaching the lid such that the separate interior cavity of the hollow boundary model is not in fluid communication with the imaging domain; the matching media is a liquid; the step of temporarily attaching a lid to the open end of the imaging chamber includes temporarily sealing the lid to the open end of the imaging chamber, and wherein the step of carrying out a process of empty field measurement is carried out while the lid is temporarily sealed to the open end of the imaging chamber; the matching media is a liquid, and wherein the temporary seal between the lid and the open end of the imaging chamber prevents leakage of the matching media from between the imaging chamber and the lid; the matching media is a gel; the lid is attached, but not necessarily sealed, to the open end of the imaging chamber while the empty field measurement is carried out, and wherein the consistency of the gel prevents leakage from between the imaging chamber and the lid; the method further includes a step of tilting the imaging chamber such that matching media is caused to flow into the interior of the hollow boundary model, and wherein the step of carrying out a process of empty field measurement is carried out while the imaging chamber is at least partially tilted; and/or the method further includes a step of adjusting the imaging chamber, during use, from a vertical orientation, wherein the open end of the imaging chamber faces upward, to a horizontal orientation, wherein the open end of the imaging chamber faces sideward.

Broadly defined, the present invention according to another aspect is a method of conducting electromagnetic tomography for imaging a human head, including: providing an imaging chamber, supported on a base, that defines an imaging domain in which at least a portion of a human head may be received, wherein the imaging chamber has an open end, wherein the imaging chamber supports at least one ring of antennas that encircles the imaging domain, and wherein each antenna may be controlled by a controller; without the human in the imaging domain, carrying out a process of empty field measurement by transmitting electromagnetic signals from respective antennas and receiving them, after passing through the imaging domain, at each of a plurality of the antennas in the at least one ring; storing the empty field measurements; producing a first tensor, represented by $S_{i,j}^{meas,empty}$, corresponding to the measured empty field for each pair of transmitting and receiving antennas i,j; positioning a human head through the opening in the end of the imaging chamber; with the head of the human positioned through the open end of the imaging chamber such that at least a portion of the human's brain is disposed in the imaging domain, carrying out a process of full field measurement by transmitting electromagnetic signals from respective antennas and receiving them, after passing through the imaging domain, at each of a plurality of the antennas in the at least one ring, wherein the measurements; producing a second tensor, represented by $S_{i,j}^{meas,full}$, corresponding to the measured full field for each pair of transmitting and receiving antennas i,j; producing a third tensor, represented by $S_{i,j,k}^{meas,sct}$, corresponding to the scattering caused by the human's head, via the algebraic subtraction $S_{i,j,k}^{meas,sct} = S_{i,j,k}^{meas,full} - S_{i,j,k}^{meas,empty}$; using at least the first, second, and third tensors, carrying out an iterative process involving the solving of a direct problem, the solving of an inverse problem, the calculation of updated dielectric permittivity values corresponding to the human's brain in the imaging domain, and the computation of a functional that is evaluated for convergence to predetermined criteria, wherein an antenna-by-antenna normalization is utilized in the functional such that $$S_{ij} \equiv \frac{S_{ij}^{sct}}{S_{ij}^{empty}};$$

and when convergence is achieved, producing a reconstructed image of a portion of the human's brain by plotting a final dielectric permittivity distribution.

In a feature of this aspect, the method further includes a step of formulating a matching media to have a dielectric permittivity of ($\epsilon=\epsilon'+j\epsilon''$) such that $\epsilon'$ is in the range of about 40 to 45 and $\epsilon''$ is in the range of about 17 to 21, wherein the electromagnetic tomography system includes an electromagnetic tomographic scanner and an image processing computer system, and wherein the electromagnetic tomographic scanner includes an imaging chamber, supported on a base, that includes an open end and that defines an imaging domain; the method further comprises at least partially filling the imaging chamber with the matching media; and the step of carrying out a process of full field measurement with the head of the human positioned through the open end of the imaging chamber is executed with the imaging chamber at least partially filled with the matching media. In further features, the step of formulating a matching media includes formulating a matching media that is a fluid; the step of formulating a matching media includes formulating a matching media that is a gel; the step of formulating a matching media includes formulating a matching media that includes glycerol and water; the step of formulating a matching media includes formulating a matching media that further includes brine; the step of formulating a matching media includes formulating a matching media that includes brine and water; the method further includes steps of, first, rotating the imaging chamber, relative to the base, until the open end of the imaging chamber is oriented to face upward so as to receive and retain the matching media; and then, rotating the imaging chamber, relative to the base, until the open end of the imaging chamber is oriented to face sideways so as to receive the human head, while the head is horizontally oriented, and remains in the sideways orientation during the step of conducting the full field measurement; the method further includes a step of carrying out a calibration process for the system while the imaging chamber is oriented to face upward so as to retain the matching media; the calibration process includes use of an equalization technique to adjust for variations between receivers of the plurality of receivers; the calibration process includes temporarily positioning a reference antenna in the imaging chamber and conducting electromagnetic field measurements via the reference antenna; and/or the method further includes a step of measuring the empty field in the imaging domain is measured while the imaging chamber is oriented to face upward so as to retain the matching media.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Further features, embodiments, and advantages of the present invention will become apparent from the following detailed description with reference to the drawings, wherein:

FIGS. 25A and 24B are graphical representations (rendered in a black-and-white version and a color version) of an image reconstruction, for the same object as that of FIGS. 24A and 24B but using antenna-by-antenna normalization at early iterations.

DETAILED DESCRIPTION

Figure 1:
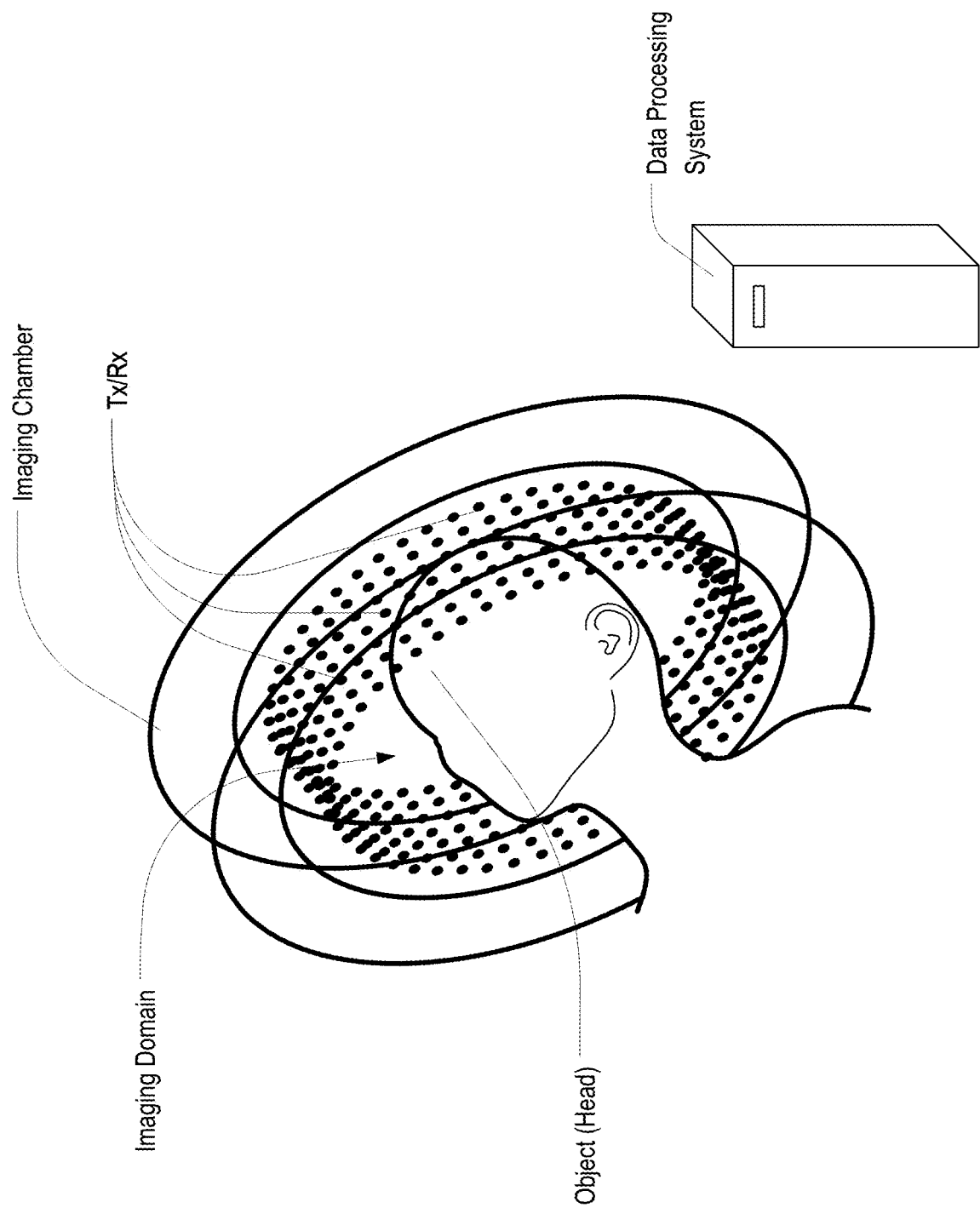
FIG. 1 is a simplified schematic illustration of portions of an electromagnetic tomography (EMT) system.

As a preliminary matter, it will readily be understood by one having ordinary skill in the relevant art ("Ordinary Artisan") that the present invention has broad utility and application. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. § 112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers," "a picnic basket having crackers without cheese," and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, in which like numerals represent like components throughout the several views, one or more preferred embodiments of the present invention are next described. The following description of one or more preferred embodiment(s) is merely exemplary in nature and is in no way intended to limit the invention, its application, or uses.

Figure 2:
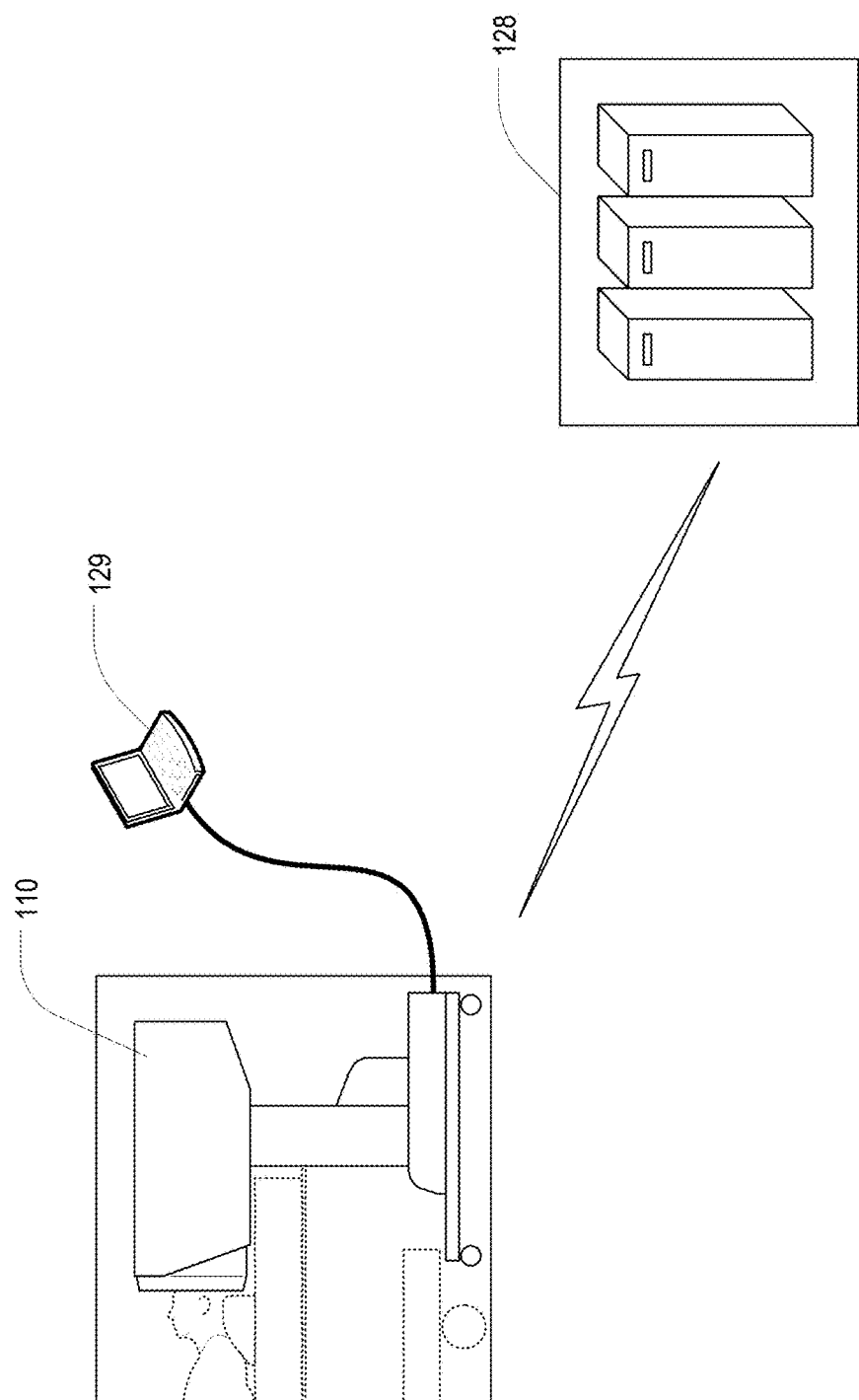
FIG. 2 is a block diagram of an electromagnetic tomography (EMT) system in accordance with one or more preferred embodiments of the present invention.

FIG. 2 is a block diagram of an electromagnetic tomography (EMT) system 100 in accordance with one or more preferred embodiments of the present invention. As shown therein, the EMT system 100 includes an electromagnetic tomographic scanner 110, a local initial image validation computer 129 which might be integrated within the system or stand-alone, and a remote image processing computer system 128. The local computer 129, which in at least some embodiments is located in the same room as the electromagnetic tomographic scanner 110 or integrated within the scanner 110, may be connected to the electromagnetic tomographic scanner 110 via wired connection or wirelessly. In various embodiments, the remote image processing computer system 128 is located elsewhere in the same facility (e.g., same hospital) as the electromagnetic tomographic scanner 110, at the (external) premises of the electromagnetic tomographic scanner supplier, at the (external) premises of a third party Image Processing Center (IPC), or other location.

Figure 3:
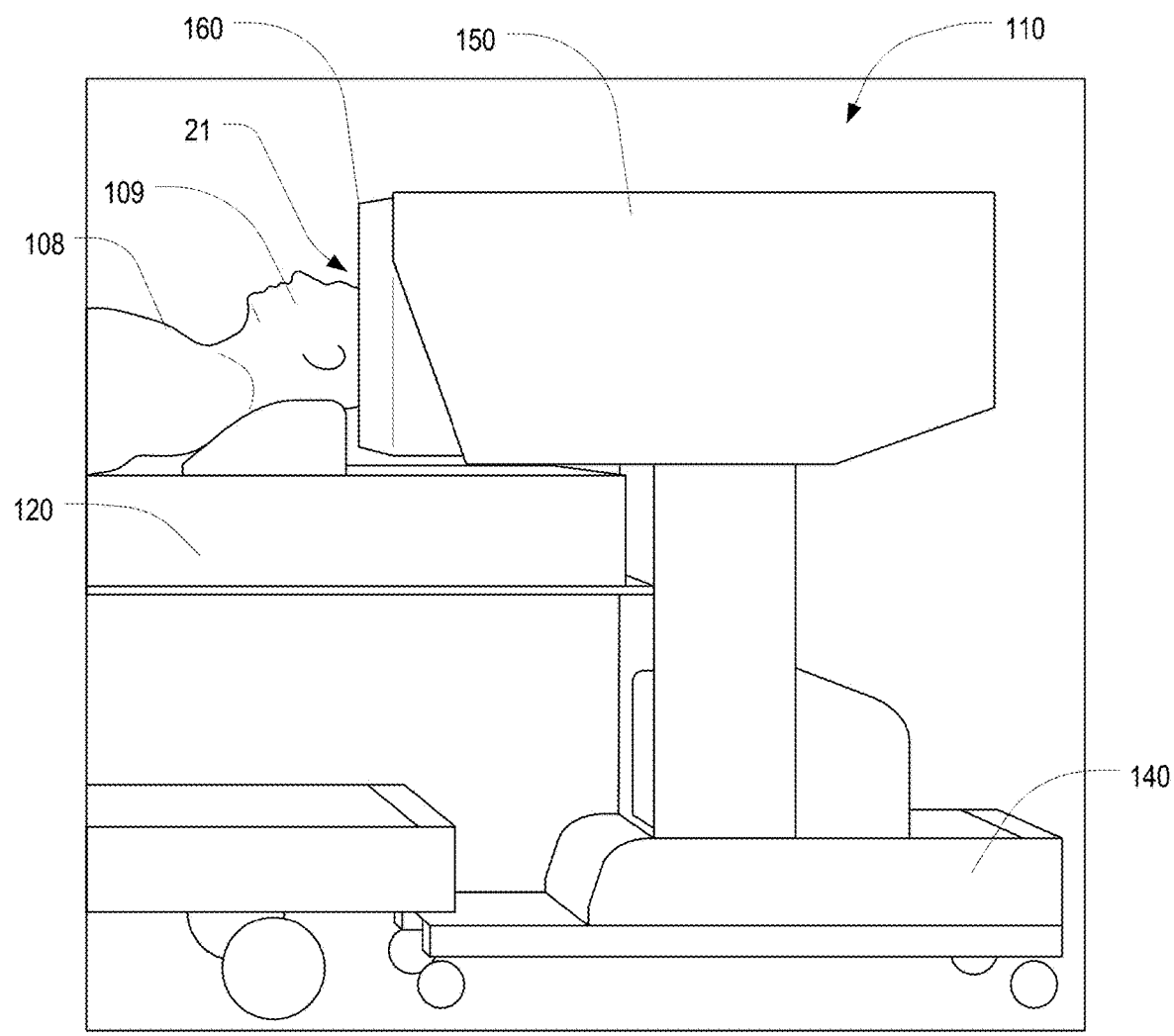
FIG. 3 is a side view of the electromagnetic tomographic scanner of FIG. 2.

FIG. 3 is a side view of the electromagnetic tomographic scanner 110 of FIG. 2. As shown therein, the electromagnetic tomographic scanner 110 is located at the end of a bed 120 on which a human patient 108 is lying. The scanner 110 includes a base 140, which in at least some embodiments may be rolled from one location to another, and an imaging chamber system 150, including an imaging chamber 160 defining an imaging domain 21. The imaging chamber 160 is preferably provided with a padded opening 161 that may, for example, be manufactured from a soft foam with a smooth surface. The imaging chamber 160 is capable of translating relative to the base in at least one direction, angle, or the like. Preferably, the imaging chamber 160 is capable of moving horizontally, toward and away from the top of the patient's head 109, a distance of up to 30-40 cm. The patient 108, the bed 120, and/or the scanner 110 are maneuvered such that the patient's head 109 is positioned in the imaging chamber 160.

Figure 4B:
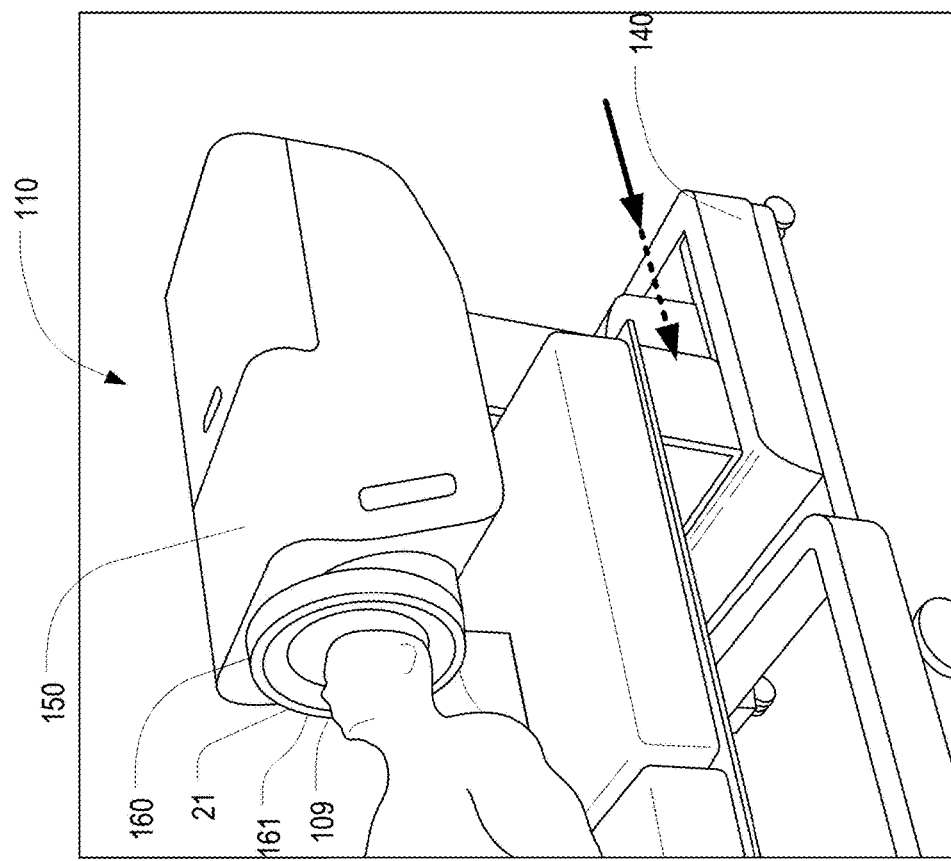
FIG. 4B is a perspective view of the scanner of FIG. 4A shown with the head positioned in the imaging domain of the imaging chamber in preparation for imaging.
Figure 4A:
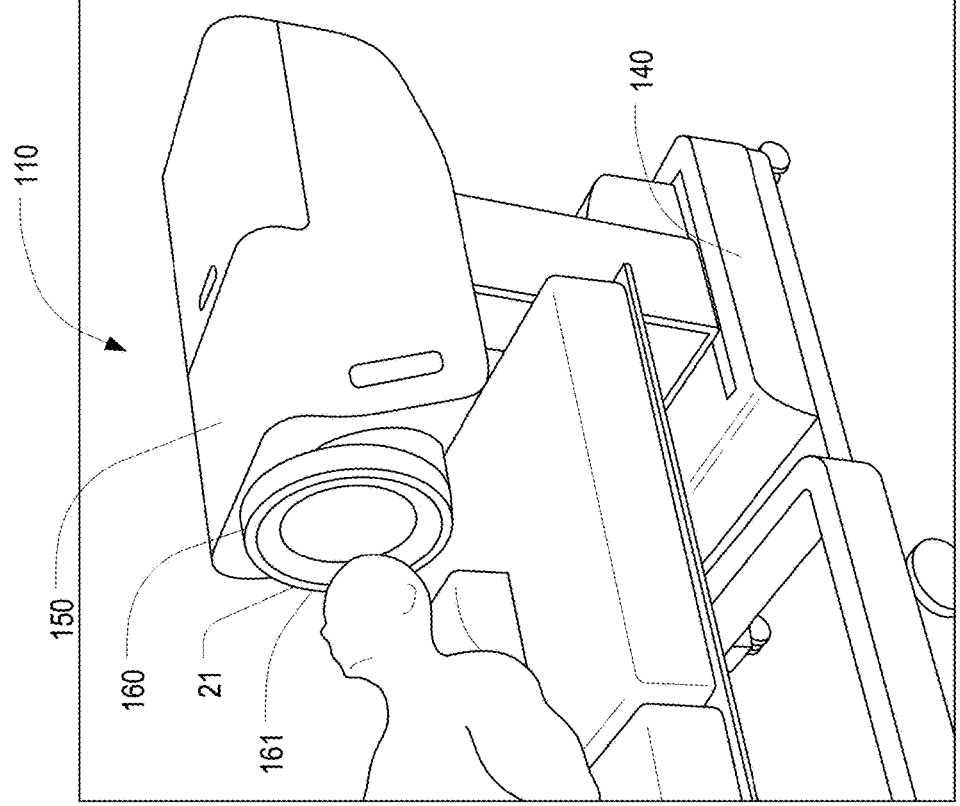
FIG. 4A is a perspective view of the electromagnetic tomographic scanner for head imaging of FIG. 3.

FIG. 4A is a perspective view of the electromagnetic tomographic scanner 110 for head imaging of FIG. 3, and FIG. 4B is a perspective view of the scanner 110 of FIG. 4A shown with the head 109 positioned in the imaging domain 21 of the imaging chamber 160 in preparation for imaging. In at least some embodiments, the computer system 128 and its data processing functionality and imaging software is directly connected to the scanner 110, while in other embodiments some or all of the computer system 128 is remotely connected through wireless technology and/or high speed wire connections. Functionally, much of the operation of the EMT system 100 may be similar to that described in the aforementioned U.S. Pat. No. 9,414,749 but various particular embodiments and features may be described herein.

Figure 5:
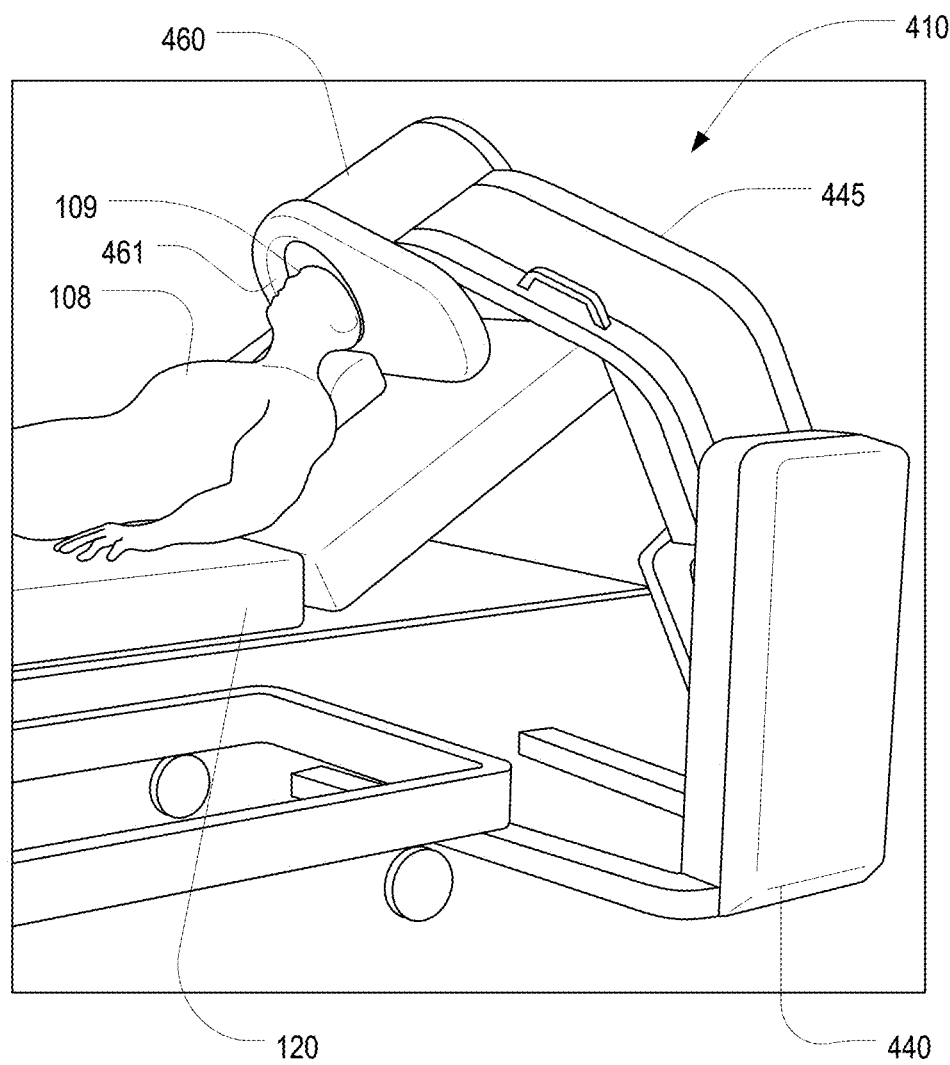
FIG. 5 is a perspective view of a first alternative electromagnetic tomographic scanner for use in the EMT system of FIG. 2.
Figure 6B:
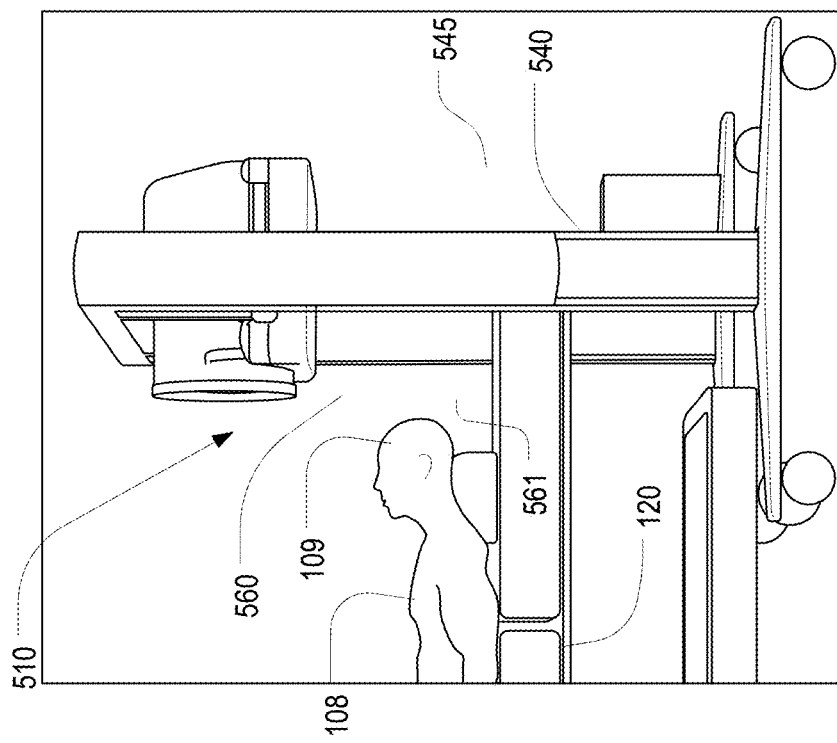
FIGS. 6A and 6B are side views of a second alternative electromagnetic tomographic scanner for use in the EMT system of FIG. 2.
Figure 6A:
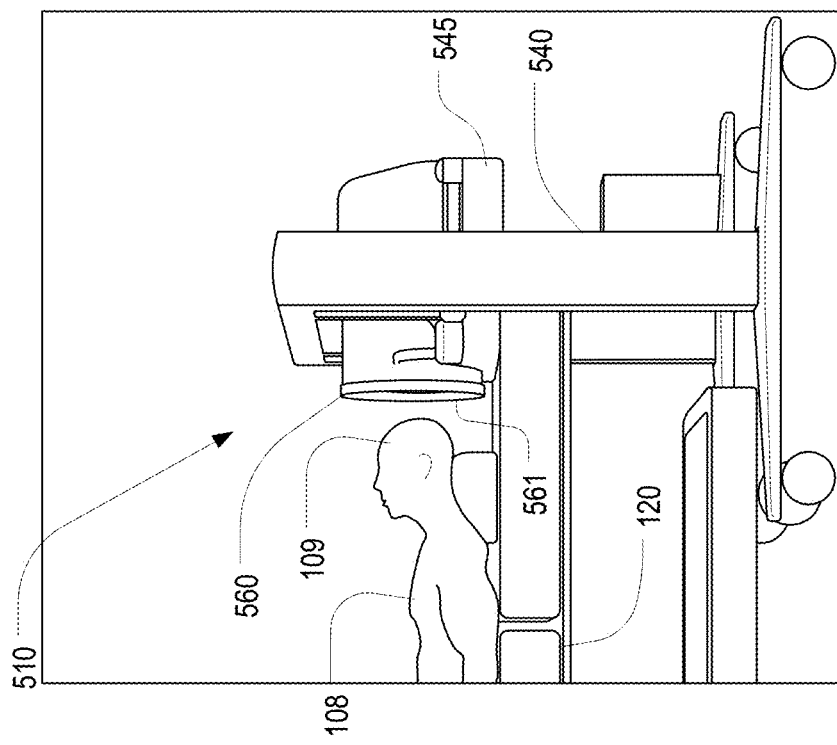

It will be appreciated that in various embodiments, the electromagnetic tomographic scanner may take various forms. In this regard, FIG. 5 is a perspective view of a first alternative electromagnetic tomographic scanner 410 for use in the EMT system 100 of FIG. 2, and FIGS. 6A and 6B are side views of a second alternative electromagnetic tomographic scanner 510 for use in the EMT system 100 of FIG. 2. In the scanner 410 of FIG. 5, an imaging chamber 460, having a padded opening 461, is disposed at the upper end of an arm 445 that rotates with respect to a wheel-mounted base 440 about a horizontal axis. This scanner 410 may be rolled from the side into position at the head of a bed 120, and the imaging chamber 460 may be rotated downward to match the orientation of a patient 108 who is propped up in the bed 120 such that his head 109 is oriented at an angle of approximately 30 degrees (although other angles are likewise possible). In the scanner 510 of FIGS. 6A and 6B, an imaging chamber 560, having a padded opening 561, is arranged to translate horizontally a distance of up to 15-20 cm relative to a carriage 545 that itself can be translated vertically on a wheel-mounted base 540. This scanner 510 may be rolled into position at the head of a bed 120, and the imaging chamber 560 may be adjusted vertically and horizontally to match the position of a patient 108 who is lying generally flat on the bed 120 such that his head 109 is positioned near the head of the bed 120.

Figure 7:
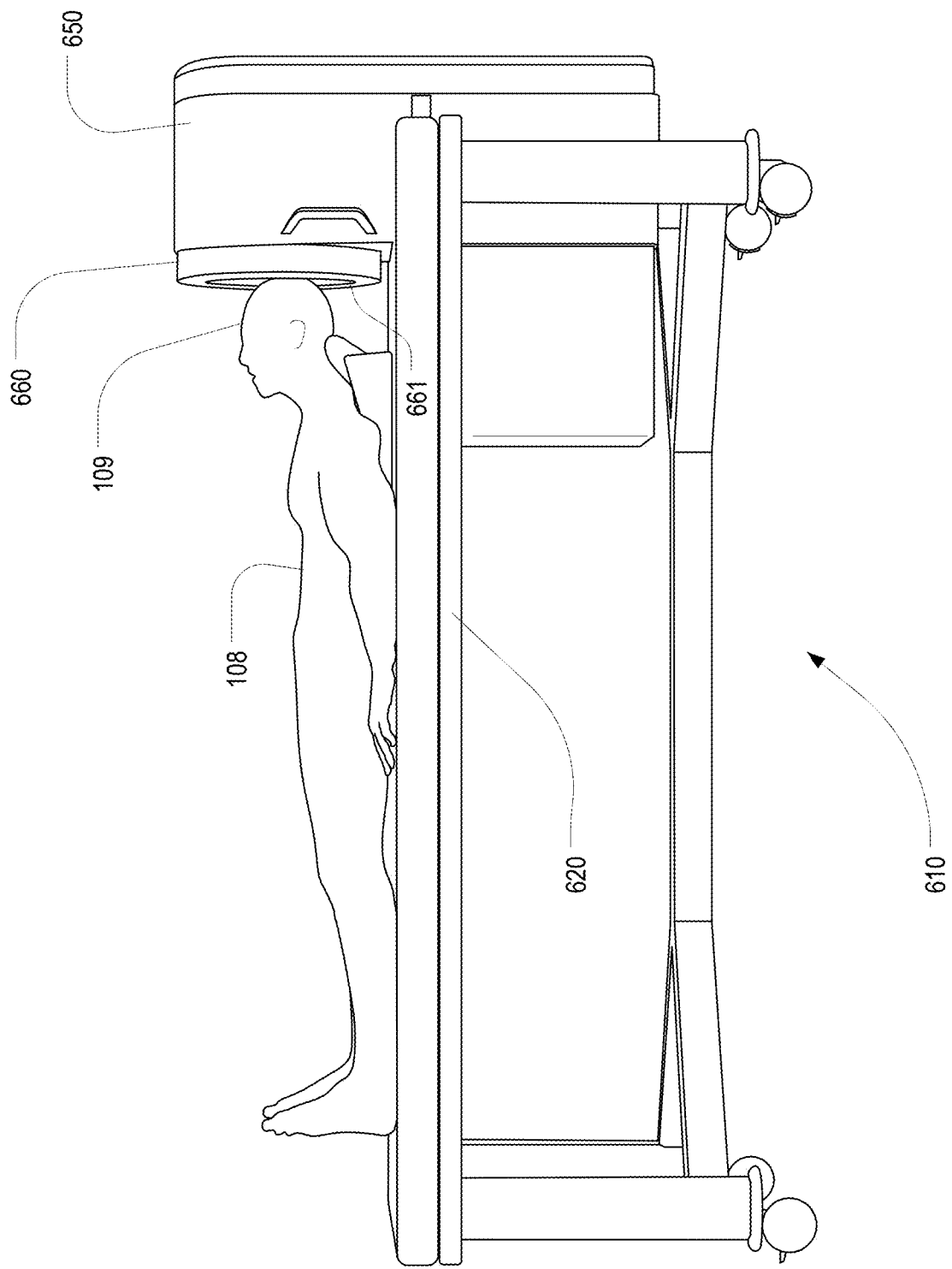
FIG. 7 is a side view of a third alternative electromagnetic tomographic scanner for use in the EMT system of FIG. 2.

In yet further embodiments, a bed may be incorporated into an electromagnetic tomographic scanner. In this regard, FIG. 7 is a side view of a third alternative electromagnetic tomographic scanner 610 for use in the EMT system 100 of FIG. 2. In this scanner 610, an imaging chamber system 650, including an imaging chamber 660 having a padded opening 661, is carried by an integrated bed 620. The imaging chamber 660 preferably translates horizontally a distance of up to 30-40 cm toward and away from the head 109 of the patient 108.

Although the various electromagnetic tomographic scanners described herein 110,410,510,610 take different forms from one another, each scanner provides the ability to position a base, which is generally but not necessarily always supported on wheels, near a patient 108, supported on a bed, and then repositioning a movable portion, including an imaging chamber, relative to the patient's head such that it surrounds the portion of the patient's head 109 to be imaged without the patient 108 being required to move. Furthermore, the movable portion of the scanner includes not only the imaging chamber but the electronics, as described further herein, such that the electronics move with the imaging chamber relative to the base. The movement may be linear (vertical, horizontal, or in some cases at a non-vertical/non-horizontal angle), radial, or both. In some embodiments, movement is preferably effectuated manually, so as to provide more immediate control by an operator, but in at least some embodiments some measure of automated control (such as may be applied via a foot pedal) may be provided. In at least some embodiments, the location and/or orientation of the imaging chamber may be locked into place once positioned as desired. Such scanners may be physically located in hospital environments (e.g., emergency department, intensive care units (ICUs), specialized stroke units, or the like) or, in some embodiments, in other locations (e.g, an ambulance). It will be appreciated that a single hospital or other facility may make use of multiple scanners, and that such scanners may or may not be of different types, but that a plurality of scanners may be supported by a single image processing computer system 128 that is typically located remotely from some or all of the scanners. For the sake of simplicity, however, only a single scanner 110 of the type shown in FIG. 3 is generally referenced in the following description.

As described above, EMT imaging of high dielectric contrast objects, including biological objects, involves the very complicated problem of so-called "diffraction tomography." A high dielectric contrast between tissues with high water content, such as but not limited to muscle tissue, and low water content, such as but not limited to bone, presents an additional complication when using EM fields for imaging. Specialized hardware in the scanner 110 and image reconstruction methods 3100 are preferably utilized to solve the so-called "diffraction tomography" problem.

Figure 8B:
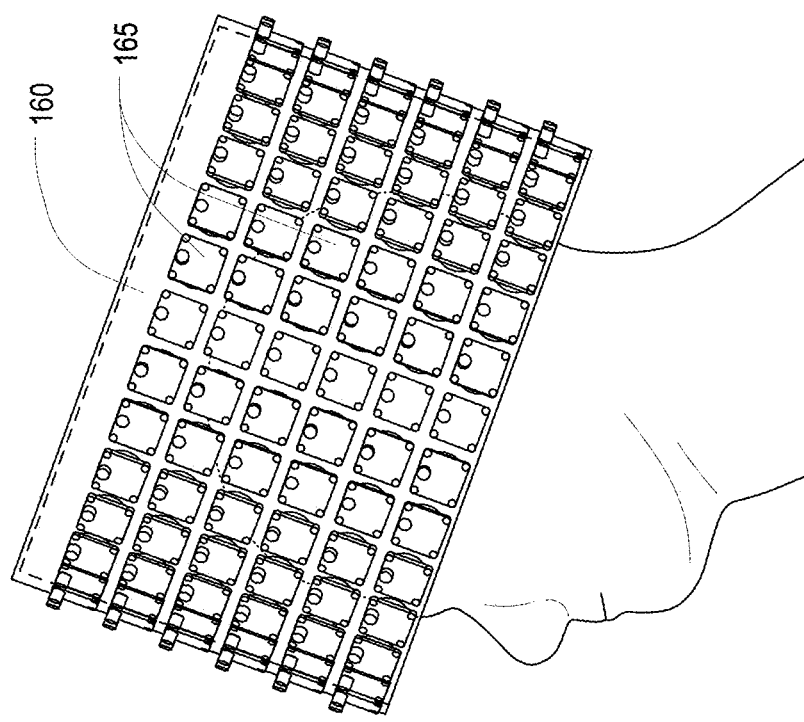
FIGS. 8A and 8B are side views of a cylindrical electromagnetic tomography (EMT) imaging chamber, shown without and with antennas installed therein, for use in the imaging chamber system in accordance with one or more preferred embodiments of the present invention.
Figure 8A:
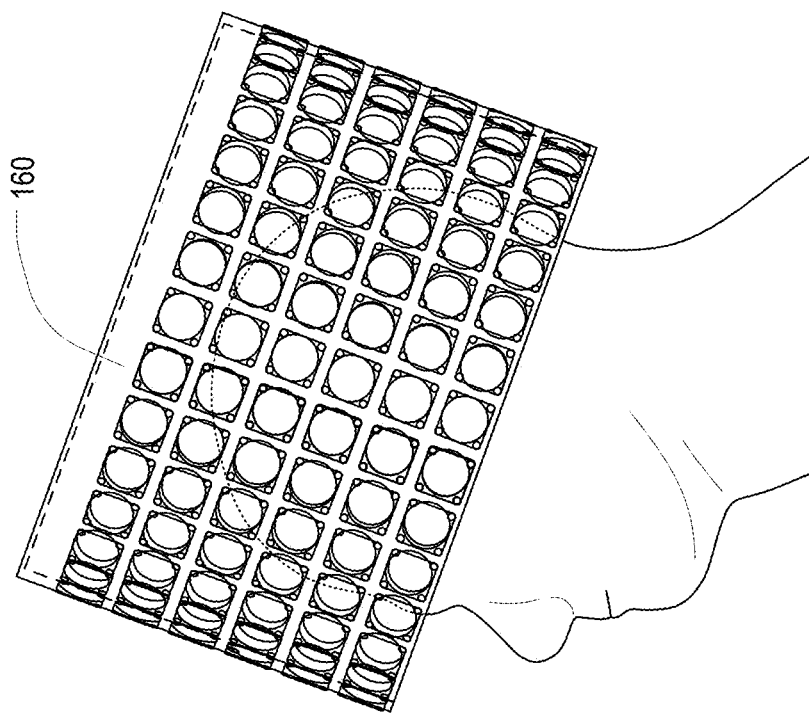

As noted previously, the imaging domain 21 of the imaging chamber system 150 is defined by and within the imaging chamber 160. In this regard, FIGS. 8A and 8B are side views of a cylindrical electromagnetic tomography (EMT) imaging chamber 160, shown without and with antennas 165 installed therein, for use in the imaging chamber system 150 in accordance with one or more preferred embodiments of the present invention. In the illustrated embodiment, the antennas 165 are slot antennas, but it will be appreciated that other types of antennas, such as waveguide antennas, may be used instead. In the illustrated embodiment, the cylindrical imaging chamber 160 includes 192 antennas 165, each with an adaptor, that are arranged in six rings of 32 antennas each. In some embodiments, the antenna adaptors are linked to a box of 192 specifically designed printed circuit boards (PCBs) by semi-rigid coaxial cables, or are integrated directly into PCBs, wherein the PCBs provide control and data processing functionality, including the generation of the electromagnetic (EM) signals to be transmitted from the emitting antennas and the measurement of complex EM signals in the receiving antennas. However, in some embodiments, other physical implementations are possible; for example, as described below, the number of separate control devices may be reduced through the use of sequential, rather than simultaneous, operation of the antennas.

Figure 9:
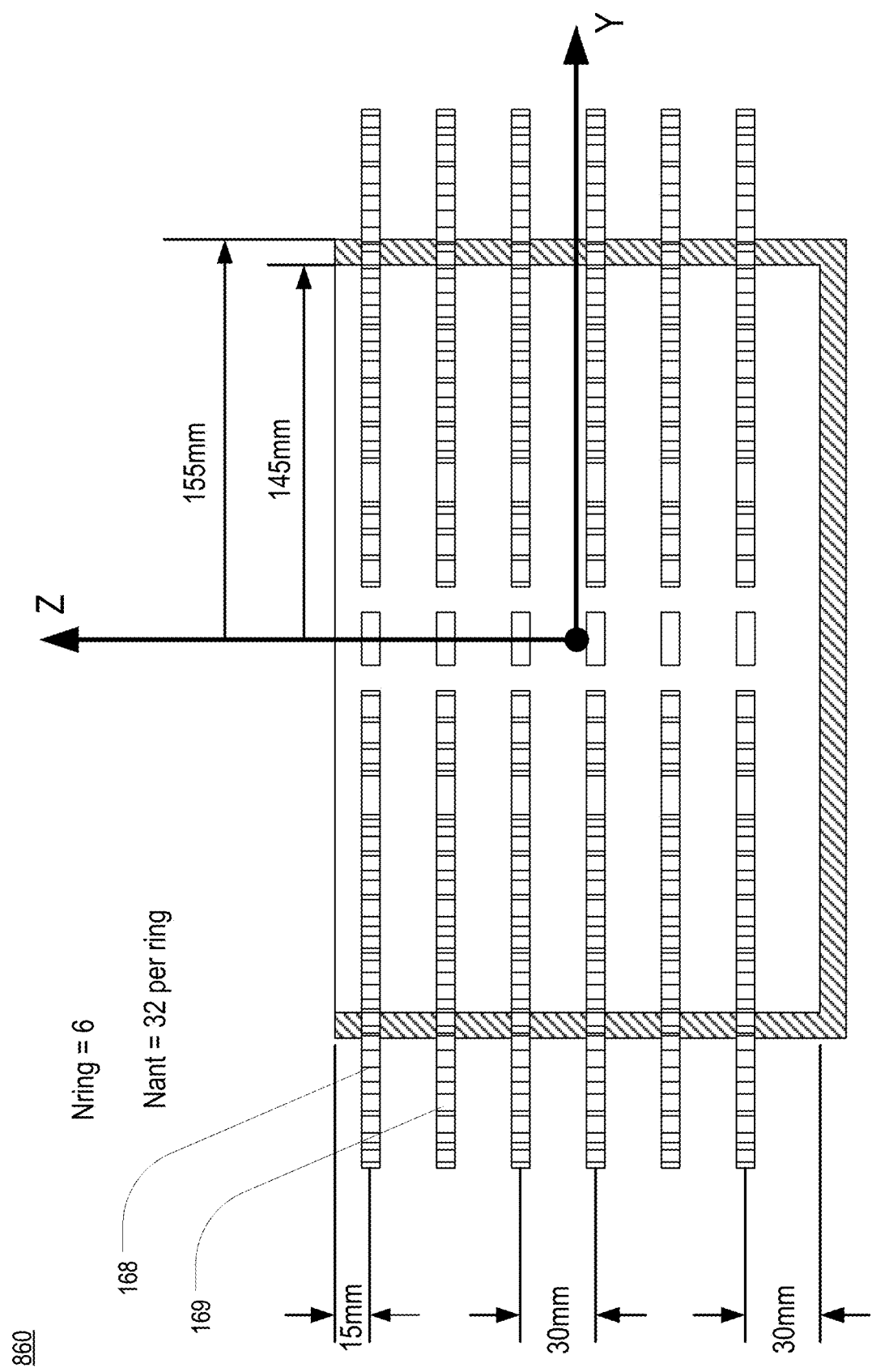
FIG. 9 is a side cross-sectional view of an exemplary cylindrical electromagnetic tomography (EMT) imaging chamber for use in an electromagnetic tomographic scanner in accordance with one or more preferred embodiments of the present invention.

FIG. 9 is a side cross-sectional view of an exemplary cylindrical electromagnetic tomography (EMT) imaging chamber 860 for use in an electromagnetic tomographic scanner in accordance with one or more preferred embodiments of the present invention. As shown therein, six rings of antennas of 32 antennas each are provided. The chamber 860 is 195 mm deep and the six various rings are spaced 30 mm apart such that the first ring (the ring nearest the opening of the chamber 860, which is shown at the top in FIG. 9) is positioned 15 mm from the edge of the opening and the sixth ring (the ring closest to the bottom of chamber 860) is positioned 30 mm from the bottom. The interior of the cylindrical chamber has a radius of 145 mm (diameter of 290 mm) and the exterior of the chamber has a radius of 155 mm (diameter of 310 mm). It will be appreciated that other numbers of rings, numbers of antennas per ring, spacing between rings, spacing between first ring and opening, spacing between final ring and chamber bottom, depth of chamber, interior and exterior radius/diameter of the cylinder, and other dimensions may be varied as desired.

Figure 10B:
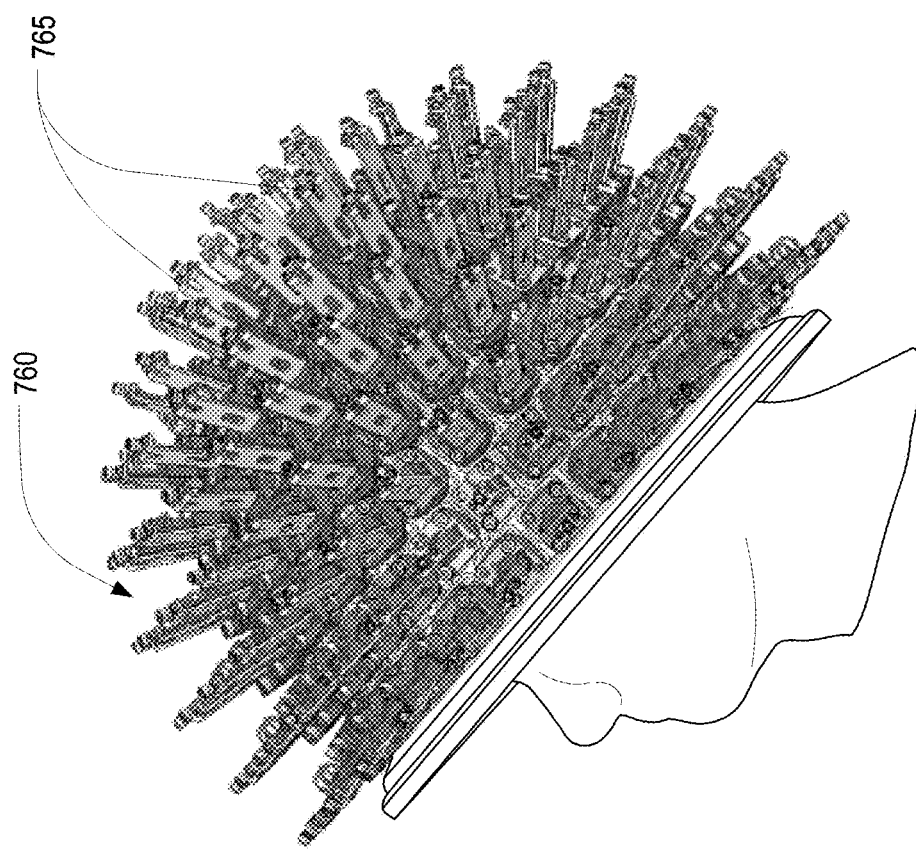
FIGS. 10A and 10B are side views of an alternative spherical electromagnetic tomography (EMT) imaging chamber, shown without and with antennas installed therein, for use in an imaging chamber system in accordance with one or more preferred embodiments of the present invention.
Figure 10A:
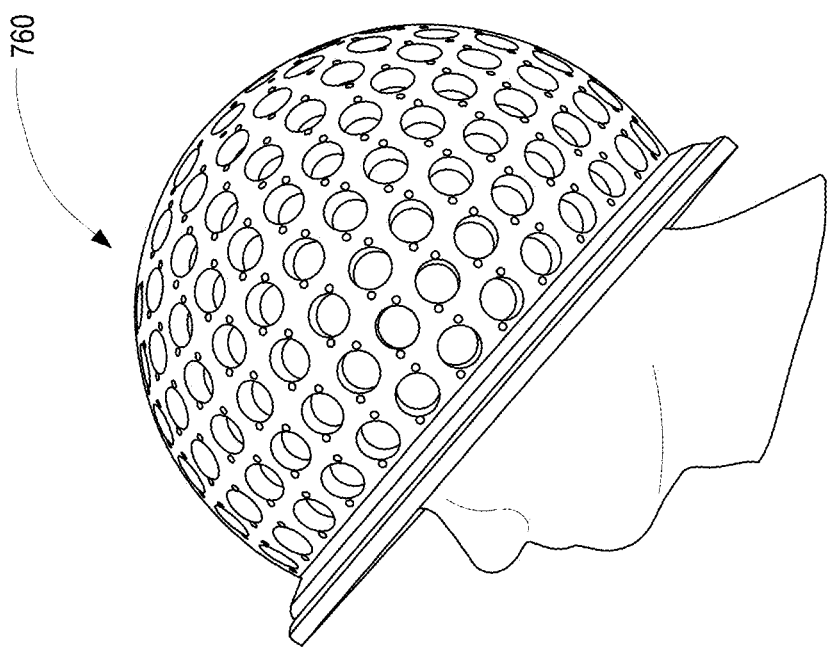

In alternative embodiments, imaging chambers of other topologies may be utilized. In this regard, FIGS. 10A and 10B are side views of an alternative spherical electromagnetic tomography (EMT) imaging chamber 760, shown without and with antennas 765 installed therein, for use in an imaging chamber system in accordance with one or more preferred embodiments of the present invention. In the illustrated embodiment, the antennas 765 are waveguide antennas, but it will be appreciated that other types of antennas, such as slot antennas, may be used instead. In the illustrated embodiment, the spherical imaging chamber 160 includes 177 antennas 765, each with an adaptor, that are arranged in eight tiers of varying numbers of antennas each plus pole antenna. In some embodiments, the antenna adaptors are linked to a box of 177 specifically designed printed circuit boards (PCBs) by semi-rigid coaxial cables, or are integrated directly into PCBs, wherein the PCBs provide control and data processing functionality. However, in some embodiments, other physical implementations are possible; for example, as described below, the number of separate control devices may be reduced through the use of sequential, rather than simultaneous, operation of the antennas.

Figure 11:
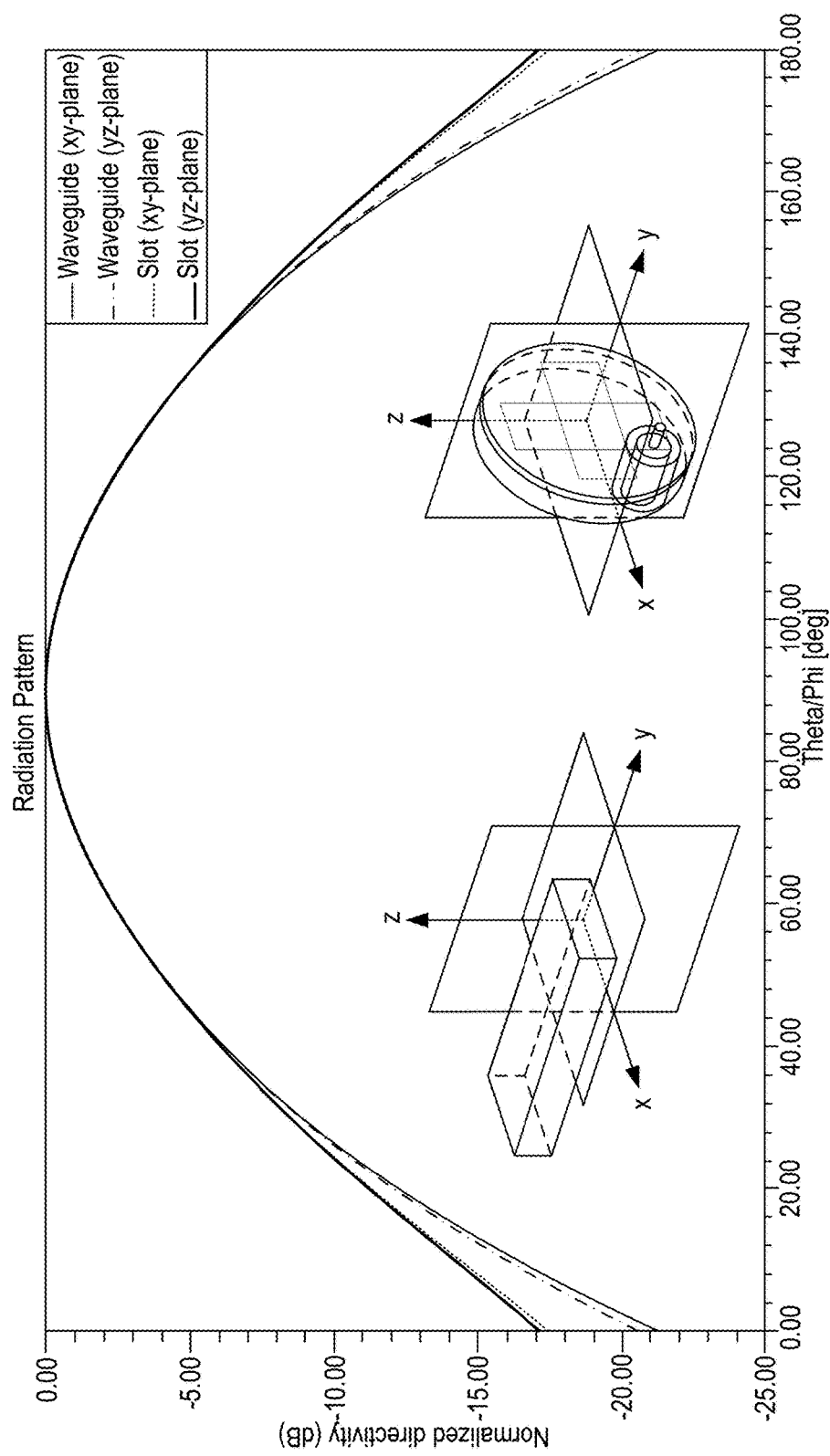
FIG. 11 is a graphical representation of a preferred radiation pattern for use in one or more preferred embodiments of the present invention.

The antennas are preferably designed to produce a particular pattern of radiation in order to improve the image reconstruction process. In this regard, FIG. 11 is a graphical representation of a preferred radiation pattern 250 for use in one or more preferred embodiments of the present invention. As shown therein, a desired radiation pattern 250 may be produced in both the x-y plane and the y-z plane using either specifically-designed slotted antennas 165 or specifically-designed waveguide antennas 765.

Figure 12:
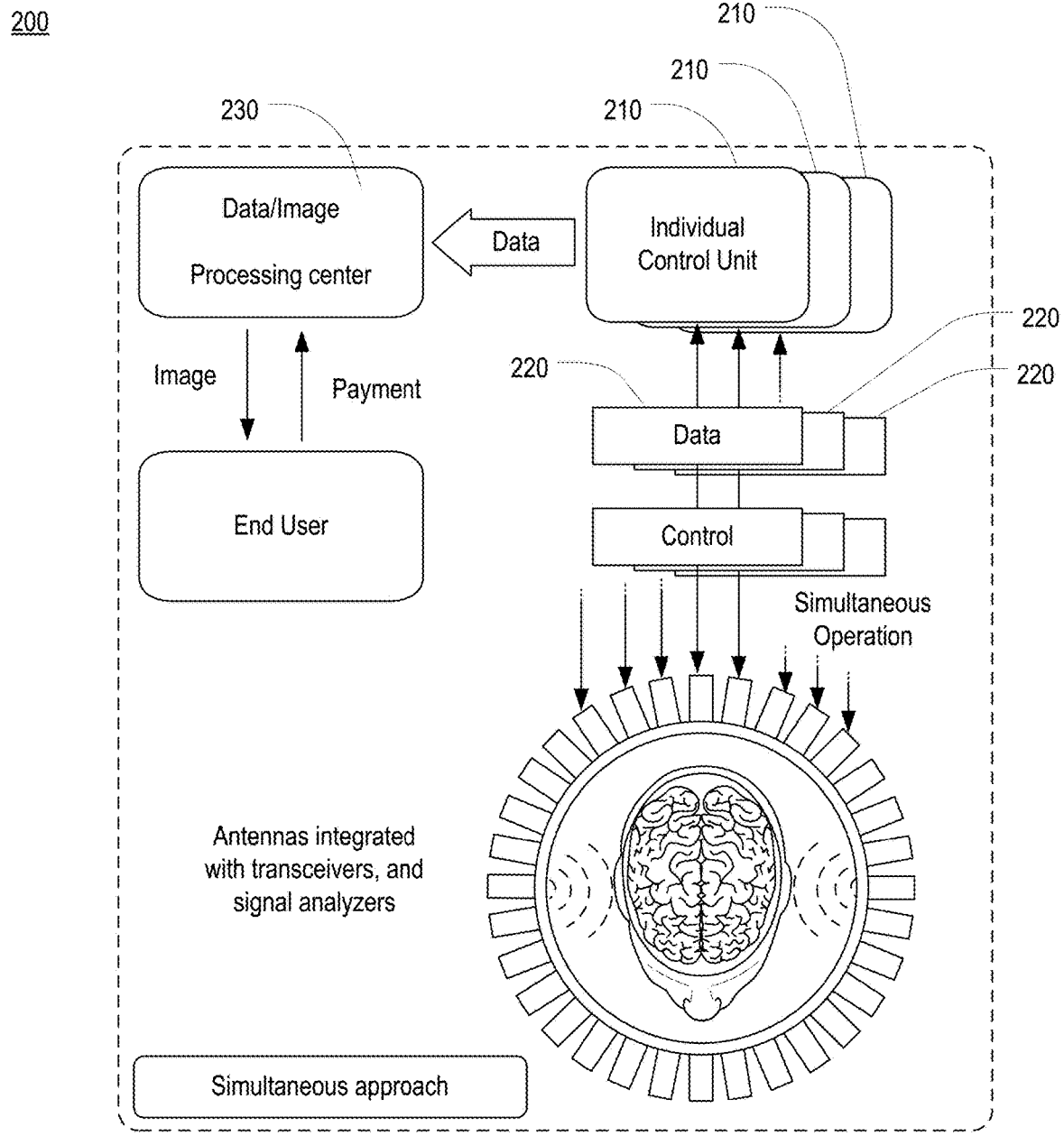
FIG. 12 is a simplified block diagram of hardware for simultaneous antenna operation in an EMT imaging chamber.

The antennas 165,765 preferably operate simultaneously, wherein each antenna 165,765 is integrated or connected to its own transceiver and signal analyzer. In this regard, FIG. 12 is a simplified block diagram of hardware 200 for simultaneous antenna operation in an EMT imaging chamber 160,760. Using this approach, when any one of the antennas is transmitting, the signals received at all of the other antennas are measured simultaneously. With well-designed control functionality, transceiver modules are synchronized, and resulting data 220 from the transmission/reception process is easily organized and distributed to the Data/image Processing Center 230.

Figure 13:
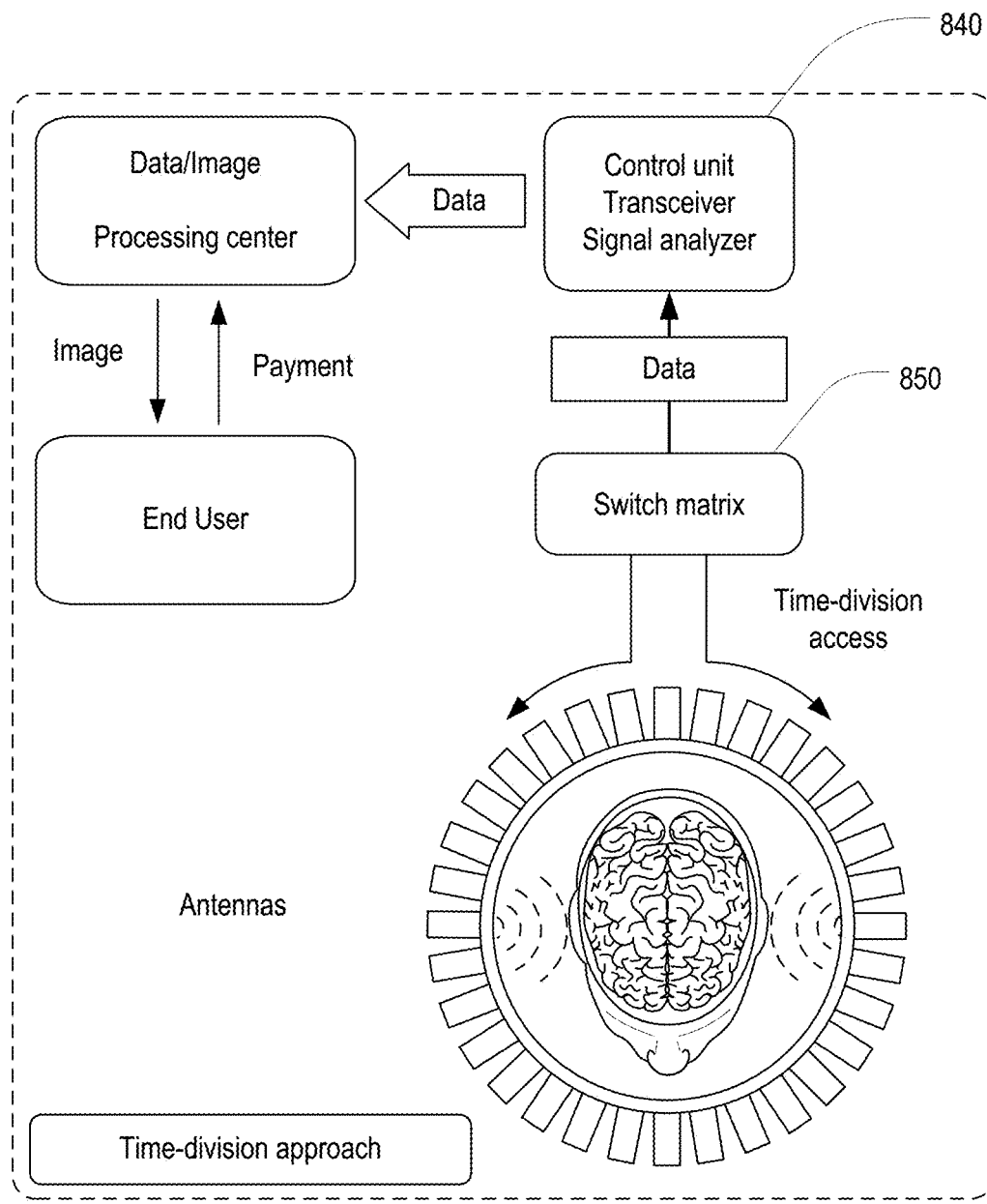
FIG. 13 is a simplified block diagram of hardware for sequential antenna operation in an EMT imaging chamber.

In some embodiments, it may be possible to use a sequential or "switching" approach such as that described in the aforementioned U.S. Pat. No. 9,414,749. Such an approach is shown as an alternative embodiment in FIG. 13, which is a simplified block diagram of hardware 800 for sequential antenna operation in an EMT imaging chamber 160,760. As shown therein, a single control unit 840 with radio frequency transceiver and signal analyzer 840 is connected to a switch matrix 850 that manages access to the antennas 165,765. It is generally preferred that the signal analyzer 840 is a vector network analyzer (VNA). The switch matrix 850 conventionally utilizes a time-division approach, wherein each antenna 165,175 is connected to the same electronic controls but data is saved in different time slots. However, when this conventional 2-port VNA/switch matrix/time-division strategy is utilized, it suffers from various problems that are believed to be overcome through the use of a simultaneous approach such as that shown in FIG. 12. This may be understood as follows.

When imaging a human brain, it is generally useful, and often even necessary, to have a fairly large number of antennas (for example, 177 or 192 in the various specific embodiments illustrated herein). Large numbers of antennas likewise require an increase in the size of the switch matrix 850. Unfortunately, these switches are relatively large and have fixed physical dimensions, and their size and weight has a substantial effect on the overall size and weight of the system. In the simultaneous approach, by contrast, the switch matrix 850 is not necessary. Instead, integrating such circuitry with each antenna (thereby avoiding the need for a switch matrix) improves technical specifications of the system (such as reducing data acquisition time from tens of minutes to milliseconds, effectively improving signal-to-noise ratio by avoiding movement artifacts of live biological objects during the resulting short (millisecond) data acquisition time, and allowing for circulation-gated imaging) and reduces the weight and dimensions of the system by at least a factor of two.

Another drawback to the sequential approach is a lack of scalability. If additional antennas are desired (for greater precision or the like), the switch matrix must be redesigned with ever-increasing complexity. In the simultaneous approach, if additional antennas are desired, they are simply added.

It will also be appreciated that the dielectric properties of both the matching media and the human brain itself are highly attenuative. (As further discussed hereinbelow, in at least some preferred embodiments, the matching media is formulated so as to have dielectric properties similar to the "average" dielectric properties of a human brain.) Thus, as the signals are sent and received, there is a decrease in magnitude of the wave properties as they travel due to absorption and scattering of the signals. This, in turn, requires the use of lengthy measurement times (e.g., 10 milliseconds) in order to achieve a good signal-to-noise (S/N) ratio. When these measurements are carried out sequentially, a separate measurement must be carried out for each combination of transmitting and receiving antenna. Thus, for example, if all possible measurements are made in a system in which 192 antennas are used, there are a total of 192×191 measurement periods which require a total measurement time of 192×191×10 milliseconds, which totals more than 6 minutes. Operation of the switch matrix to adjust control from one pair of antennas to another requires still further time. Unfortunately, it is difficult if not impossible for the human body to remain completely free of movement for 6 minutes or more, which means that taking measurements over such a long period of time inevitably introduces additional "movement" noise into the results.

In the simultaneous approach, by contrast, the data acquisition times are much shorter because measurements are made at all receiving antennas simultaneously. For example, if all possible measurements are made in a system in which 192 antennas are used, then 191 measurements are made simultaneously (in parallel) while each of the 192 antennas is transmitting. Assuming the measurement time remains the same (e.g., 10 milliseconds), there are a total of only 192 measurement periods which require a total measurement time of 192×10 milliseconds, which totals only about 2 seconds.

Overall, the simultaneous approach thus allows for considerably shorter data acquisition times as compared to a sequential approach, reduces the size and weight of the necessary hardware, provides greater scalability, and is better able to provide more measured components for the complex-valued tensors used in image reconstruction processes described elsewhere herein.

Figure 14:
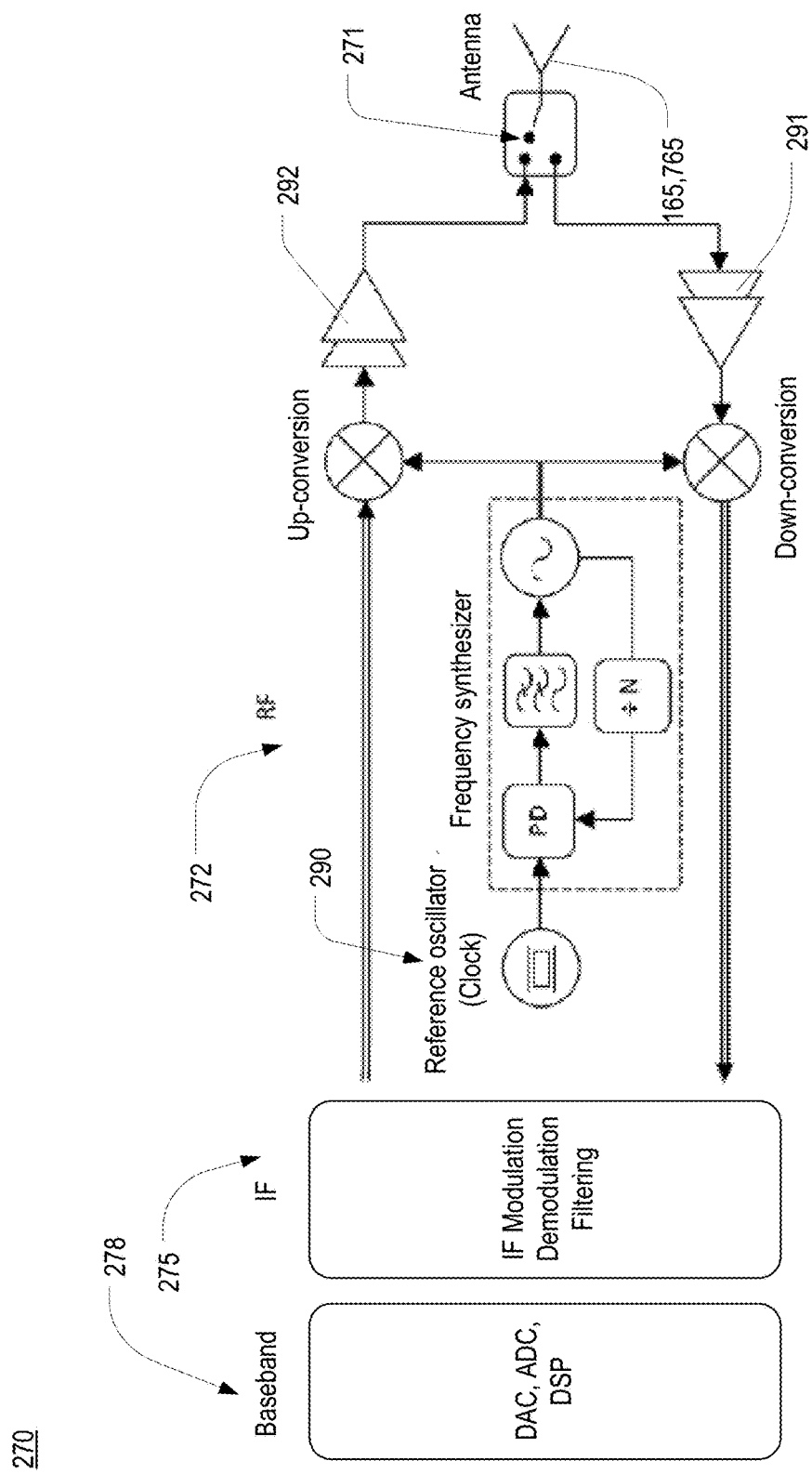
FIG. 14 is a block diagram illustrating the application of a superheterodyne architecture for use in the electromagnetic tomographic scanner.

In at least some embodiments, the radio frequency (RF) transceiver circuitry and related hardware may be implemented using a superheterodyne technology-based architecture, wherein radio signals are converted to/from a fixed intermediate frequency (IF) that can be more conveniently processed than the original carrier frequency. In this regard, FIG. 14 is a block diagram illustrating the application of a superheterodyne architecture for use in the electromagnetic tomographic scanner 110. As shown therein, the control hardware 270 includes circuitry comprising an RF stage 272 that is connected to the antenna 165,765, circuitry comprising an intermediate frequency (IF) stage 275, and a baseband (BB) data processing stage 278. The RF stage is connected to the antenna 165,765. In at least some embodiments, the RF transceiver circuitry 270 has a transmit side and a receive side that are alternately connected to the antenna 165,765 using an RF switch 271. Power amplifiers 291 and low-noise amplifiers 292 are preferably provided in the transmit path and the receive path, respectively, in order to address attenuation issues inherent with RF signals in brain tissues. For example, at a frequency of 1 GHz, the mean value for dielectric attenuation of the brain is about 2.5 dB/cm.

The heart of a preferred RF transceiver 272 is a frequency synthesizer that provides a high frequency carrier signal (e.g. 1 GHz) for the analog modulation/demodulation process. Similarly, an IF carrier signal is modulated/demodulated using the back-end digital signal. Filtering, amplification, and other IF functions are likewise carried out in the IF stage 275, and signal/data conversion (DAC/ADC) and digital post processing are conducted in the baseband stage 278.

Notably, quadrature modulation is applied such that the IF signal has both in-phase and quadrature components. These two components allow for vector analysis, or the tracking of changes in both amplitude and phase of the received signal. Furthermore, because the transmitter and receiver share a common clock oscillator 290, amplitude and phase of the received signal can be determined with reference to the transmit signal.

Depending on the design of the antennas 165,765, the RF transceiver circuitry 272, and the control thereof, the interconnection might be realized by semi-rigid coaxial cables or printed strip lines. In a preferred embodiment, this is realized with a two-module PCB-based implementation of antennas and corresponding RF transceiver circuitry. In an example of such an arrangement, the necessary functionality for the antennas 165,765 is implemented on a first module and the necessary RF transceiver circuitry 272 is implemented on a second module, wherein each module includes a PCB that is about 40 sq. cm. in size, and the modules are interconnected via coaxial cables. By removing the switch matrix technology and introducing PCB-based technology, significant weight and size reductions in hardware are obtained.

Figure 15:
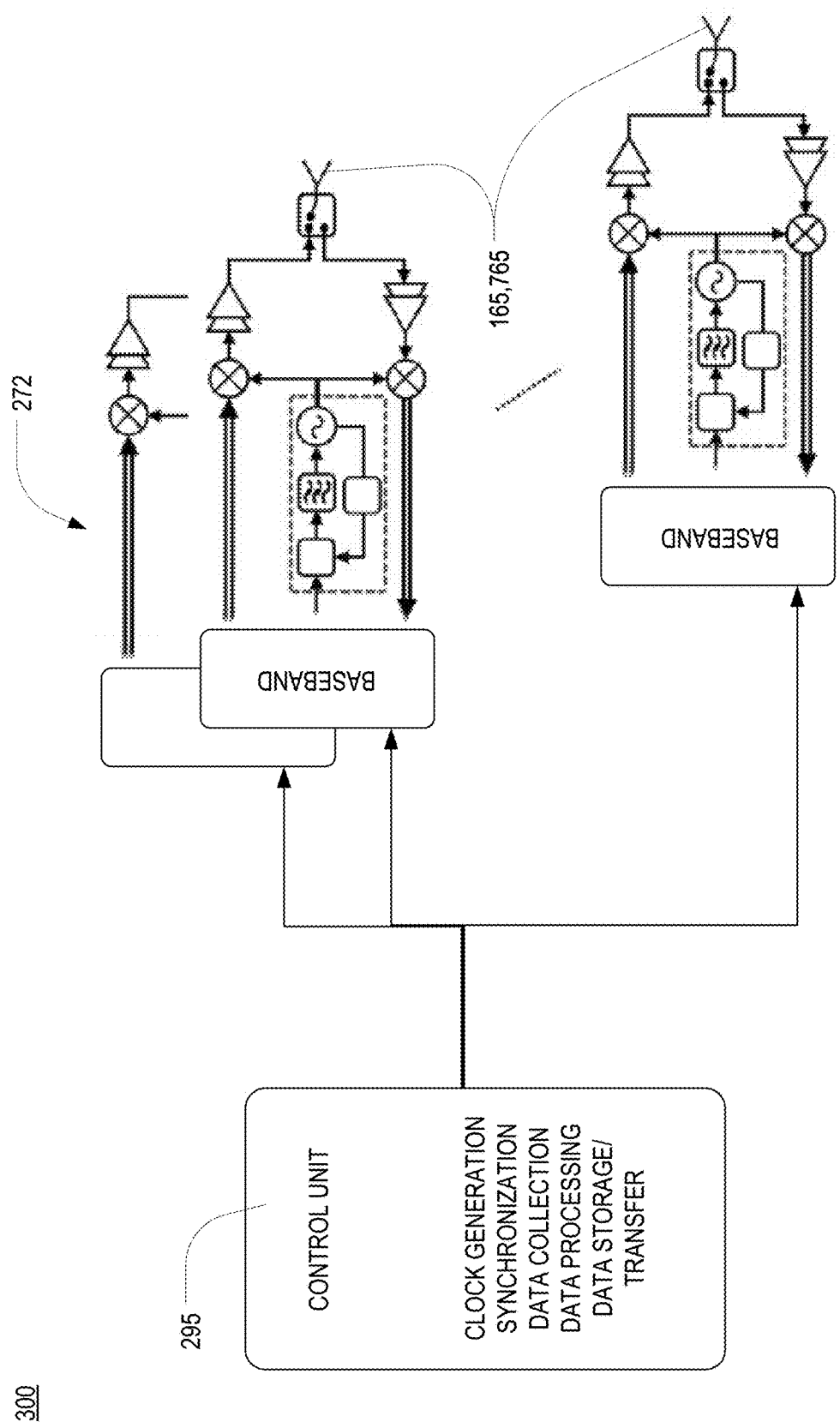
FIG. 15 is a block diagram illustrating the application of a synchronized superheterodyne architecture for use in the electromagnetic tomographic scanner.

It will be appreciated that for simultaneous operation, the individual controllers must be synchronized. In this regard, FIG. 15 is a block diagram illustrating the application of a synchronized superheterodyne architecture for use in the electromagnetic tomographic scanner 110. As shown therein, the control hardware 300 includes a single control unit 295 that provides functionality for an arbitrary number of antenna controllers and their respective antennas. Such functionality may include, for example, clock generation (including a common clock oscillator), synchronization, data collection, data processing, and data storage/transfer. In at least some embodiments, the control unit 295 is implemented separately (e.g., on a separate PCB) from the PCBs containing the RF transceiver circuitry 272.

Figure 16:
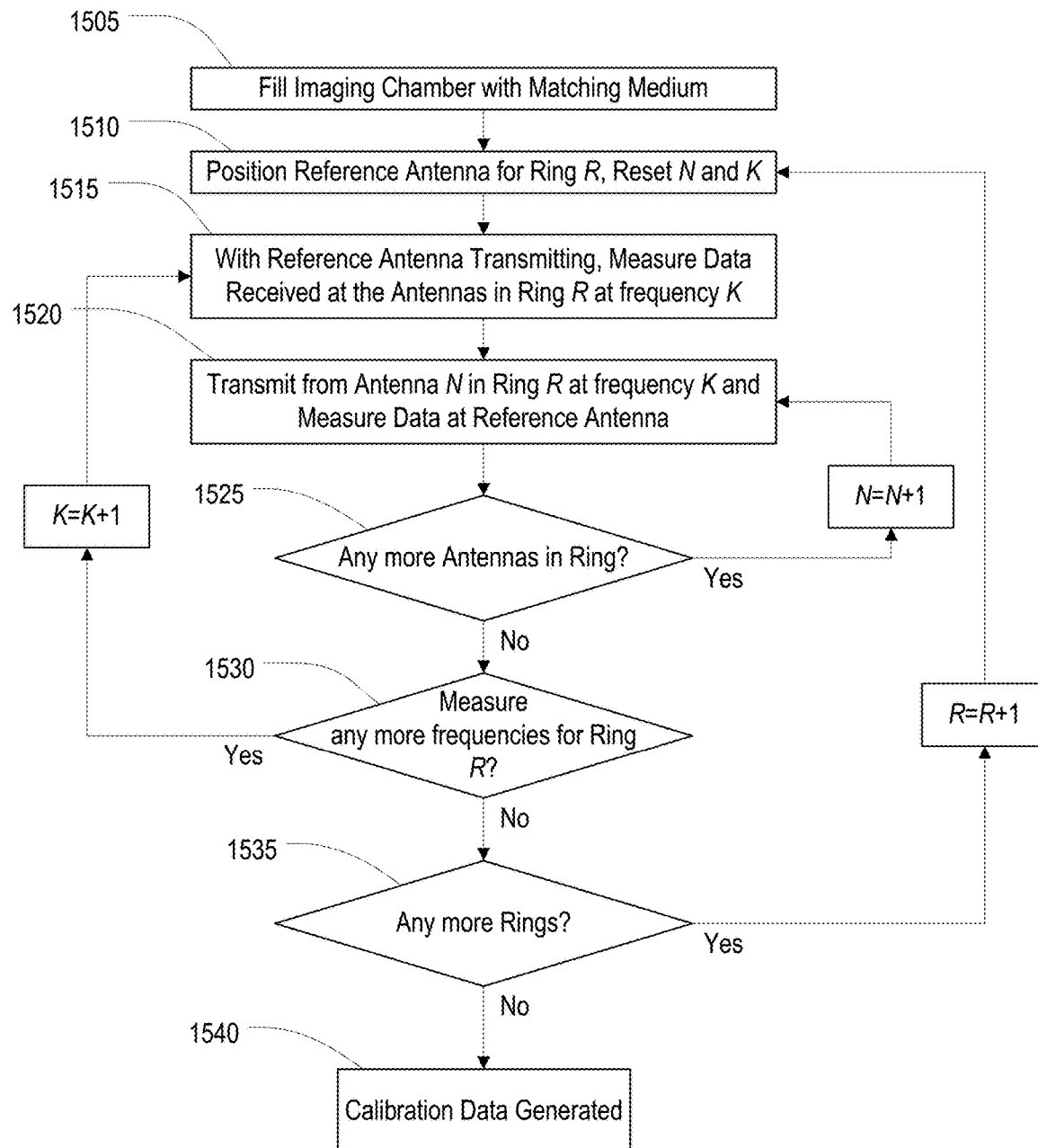
FIG. 16 is a flow diagram of an exemplary calibration process for use in one or more preferred embodiments of the EMT system shown in FIG. 3.

When dedicated RF transceiver circuitry 272 is utilized for each antenna 165,765, performance variations between each of the transmitting (Tx) or receiving (Rx) channels can be expected due to the imperfections of manufacturing and assembly. Therefore, an equalization technique, referred to as a calibration process, is desirable in order to quantify the received signals relative to each other and thus compensate for such variations. In this regard, FIG. 16 is a flow diagram of an exemplary calibration process 1500 for use in one or more preferred embodiments of the EMT system 100 shown in FIG. 3, although other approaches may additionally or alternatively be utilized. The exemplary calibration process 1500 is preferably carried out under conditions similar to those in which the system will actually be used, but without a patient being present. During actual use, at least in some embodiments, the space in the imaging chamber 160 around the patient's head is occupied with a background or matching media. Thus, as a preliminary step 1505 in the calibration process 1500, the imaging chamber 160 is first filled with the appropriate matching media before carrying out the rest of the process 1500. In at least some embodiments, the open end of the imaging chamber 160 is covered with a lid to crudely mimic boundary conditions, prevent matching media from spilling from the chamber 160, and/or for other purposes.

The matching media is a fluid or gel that is used to address electromagnetic body-matching problems and/or other issues. In at least some embodiments, the matching liquid is a mixture of glycerol (Ph. Eur.), water and brine. In at least some preferred embodiments, the matching media is formulated so as to have dielectric permittivity ($\epsilon=\epsilon'+j\epsilon''$) that is similar to an averaged value of all brain tissues, i.e., the average of everything inside a skull. Thus, in those preferred embodiments, $\epsilon'$=about 30 to 60 and $\epsilon''$=about 15 to 25, and in at least some embodiments, $\epsilon'$=about 40 to 45 and $\epsilon''$=about 17 to 21. By using a matching media whose dielectric permittivity is so similar to the collective average of the brain tissue, it is believed that an effect of skull-shielding is minimized.

Figure 17:
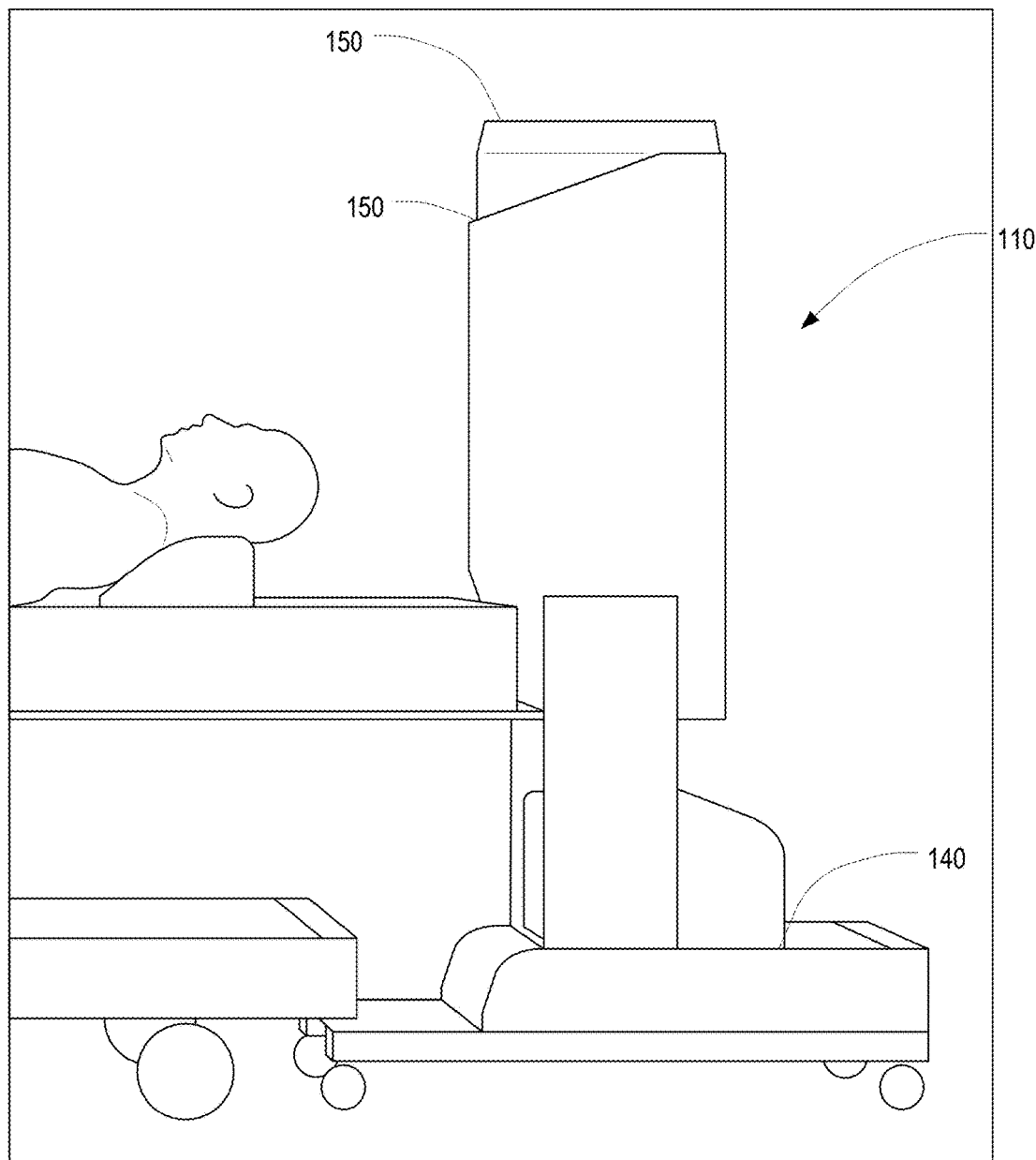
FIG. 17 is a side view of the moveable imaging chamber system of FIG. 3, shown in a vertical position.

According to various aspects of the present invention, the imaging chamber 160 may be filled with a matching media in various ways. In some embodiments, technology such as that disclosed in the aforementioned U.S. Pat. No. 9,414,749 may be used. In some embodiments, the imaging chamber system 150 may be equipped to rotate at least the imaging chamber 160 upward such that gel may be loaded into the chamber 160. In at least some of these embodiments, the imaging chamber 160 may be rotated to a vertical orientation wherein the main axis thereof is oriented vertically. In this regard, FIG. 17 is a side view of the moveable imaging chamber system 150 of FIG. 3, shown after being rotated to a vertical position. Such a position may be useful, for example, for loading matching media into the imaging chamber 160, calibrating the system, and/or measuring the empty field. Details of some preferable methodologies for these steps are described elsewhere herein. Notably, in some embodiments, the imaging chamber 160 is not rotated fully vertical.

Figure 18B:
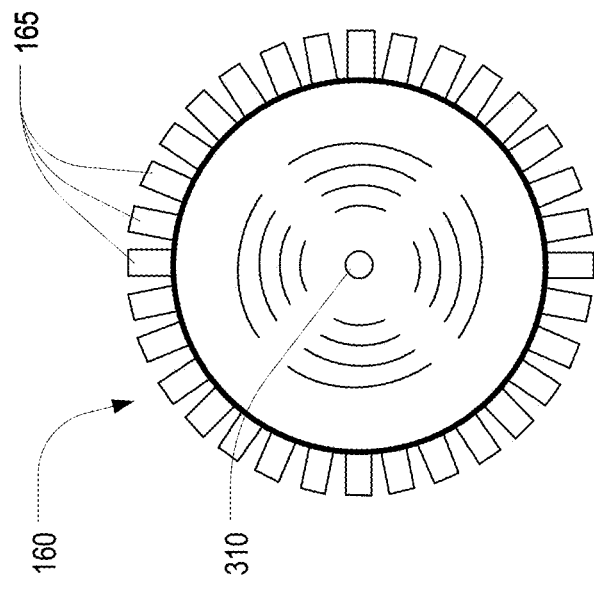
FIG. 18B is a schematic diagram of the reference antenna and imaging chamber of FIG. 18A, illustrating an omnidirectional radiation pattern of the antenna.
Figure 18A:
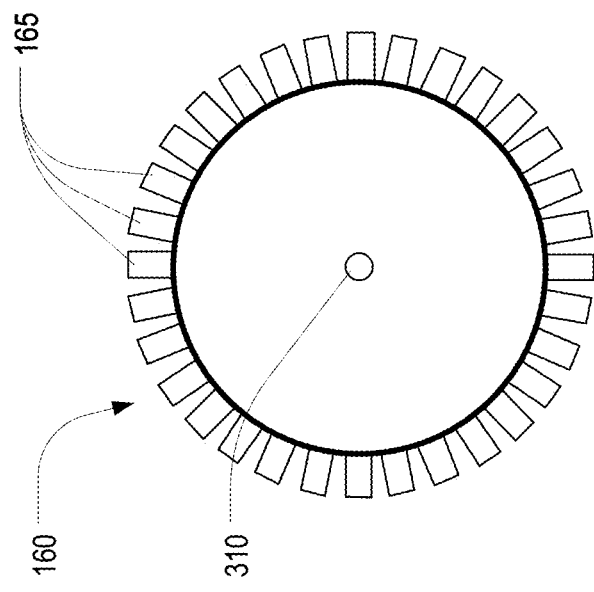
FIG. 18A is a schematic diagram of a reference antenna temporarily positioned in the center of an imaging chamber.
Figures 18C, 19:
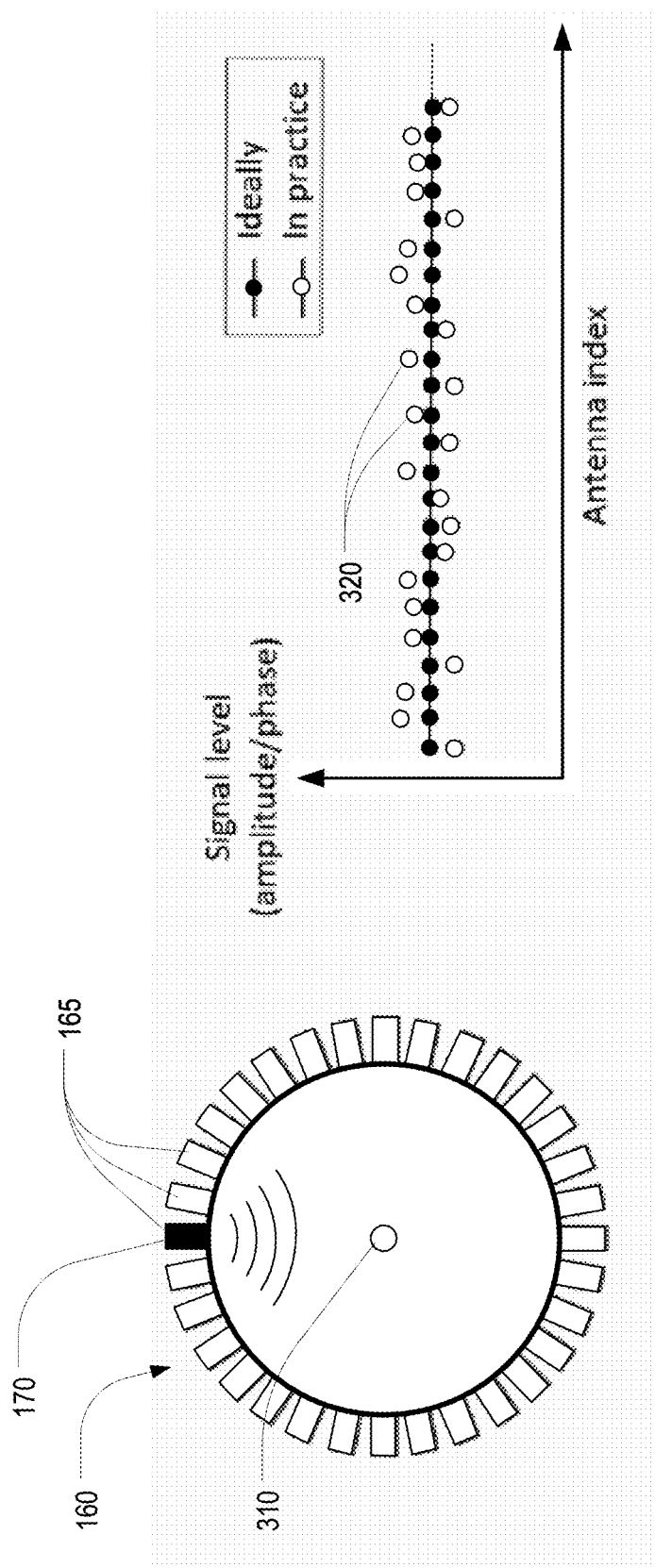
FIG. 18C is a schematic diagram of one antenna of interest transmitting for purposes of measuring data received at the reference antenna.
FIG. 19 is an exemplary graphical representation of measured signals received from the reference antenna by various antennas around a ring.

With the matching media in place, a reference antenna 310 is precisely positioned at the center of a ring R of N antennas. In this regard, FIG. 18A is a schematic diagram of a reference antenna 310 temporarily positioned in the center of an imaging chamber 160,760. The reference antenna 310 may be positioned with the help of a specifically designed high tolerance antenna holder (for example a monopole antenna). The reference antenna 310 is used to carry out two sets of measurements for each of K frequencies of interest. In one set of measurements, with the reference antenna transmitting, data is measured as received at each of the N antennas in the ring R, as shown at step 1515. This can be done at all N antennas simultaneously (or less preferably, one at a time, sequentially). As shown in FIG. 18B, the reference antenna 310 preferably has an omnidirectional radiation pattern, thereby permitting simultaneous measurement at all receiving antennas 165. In the other set of measurements, with the Nth antenna 170 in the ring transmitting, data is measured as received at the reference antenna 310, as shown at step 1520. In this regard, FIG. 18C is a schematic diagram of one antenna of interest 170 transmitting for purposes of measuring data received at the reference antenna 310. As shown at step 1525, the ring antenna of interest 170 is then incremented until steps 1515 and 1520 have been repeated for each antenna N in the ring R, and as shown at step 1530, this process is repeated for each desired frequency K. As shown at step 1535, steps 1510-1530 (including repositioning the reference antenna) are then repeated for each of the other rings until calibration data has been fully generated for all antennas, rings, and frequencies as shown at step 1540. (It will be appreciated that the flow diagram of FIG. 16 is illustrative only and that these steps need not be carried out in the specific order illustrated therein.) The calibration data thus obtained is a complex-valued tensor with coefficients $C_{i,j,k}^{Exp,calibr}$.

FIG. 19 is an exemplary graphical representation of measured signals received from the reference antenna 310 by various antennas 165 around a ring. By measuring characteristics of the received signals, shown by the white points 320 on the graph, while the reference antenna is transmitting, the differences (i.e., imperfections) among the receive paths are determined. Similarly, the differences among the transmit paths are identified when the reference antenna is operating in the receive mode while individual antennas 165 are transmitting. Mathematically, the matrix of calibration coefficients $C_{i,j,k}^{Exp,calibr}$ that is thus constructed may then be applied to raw measured data during actual operation of the system.

After the calibration process 1500 has been completed, the process of obtaining "raw" patient data may be carried out. The patient data generation process starts with the imaging chamber 160 completely filled with the matching medium, but no object inside. This empty field measurement is executed which results in a complex-valued tensor of I×J×k components, where I is the number of transmitting antennas, J the number of receiving antennas and k the number of measured frequencies. This tensor is represented by $S_{i,j,k}^{meas,empty}$, the S-parameters for the measured empty field for each pair of transmitting and receiving antennas i,j for each emitting frequency k. Next, as shown in FIGS. 4A and 4B, the patient 108 and/or the scanner 110 are moved, positioned, and/or adjusted such that the patient's head 109 is positioned in the correct position inside the chamber 160. With the patient's head 109 in place, the full field measurements are carried out, thereby producing a tensor, represented by $S_{i,j,k}^{meas,full}$, corresponding to the measured full field for each pair of transmitting and receiving antennas i,j for each emitting frequency k. A third tensor, represented by $S_{i,j,k}^{meas,scatt}$ and corresponding to the scattering caused by the patient's head 109, may then be obtained from the algebraic subtraction $S_{i,j,k}^{meas,scatt} = S_{i,j,k}^{meas,full} - S_{i,j,k}^{meas,empty}$. The three complex-valued tensors $S_{i,j,k}^{meas,full}$, $S_{i,j,k}^{meas,empty}$, $S_{i,j,k}^{meas,scatt}$, containing the S-parameters for each pair of transmitting and receiving antennas for each emitting frequency, and the calibration tensor $C_{ij,k}^{Exp,calibr}$, containing the calibration components for each pair of transmitting and receiving antennas for each emitting frequency, comprise the primary input data sets for the image reconstruction algorithms described below.

The boundary conditions when measuring the empty chamber containing only matching media ($S_{i,j,k}^{meas,empty}$) are preferably as close as possible to the boundary conditions when measuring the full chamber containing an object such as a human head and the matching media $S_{i,j,k}^{meas,empty}$. However, as can be seen in (for example) FIG. 3 and FIG. 4B, it will be appreciated that basic anatomy dictates that when a patient's head is placed in the chamber for measurement, the rest of the patient's body remains outside of the chamber. The portions of the patient's body that are outside the chamber typically include some or all of the patient's neck and lower portions of the patient's head itself. Notably, although outside the chamber, these portions (particularly including the lower portions of the patient's head 109 and neck) modify the boundary conditions for the electromagnetic fields measured inside the chamber as compared to when no human body 108 is present.

Figure 20B:
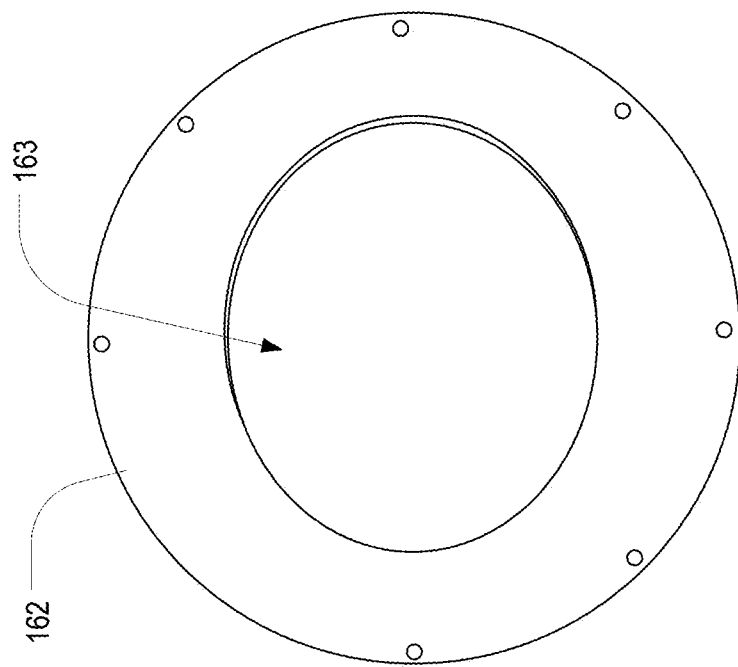
FIG. 20B is a front view of the frame of FIG. 20A.
Figure 20A:
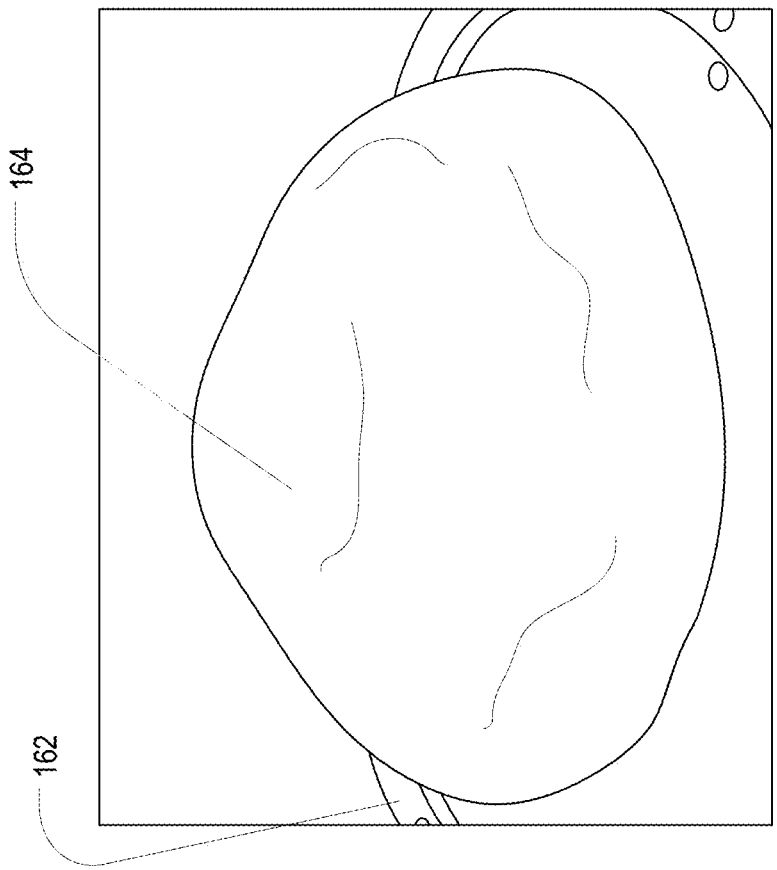
FIG. 20A is a perspective view of a lid, including a frame supporting a hollow boundary model, for use in at least some embodiments in mimicking the part of the body outside of the imaging chamber during empty field measurements.
Figure 20C:
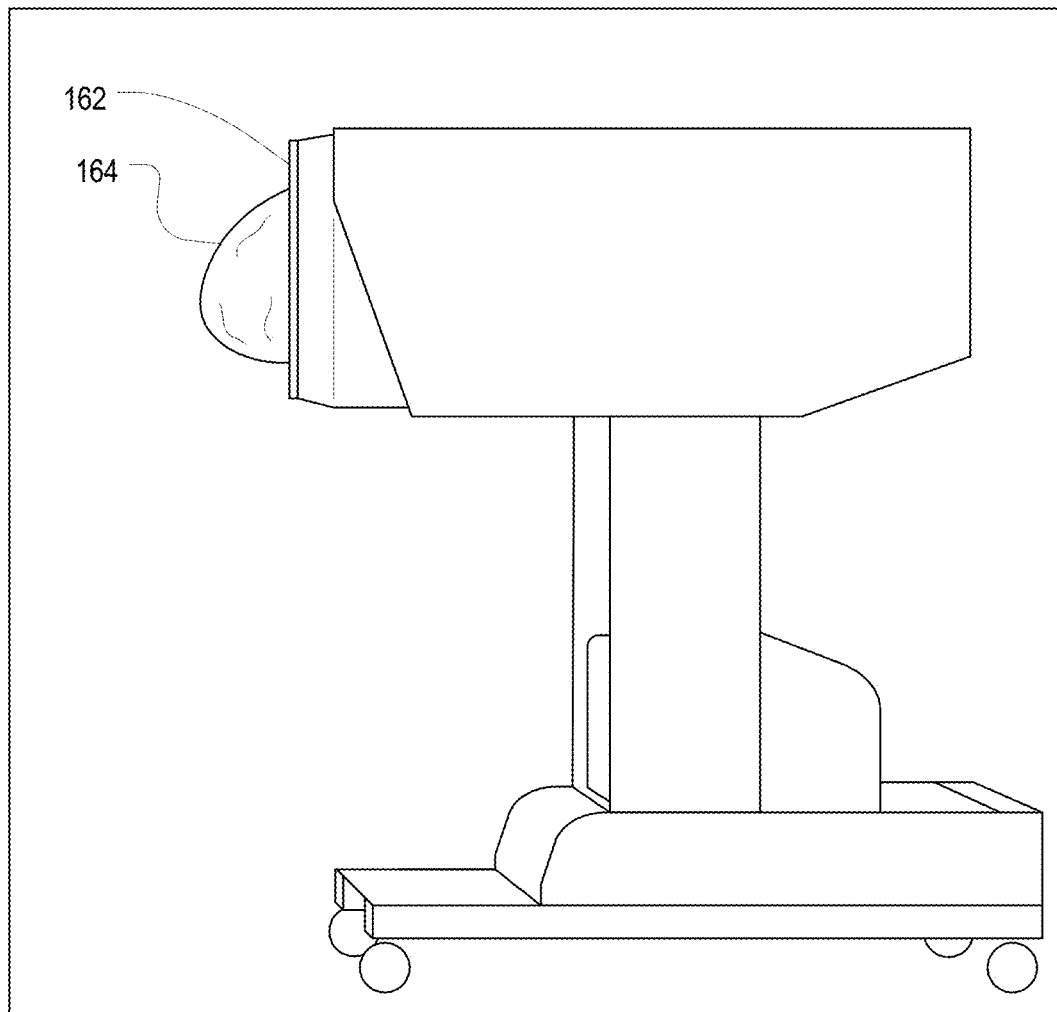
FIG. 20C is a side view of the electromagnetic tomographic scanner of FIG. 3, shown with the lid of FIG. 20A installed thereon.

Thus, in at least some embodiments, use may be made of an apparatus, when measuring the empty chamber, to mimic the boundary conditions that are present when measuring the full chamber. In this regard, FIG. 20A is a perspective view of a lid, including a frame 162 supporting a hollow boundary model 164, for use in at least some embodiments in mimicking the part of the body 108 outside of the imaging chamber 160 during empty field measurements. As shown therein, the hollow boundary model 164 roughly approximates the shape of the lower portion of a human head. The frame 162, which is preferably rigid, includes a centrally located ellipsoidal hole 163 through which the model 164 extends. In this regard, FIG. 20B is a front view of the frame 162 of FIG. 20A. In use, the hollow boundary model 164 may be attached to the rigid frame 162 and the lid may be installed across the opening of the imaging chamber 160. In this arrangement, the hollow boundary model 164 extends out of (away from) the chamber 160, roughly mimicking the disposition of the lower portion of a human head. When the interior of the model 164 (the portion facing the interior of the chamber 160) is filled (at least partially, but preferably fully) with matching media, the matching media thus extends out of the imaging chamber 160 and is positioned in the area where the remainder of the head 109 and possibly the neck of the body 108 would be located, as shown in FIG. 20C.

In some embodiments, the hollow boundary model 164 its own closed cavity so as to retain the matching media therein without escaping. In some embodiments, a closed cavity is created entirely by the model; in other embodiments, the closed cavity is formed between the model 164 and a full (solid) lid having no ellipsoidal or other opening therein.

In some embodiments, the imaging chamber 160 is at least partially tilted, or even inverted, so as to cause matching media to flow into or otherwise enter the interior of the hollow boundary model 164. In some such embodiments, the model 164 is sealed to the frame 162 and the lid is removably sealed to the imaging chamber 160 to prevent matching media from escaping from the imaging chamber and/or the interior of the hollow boundary model 164. In other embodiments, sealing may not be necessary; for example, if the matching media is in the form of a gel or otherwise has a consistency that does not flow readily, simple attachment of the lid to the imaging chamber may be sufficient to prevent escape of the matching media from the imaging chamber 160.

In various embodiments, the centrally located hole may take on shapes other than ellipsoidal, such as circular.

Figure 21:
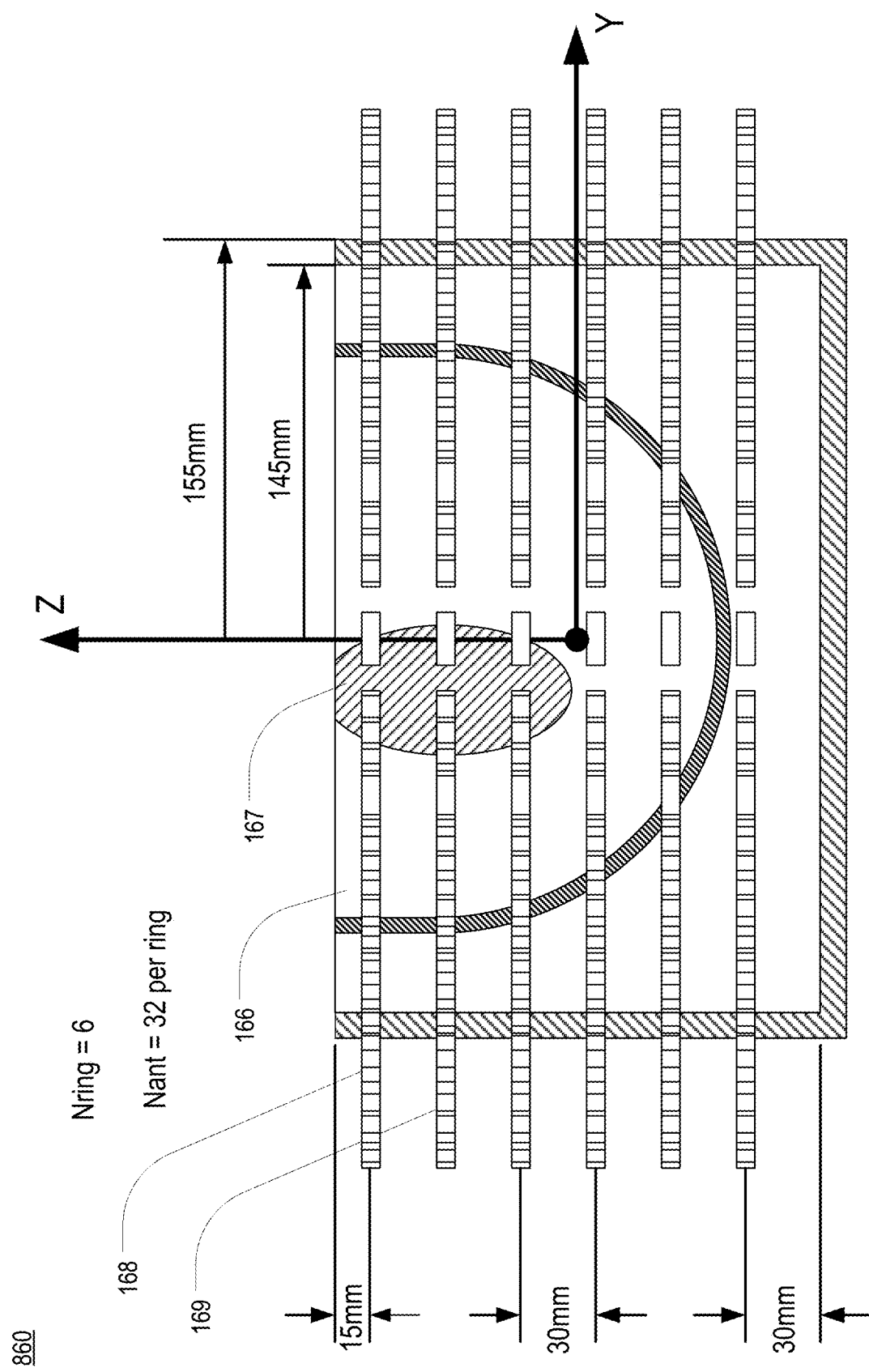
FIG. 21 is a side cross-sectional view of the exemplary cylindrical EMT imaging chamber of FIG. 9.

This additional feature to the invention better simulates the conditions of the boundary antenna measurements. For example, reference is made to FIG. 21, which is a side cross-sectional view of the exemplary cylindrical EMT imaging chamber 860 of FIG. 9 but having a human head phantom 166, including a hemorrhagic stroke model 167, positioned therein. Using this chamber 860, an EMT imaging process was carried out on the head phantom with stroke model using empty field measurements taken in two different ways. The first set of empty field measurements were taken on the empty imaging chamber 860 of FIG. 9 with a full (solid) lid covering the imaging chamber 860 and matching media filling the chamber 860 to the lid. The second set of empty field measurement was taken on the empty imaging chamber 860 with the frame 162 and hollow boundary model 164 of FIG. 20A covering the imaging chamber 860 and matching media filling the chamber 860 and the interior of the hollow boundary model 164. The full field measurements were then taken with the partial frame 162 of FIG. 20B in place, matching media filling the chamber 860, and the head phantom with stroke model extending through the lid and into the chamber 860.

Figures 22A, 22B, 22C:
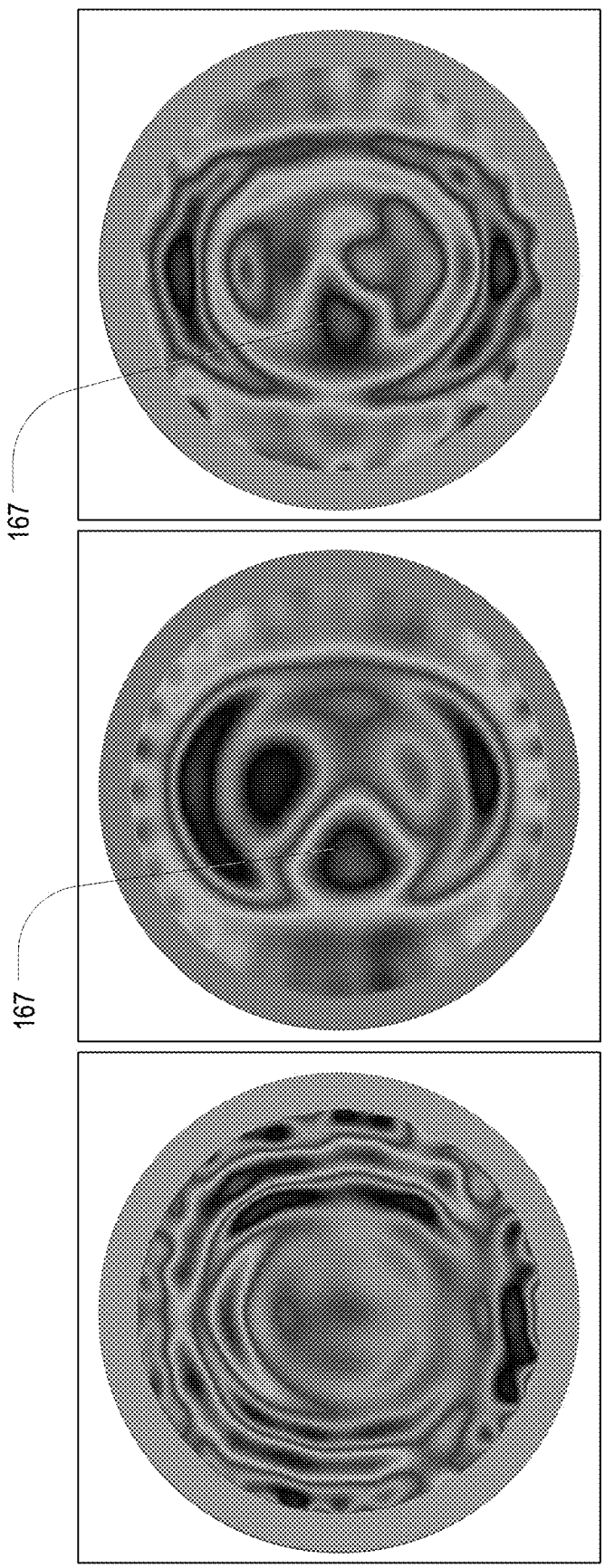
FIGS. 22A and 22B are graphical representations of the result of 2D image reconstruction for the human head phantom inside the chamber of FIG. 21 using the empty field measurement taken with a full lid.
FIGS. 22C is a graphical representation of the result of 2D image reconstruction for the same human head phantom of FIGS. 22A and 22B using the output from the first antenna ring, but where the empty field measurement was carried out with the partial lid and hollow boundary model of FIG. 20A covering the imaging chamber.

When 2D image reconstruction is carried out for various rings in based on empty field measurements using the different boundary conditions, the benefit of using the partial frame 162 and hollow boundary model 164 of FIG. 20A is clear. FIGS. 22A and 22B are graphical representations of the result of 2D image reconstruction for the human head phantom 166 inside the chamber 860 of FIG. 21 using the empty field measurement taken with a full lid, wherein FIG. 22A represents the 2D image reconstruction using output from the first antenna ring (the ring nearest the opening of the image chamber 860) and FIG. 22B represents the 2D image reconstruction using output from the second antenna ring. A shown in FIG. 22B, the reconstructed image from the second ring 169, which is not affected as strongly by the mismatched boundary conditions between the empty field measurements and the full field measurements because of its location relative to the exterior of the imaging chamber 160, reveals the presence of the hemorrhagic stroke model 167. However, as shown in FIG. 22A, the reconstructed image from the first ring 168 provides no indication of the hemorrhagic stroke model 167, due to the mismatched boundary conditions of the empty measurement and the full measurement.

On the other hand, when the boundary conditions of the empty field measurement and the full field measurement more closely match, even image reconstruction from the first antenna ring 168 identifies the hemorrhagic stroke model 167. In this regard, FIG. 22C is a graphical representation of the result of 2D image reconstruction for the same human head phantom 166, using the output from the first antenna ring 168, but where the empty field measurement was carried out with the partial frame 162 and hollow boundary model 164 of FIG. 20A covering the imaging chamber 860. As shown therein, the accuracy for the first antenna ring 168 using the improved empty field measurement approach is comparable to that of the second antenna ring 169 using the mismatched boundary conditions.

In at least some embodiments, the measured data is validated locally using fast 2D image reconstruction algorithms are executed to obtain a plurality of 2D slices before full 3D image reconstruction is conducted remotely. This two stage process may be recommended due to the technical challenges inherent in conducting on-site image reconstruction (i.e. in the control unit) for the full 3D vector problem due to significant numerical complexity which generally necessitates a computing cluster. Thus, for 3D image reconstruction, the experimental data generally needs to be transferred to a computing system 128 that includes a more powerful data processing unit than is generally available at the site of the electromagnetic tomographic scanner 110. On the other hand, 2D image reconstruction requires considerably lower data processing capability and can be carried out locally. Local 2D image reconstruction can thus be utilized for an initial validation of the measured data and a potential re-measurement of the data can be triggered immediately. Furthermore, the 2D slices (described below) can act as an initial condition for the full 3D reconstruction, thus potentially reducing the number of necessary iterations when solving the inverse problem. Still further, the initially reconstructed 2D slices do have considerable diagnostic power and provide valuable immediate information for the decision makers. In this regard, it should be appreciated that although image reconstruction based on the 2D solvers is possible, image reconstruction based on the full 3D solvers improves the images quantitatively, and a reconstruction using full 3D vector is strongly preferred in order to obtain a quantitative image in the whole volume.

In the 2D validation process, the measured data $S_{i,j,k}^{meas,full}$, $S_{i,j,k}^{meas,empty}$, after being collected as described above, is stored in the internal memory of a local database connected to the electromagnetic tomographic scanner 110, and the scattered data $S_{i,j,k}^{meas,scatt}$ is calculated and stored there as well. In some embodiments, the local database is provided in the local computer 129, which communicates directly with the electromagnetic tomographic scanner 110, while in some embodiments, data from the electromagnetic tomographic scanner 110 is stored in a local database (not shown), such as a database managed by the hospital in which the electromagnetic tomographic scanner 110 is located, and the local computer 129 communicates with the local database. The local computer 129 is used to conduct measured data validation. In particular, using image reconstruction procedures described below (and/or, at least some embodiments, in other patent documents), fast 2D image reconstruction algorithms are executed to obtain a plurality of 2D slices, wherein a 2D slice is obtained for each antenna ring. For example, if the chamber 160 includes six antenna rings, six 2D slices—one for the permittivity distribution in the plane of each ring—can be obtained.

After the validation procedure is complete, or in some cases concurrent with such procedure, the data file is encrypted and sent, preferably together with a checksum, to the remote 3D image processing computer system 128 located elsewhere in a hospital or other provider facility, at an IPC, or at another host. Transmission can be done using standard file transfer protocols such as, without limitation, SFTP/SCP, a VPN tunnel, or the like, where the size of the image reconstruction data (typically, a 2×N×N matrix of complex values, corresponding to the empty and full field, where N is the number of antennas) is usually lower than 5 MB. On the remote 3D image processing computer system 128, the data integrity is checked via the checksum and processed with an image reconstruction procedure such as the one detailed hereinbelow. The reconstructed image together with the experimental data is preferably also stored in a redundant database. Then, it is converted into DICOM format, encrypted and sent back to the decision makers.

At least for the purpose of maintaining patient confidentiality, a unique ID number may be generated for each data set and attached to the data file. Notably, in at least some embodiments, it is not necessary to include any patient related information, such as name, gender, or the like. Instead, using the unique ID number, the patient-related information can be added directly to the processed image in DICOM format when later delivered to the decision maker as a reconstructed image.

Figure 23:
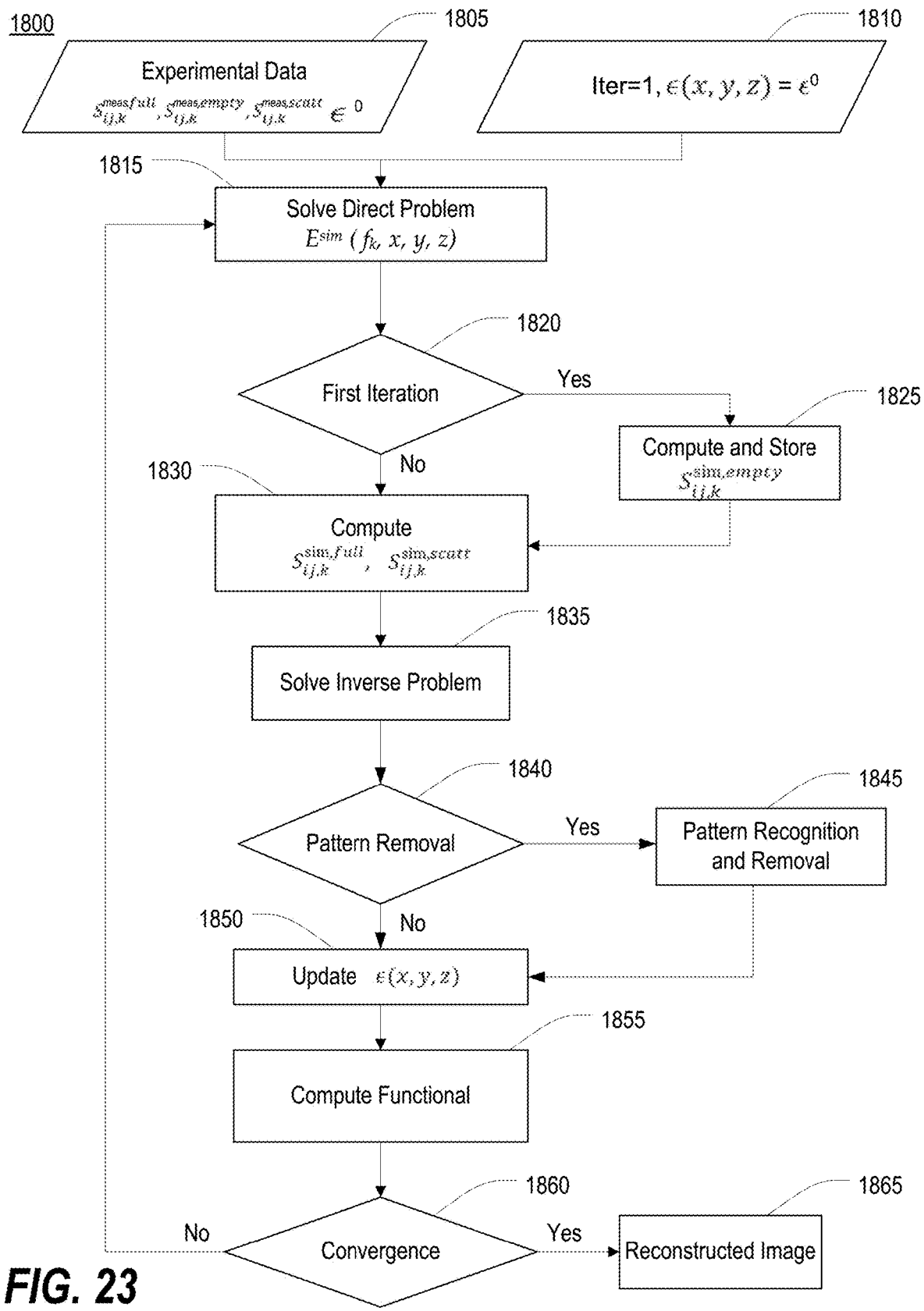
FIG. 23 is a high-level flow diagram of a 3D electromagnetic tomography image reconstruction (EMTIR) method for use in an EMT system in accordance with one or more preferred embodiments of the present invention.

Along with the hardware of the electromagnetic tomographic scanner 110, one or more specific methods is used to control the performance of the hardware in the scanner 110 during calibration, various measurements, data transfers, and other like procedure. In this regard, FIG. 23 is a high-level flow diagram of a 3D electromagnetic tomography image reconstruction (EMTIR) method 1800 for use in an EMT system 100 in accordance with one or more preferred embodiments of the present invention. The 3D EMTIR method 1800, which is generally carried out by the 3D image processing computer system 128, is an iterative process where a convergence check (shown at step 1860) occurs after each iteration through the various image reconstruction processes until suitable results are obtained and provided as the reconstructed image output 1865.

As noted previously, the primary input to the EMTIR method 1800 is three complex-valued tensors 1805 comprising the S-parameters between antenna pairs for each frequency. The number of tensor components is I×J×K, where I is the number of transmitting antennas, $S_{i=1\ to\ I}$, J is the number of receiving antennas $S_{j=1\ to\ J}$ and K is the number of emitting frequencies $f_{k=1\ to\ K}$. The three tensors 1805 contain the S-parameters for the full field (when the measured object 109 is inside the chamber 160), the empty field (when the chamber only contains the matching medium), and the scattered field (the field obtained due to the wave scattering phenomena from the measured object).

However, other inputs to the process 1800 are utilized as well. Other inputs (not shown in FIG. 23) may include, for example, calibration data (as described previously), physical properties of the matching medium, geometry (topology) and physical properties of the imaging domain 21, and antenna properties. Another input to the EMTIR method 1800 is an initial value for the dielectric permittivity distribution $\epsilon(x, y, z)$ 1810 in the imaging domain 21. In some preferred embodiments, this value is set as the matching medium permittivity value, $\epsilon^0(x, y, z)$. In other preferred embodiments, additional prior information about the measured object 109, obtained from conventional imaging modalities applicable for head imaging (such as but not limited to, MRI and CT), from fast 2D slices reconstruction and/or known from previous scans of the same object, may be used to establish such value.

At block 1815, the direct problem is solved. Solving the direct problem involves the computation of the EM fields inside the imaging domain 21 with dielectric permittivity $\epsilon(x, y, z)$ and the N transmitting antennas 165 acting as electromagnetic sources. The solution of the direct problem in block 1815 results in three additional complex-valued tensors containing the S-parameters for the full, the empty and the scattered fields ($S_{i,j,k}^{sim,full}$, $S_{i,j,k}^{sim,empty}$, $S_{i,j,k}^{sim,scatt}$ for each frequency) from the simulation point of view. Notably, the S-parameter tensor for the empty sim field, $S_{i,j,k}^{sim,empty}$, corresponds to the simulation of the chamber with matching medium but without the measured object 109. Therefore, as illustrated at step 1820, this tensor is only computed at the start of the iterative procedure, and stored in the computer memory, as shown at block 1825. At block 1830 the $S_{i,j,k}^{sim,full}$, $S_{i,j,k}^{sim,scatt}$ are computed each pass through the method.

The solution of the direct problem in block 1815, more specifically, consists of computing the EM fields inside the imaging domain 21 subject to certain boundary conditions and modeling the antennas 165 as the electromagnetic sources. Mathematically, this is performed through the numerical solution of the Maxwell's equations, a set of coupled partial differential equations (PDEs) that give the relationship between the electric and magnetic induction fields and the medium properties. In general, there is no analytical solution to these equations. Therefore, numerical algorithms are used to compute an approximate solution. Several well-known numerical methods exist including but not limited to FEM (Finite Element Methods) or FDTD (Finite-Difference Time-Domain). Numerical approximations of the electric and magnetic induction fields inside the imaging chamber 160 are made for every antenna 165 working as transmitter and receiver by solving Maxwell's equations inside the imaging domain 21 N times, where N is the total number of active antennas, independent of whether the antenna is working as a transmitter and/or receiver.

Next, at step 1835 of the iterative process 1800, the inverse problem is solved. Solving the inverse problem involves modifying the dielectric permittivity $\epsilon(x, y, z)$ in order to make the simulated S-parameter tensors converge to the measured ones. Several mathematical algorithms are available for application in this step 1835, including the Gradient method and the Newton-Kantorovich method. Further details of the inverse problem solution process 1835 are described below, and additional or alternative details of direct and/or inverse problem solution processes suitable for use in some embodiments of the present invention may be described in U.S. Pat. No. 9,072,449 to Semenov, issued Jul. 5, 2016 and entitled "WEARABLE/MAN-PORTABLE ELECTROMAGNETIC TOMOGRAPHIC IMAGING," and U.S. Pat. No. 7,239,731 to Semenov et al., issued Jul. 3, 2007 and entitled "SYSTEM AND METHOD FOR NON-DESTRUCTIVE FUNCTIONAL IMAGING AND MAPPING OF ELECTRICAL EXCITATION OF BIOLOGICAL TISSUES USING ELECTROMAGNETIC FIELD TOMOGRAPHY AND SPECTROSCOPY." The relevant portions thereof are incorporated herein by reference.

As represented at step 1840, the option exists to incorporate pattern recognition and removal techniques into the EMTIR process 1800. For example, the distribution of increments resulting from block 1835, used for updating the dielectric permittivity, may be processed with pattern recognition and removal algorithms in order to remove undesired disturbance effects and improve the quality of the reconstructed images. Suitable pattern recognition and removal techniques include methods of EM Interference Pattern Recognition Tomography (EMIPRT) as disclosed in the aforementioned International Application Serial No. PCT/US16/57254. Such methods may be applied as represented by step 1845.

Once the dielectric permittivity $\epsilon(x, y, z)$ is updated as shown at block 1850, the value of the functional is computed at block 1855. The value of functional corresponds to the difference between the actual (measured) values and the simulated values. If at step 1860 the functional value satisfies pre-defined criteria, which may include defining a percentage value of the initial functional value, then convergence is said to have been reached, and the reconstructed image is obtained plotting the final dielectric permittivity distribution in block 1865. Otherwise, appropriate portions of the procedure are repeated iteratively until convergence is reached.

As noted previously, solving the inverse problem at block 1835 involves modifying the dielectric permittivity $\epsilon(x, y, z)$ in order to make the simulated S-parameter tensors converge to the measured ones. More specifically, input is generated and used in the reconstruction of the permittivity distribution $\epsilon(\vec{r}) \equiv \epsilon(x, y, z) \in C$ inside the chamber 160. The inverse problem solution is the permittivity distribution which minimizes the discrepancy between measured data and simulated data, or minimizes a given norm $$\min_\epsilon \|S^{exp} - S^{thy}[\epsilon]\|. \tag{1}$$

The real-valued functional to be minimized is of the form $$J[\epsilon(\vec{r})] = \sum_{k=1}^{N_f} w_k \sum_{i=1}^{N_{Tx}} \sum_{j=1}^{N_{Rx}} |S_{ij}^{exp} - S_{ij}^{thy}[\epsilon(\vec{r})]|^2, \tag{2}$$

where the $S_{ij}(f_k, \epsilon(\vec{r})) \in C$ are the measured and theoretical scattering matrix elements which depend on the 3-dimensional permittivity distribution $\epsilon(\vec{r}) \equiv \epsilon(x, y, z) \in C$ in the imaging domain 21 and on the given frequency $f_k$. In the functional (2), $N_f$ is the number of frequencies, $N_{Tx}$ is the number of transmitters, $N_{Rx}$ is the number of receivers, and $w_k \in R$ is an additional factor to weight different frequency contributions in the sum.

The scattering matrix elements are obtained from subtracting the measured $S_{ij}$ values of the empty chamber 160 from the values obtained when an object is placed within the chamber, $$S_{ij}^{sct} = S_{ij}^{full} - S_{ij}^{empty} \tag{3}$$

In order to maximize the information about the scatterer in the functional, different normalizations can be used depending on the object under study, including, without limitation:

$$S_{ijk} \equiv \frac{S_{ijk}^{sct}}{S_{ijk}^{empty}} \quad \ldots \text{ antenna-by-antenna} \tag{4a}$$

$$S_{ijk} \equiv \frac{S_{ijk}^{sct}}{S_{i,opp(i),k}^{empty}} \quad \ldots \text{ opposite-antenna} \tag{4b}$$

$$S_{ijk} \equiv \frac{S_{ijk}^{sct}}{\max(S_{ijk}^{empty})} \quad \ldots \text{ maximum-value} \tag{4c}$$

$$S_{ijk} \equiv \frac{S_{ijk}^{sct}}{\min(S_{ijk}^{empty})} \quad \ldots \text{ minimum-value} \tag{4d}$$

Figure 25A:
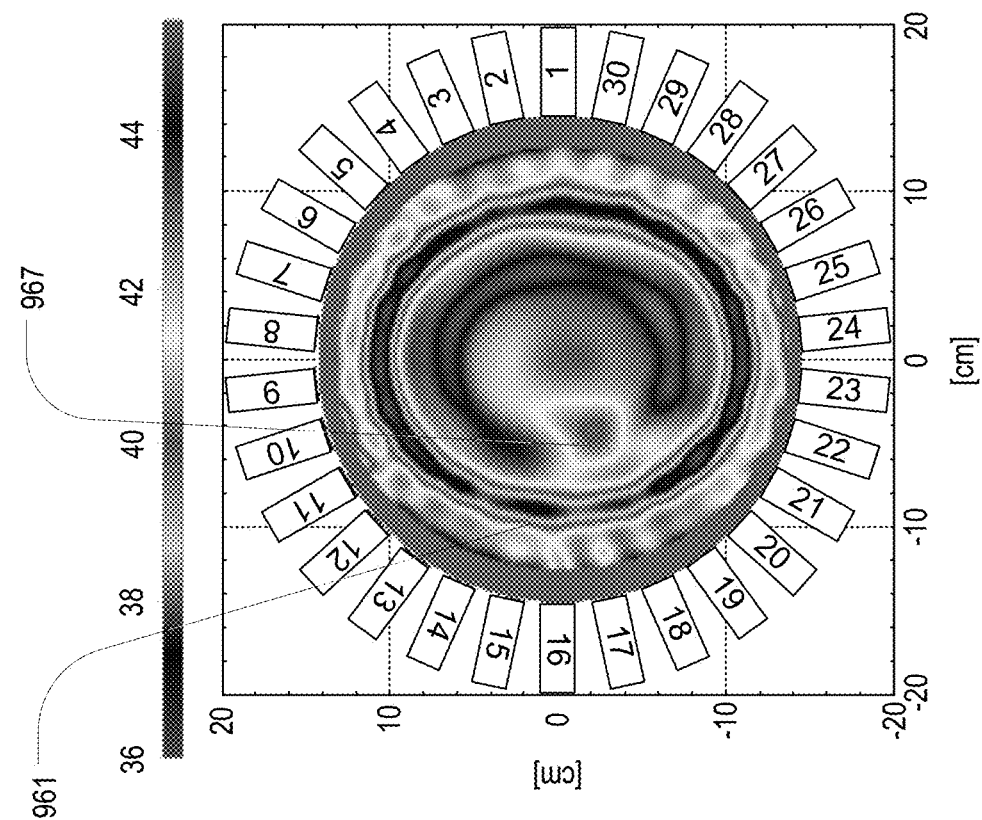
Figure 24A:
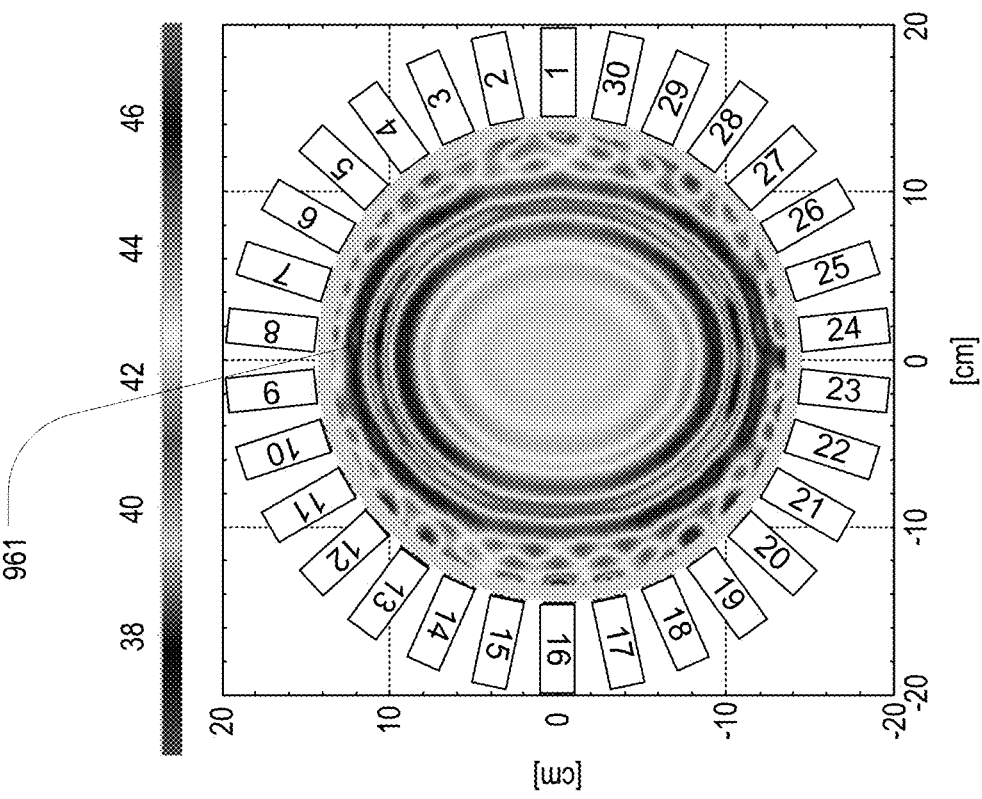
FIGS. 24A and 24B are graphical representations (rendered in a black-and-white version and a color version) of an image reconstruction, for an object, using opposite-antenna normalization.
Figure 25B:
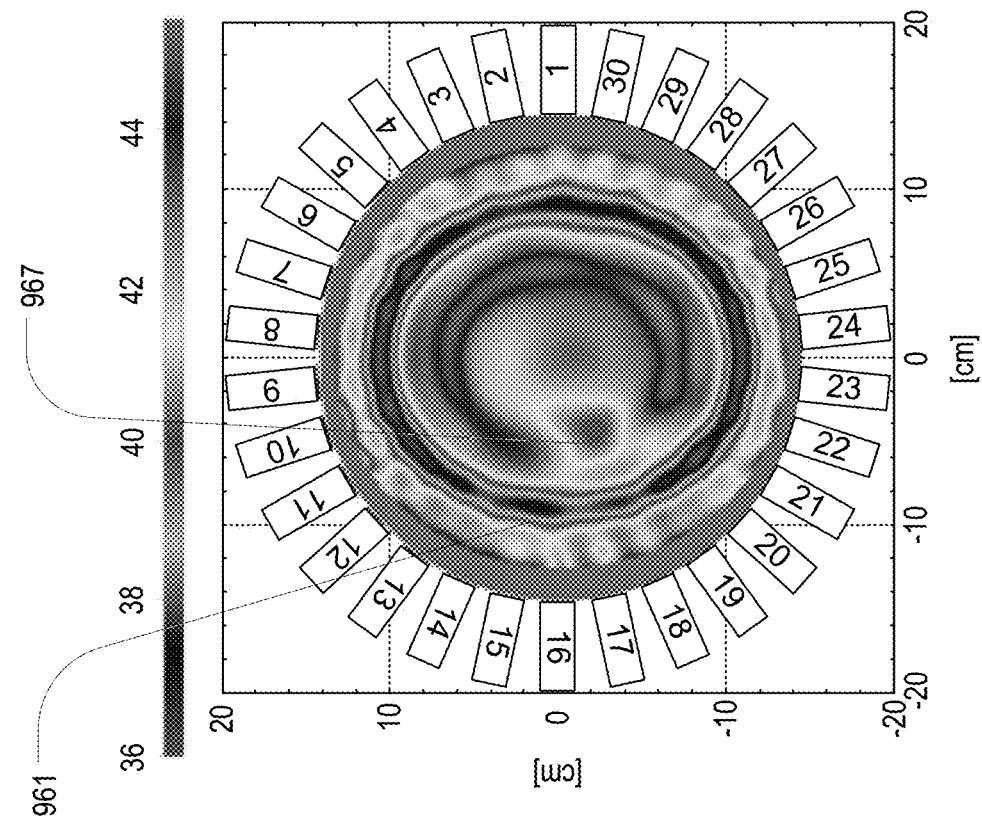
Figure 24B:
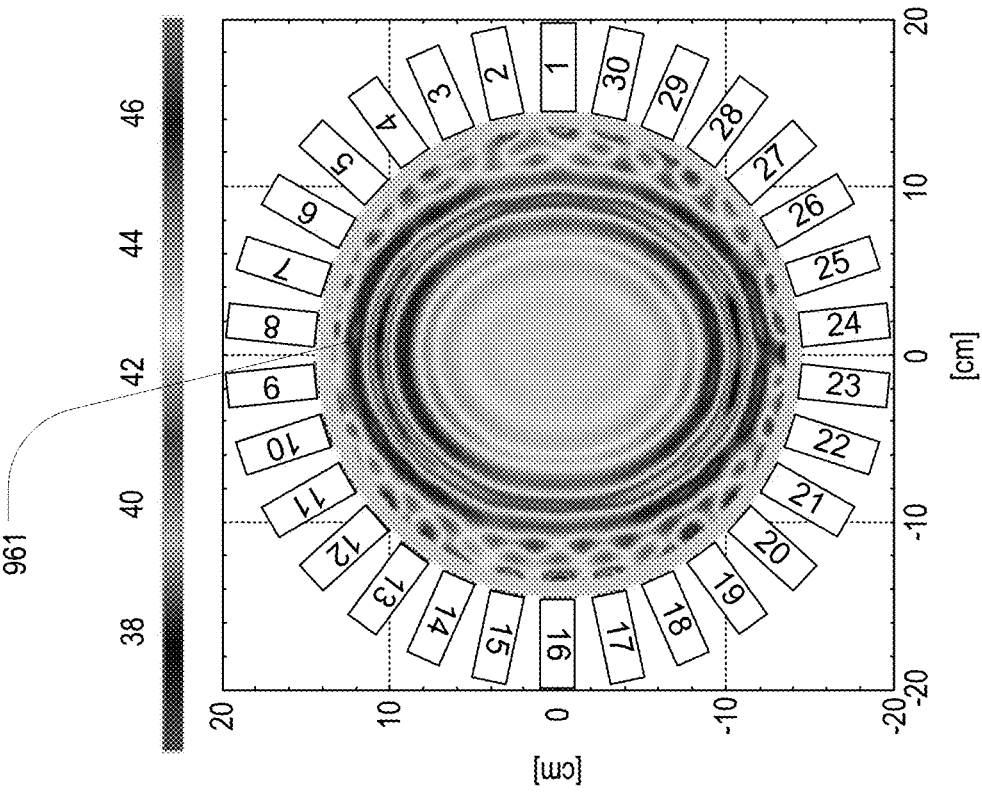

FIGS. 24A and 24B are graphical representations (rendered in a black-and-white version and a color version) of an image reconstruction, for an object, using opposite-antenna normalization as defined in equation (4b) above. FIGS. 25A and 25B are graphical representations (rendered in a black-and-white version and a color version) of an image reconstruction for the same object as that of FIGS. 24A and 24B but using antenna-by-antenna normalization as defined in equation (4a) above. In FIGS. 24A and 24B and FIGS. 25A and 25B, the object under test is a high contrast shell 961 in the form of an elliptical cylinder having a small inhomogeneity 967 placed inside in a location that is off-centered to the left side.

In both cases (i.e., with both types of normalization), the image reconstruction process is in a relatively early iteration. The elliptical shell 961 itself is visible in both cases. However, the inhomogeneity 967 is only visible in FIGS. 25A and 25B, which is the case using antenna-by-antenna normalization. As shown in FIGS. 24A and 24B, the ring-type artifacts present in the opposite-antenna normalization case prevent reconstruction of the small inhomogeneity 967 during early iterations. In some embodiments, these ring-type artifacts may be removed using a pattern removal techniques as described in the aforementioned International Application Serial No. PCT/US16/57254. However, the illustrated comparison demonstrates that antenna-by-antenna normalization may be used to minimize ring-type artifacts without such additional processing, resulting in the small object 967 inside the high contrast shell 961 being more readily visible, particularly in early iterations of the image reconstruction process. This can be further enhanced through the use of a matching media formulated to have dielectric properties similar to the "average" dielectric properties of a human brain, which helps minimize the effects of skull-shielding. Thus, the use of antenna-by-antenna normalization and/or proper a matching media with dielectric properties similar to the average dielectric properties of a human brain can be considered, in at least some embodiments, as an alternative to the use of pattern removal techniques and/or other additional processing techniques.

Furthermore, it will be appreciated that the antenna-by-antenna normalization acts as an intrinsic calibration. If the back-interaction from the head 109 or other object to the antennas 165,765 is weak, the calibration coefficients are equal for the scattered and the empty field. In this case, they drop out:

$$S_{ij} \equiv \frac{c_{ij}^{sct} s_{ij}^{sct}}{c_{ij}^{empty} s_{ij}^{empty}} = \frac{c_{ij}^{empty} s_{ij}^{sct}}{c_{ij}^{empty} s_{ij}^{empty}} = \frac{s_{ij}^{sct}}{s_{ij}^{empty}}, \quad (5)$$

and no calibration is necessary. However, this assumption is no longer valid if the antennas 165,765 are very close to the object 109.

The complex-valued gradient of the functional (2) is obtained via the functional derivative of J with respect to $\epsilon(\vec{r})$ and is given by $$J_{grad}(\vec{r}) \equiv \frac{\delta}{\delta \epsilon(\vec{r})} J[\epsilon(\vec{r})] = \quad (6)$$

$$\sum_{k=1}^{N_f} w_k \sum_{i=1}^{N_{Tx}} \sum_{j=1}^{N_{Rx}} conj\left(\vec{E_I}(f_k, \vec{r}) \cdot \vec{E_J}(f_k, \vec{r})\right)\left(s_{ij}^{exp} - s_{ij}^{thy}\right)$$

where $\vec{E}_{i,j}(f_k, \vec{r})$ are the simulated EM fields transmitted from antenna i and j, respectively, and conj denotes complex conjugation. It is noted that a constant factor $(2\pi/\lambda_k)^2$ has been absorbed into $w_k$.

Finally, the permittivity contribution in the imaging domain 21 is obtained via the iterative process $$\epsilon(\vec{r})^{n+1} = \epsilon(\vec{r})^n - h^n J_{grad}^n(\vec{r}) \quad (7)$$

where $h^n \in R$ denotes the real-valued step-size at a given iteration n.

The optimization problem to minimize the functional in order to reconstruct the permittivity distribution is an ill-posed problem because the number of measured values is much smaller than the number of unknowns of the inverse problem. Therefore, a regularization procedure is preferably used. One of the possible options is the classical Tikhonov regularization method, which is robust and easy to implement.

The resulting image can be used for any of a variety of purposes, including for assessment, diagnosis, 4D dynamic fused electromagnetic tomography, monitoring viability and functional conditions using such EMT, and others involving any functional or pathological conditions of brain tissue, including but not limited to, ischemia, hypoxia, blood content, acute and chronic stroke and differentiation of stroke type (such as ischemic or hemorrhagic), edema, traumatic brain injuries (TBI), tumors and differentiation of tumor type, and the like.

Based on the foregoing information, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention.

Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements; the present invention being limited only by the claims appended hereto and the equivalents thereof

What is claimed is:

1. An electromagnetic tomographic system for imaging a human head, comprising:
   a base;
   an imaging chamber, supported on the base, that defines an imaging domain in which a human head is received;
   at least one ring of antennas, supported by the imaging chamber and encircling the imaging domain;
   a plurality of antenna controllers, each antenna controller comprising circuitry carried on a printed circuit board, wherein each of the plurality of antenna controllers is dedicated to a respective antenna in the ring of antennas, and wherein the circuitry of each respective antenna controller controls operation of the corresponding antenna and also provides, as output, data representative of measured electromagnetic field signals received by such antenna; and
   an image processing computer system that receives, from the plurality of antenna controllers, the output data representative of the measured electromagnetic field signals received by the respective antennas and derives image data therefrom.

2. The electromagnetic tomographic system of claim 1, wherein the circuitry for each respective antenna controller is carried on one or more dedicated printed circuit board that are separate from the respective printed circuit boards for the other antenna controllers.

3. The electromagnetic tomographic system of claim 2, wherein the circuitry for each antenna controller includes radio frequency (RF) transceiver circuitry that has a transmit side and a receive side that are alternately connected to the antenna using an RF switch.

4. The electromagnetic tomographic system of claim 2, further comprising a plurality of antenna adapters, wherein each of the plurality of antenna adapters is dedicated to a respective antenna in the ring of antennas, and wherein the antennas and antennas adapters include circuitry that is carried on a dedicated printed circuit board that is separate from the respective printed circuit boards for the other antennas and antenna adapters.

5. The electromagnetic tomographic system of claim 4, wherein the circuitry for each antenna and antenna adapter and the circuitry for the corresponding antenna controller are carried together on a single respective printed circuit board.

6. The electromagnetic tomographic system of claim 4, wherein the circuitry for each antenna and antenna adapter is carried on a first printed circuit board in a first module and the circuitry for the antenna controller corresponding to the antenna and antenna adapter is carried on a second printed circuit board in a second module.

7. The electromagnetic tomographic system of claim 6, wherein each respective first printed circuit board module is connected to its corresponding second printed circuit board module via one or more cable.

8. The electromagnetic tomographic system of claim 6, wherein the second printed circuit boards for all of the antennas are housed together in a location separate from the antenna rings.

9. The electromagnetic tomographic system of claim 6, wherein the plurality of second printed circuit boards are arranged in a ring around the first printed circuit boards such that each respective second printed circuit board is disposed adjacent its corresponding first printed circuit board.

10. The electromagnetic tomographic system of claim 2, wherein the circuitry for each respective antenna controller includes an analog to digital converter (ADC), carried on the one or more dedicated printed circuit board, such that the data representative of measured electromagnetic field signals received by the corresponding antenna may be generated.

11. The electromagnetic tomographic system of claim 10, wherein the circuitry for each respective antenna controller includes a digital signal processor carried on the one or more dedicated printed circuit boards.

12. The electromagnetic tomographic system of claim 1, wherein the imaging chamber is cylindrical and includes at least three rings of antennas.

13. The electromagnetic tomographic system of claim 12, wherein each of the at least three rings of antennas includes a number of antennas that is equal to the number of antennas in each of the other rings.

14. The electromagnetic tomographic system of claim 1, wherein the imaging chamber is semispherical and includes at least three rings of antennas.

15. The electromagnetic tomographic system of claim 14, wherein each of the at least three rings of antennas includes a number of antennas that is different from the number of antennas in each of the other rings.

16. The electromagnetic tomographic system of claim 1, wherein the imaging chamber translates relative to the base.

17. The electromagnetic tomographic system of claim 16, wherein the imaging chamber translates horizontally relative to the base.

18. The electromagnetic tomographic system of claim 16, wherein the imaging chamber translates vertically relative to the base.

19. The electromagnetic tomographic system of claim 16, wherein the imaging chamber rotates upward and downward relative to the base.

20. The electromagnetic tomographic system of claim 1, wherein the antennas are waveguide antennas.

21. The electromagnetic tomographic system of claim 1, wherein the antennas are slot antennas.

22. The electromagnetic tomographic system of claim 1, wherein the image processing computer system is integrated with the electromagnetic tomographic scanner.

23. The electromagnetic tomographic system of claim 1, wherein the image processing computer system is disposed in the same room as the electromagnetic tomographic scanner.

24. The electromagnetic tomographic system of claim 1, wherein the image processing computer system is disposed in a room that is different from a room in which the electromagnetic tomographic scanner is disposed.

25. An electromagnetic tomographic system for imaging a human head, comprising:
a base;
an imaging chamber, supported on the base, that defines an imaging domain in which a human head is received;
at least one ring of antennas, supported by the imaging chamber and encircling the imaging domain;
a plurality of antenna controllers, each antenna controller comprising circuitry, utilizing a superheterodyne technology-based architecture, that is dedicated to a respective antenna in the ring of antennas, and wherein the circuitry of each respective antenna controller controls operation of the corresponding antenna and also provides, as output, data representative of measured electromagnetic field signals received by such antenna; and
an image processing computer system that receives, from the plurality of antenna controllers, the output data representative of the measured electromagnetic field signals received by the respective antennas and derives image data therefrom.

26. An electromagnetic tomographic scanner for use in imaging a human head, comprising:
a base;
an imaging chamber, supported on the base, that defines an imaging domain;
at least one ring of antennas, supported by the imaging chamber and encircling the imaging domain;
a plurality of antenna controllers, each antenna controller comprising circuitry carried on a printed circuit board, wherein each of the plurality of antenna controllers is dedicated to a respective antenna in the ring of antennas, and wherein the circuitry of each respective antenna controller controls operation of the corresponding antenna and also provides, as output, data representative of measured electromagnetic field signals received by such antenna.

27. An electromagnetic tomographic scanner for use in imaging a human head, comprising:
a base;
an imaging chamber, supported on the base, that defines an imaging domain;
at least one ring of antennas, supported by the imaging chamber and encircling the imaging domain; and
a plurality of antenna controllers, each antenna controller comprising circuitry, utilizing a superheterodyne technology-based architecture, that is dedicated to a respective antenna in the ring of antennas;
wherein the circuitry of each respective antenna controller controls operation of the corresponding antenna and also provides, as output, data representative of measured electromagnetic field signals received by such antenna.

* * * * *